(12) United States Patent
Naftalovitz et al.

(10) Patent No.: US 9,878,106 B2
(45) Date of Patent: Jan. 30, 2018

(54) MULTI-CHAMBER SYRINGE

(71) Applicant: ELCAM MEDICAL AGRICULTURAL COOPERATIVE ASSOCIATION LTD., Merom Hagalil (IL)

(72) Inventors: Ziv Naftalovitz, West Galilee (IL); Keith Finger, MacFarlan, WV (US); Ilan Shaul Shopen, Zefat (IL); Tsachi Shaked, Merom Hagalil (IL)

(73) Assignee: ELCAM MEDICAL AGRICULTURAL COOPERATIVE, Merom Hagalil (IL)

(*) Notice: Subject to any disclaimer, the term of this patent is extended or adjusted under 35 U.S.C. 154(b) by 113 days.

(21) Appl. No.: 14/434,921

(22) PCT Filed: Oct. 14, 2013

(86) PCT No.: PCT/IL2013/050828
§ 371 (c)(1),
(2) Date: Apr. 10, 2015

(87) PCT Pub. No.: WO2014/061014
PCT Pub. Date: Apr. 24, 2014

(65) Prior Publication Data
US 2015/0250952 A1 Sep. 10, 2015

Related U.S. Application Data

(60) Provisional application No. 61/713,946, filed on Oct. 15, 2012, provisional application No. 61/835,611, filed on Jun. 16, 2013.

(51) Int. Cl.
A61M 5/315 (2006.01)
A61M 5/14 (2006.01)
(Continued)

(52) U.S. Cl.
CPC ........ A61M 5/31596 (2013.01); A61M 5/007 (2013.01); A61M 5/1408 (2013.01);
(Continued)

(58) Field of Classification Search
CPC .......... A61M 2005/1403; A61M 2005/31598; A61M 5/007; A61M 5/1408;
(Continued)

(56) References Cited

U.S. PATENT DOCUMENTS 3,511,239 A 5/1970 Tuschhoff
3,685,514 A 8/1972 Cheney
(Continued)

FOREIGN PATENT DOCUMENTS

CN 101203327 6/2008
EP 2361107 8/2011
(Continued)

Primary Examiner — Quynh-Nhu H Vu
(74) Attorney, Agent, or Firm — Sughrue Mion, PLLC

(57) ABSTRACT

A medical fluid supply device including at least first and second fluid containers which are arranged to be mutually displaceable, at least first and second selectably openable fluid communication pathways associated with the first and second fluid containers and at least one selector switch assembly for selectably opening the first and second selectably openable fluid communication pathways, mutual displacement of the first and second fluid containers changing the amount of fluid in at least one of the at least first and second fluid containers in accordance with a state of the at least one selector switch assembly.

19 Claims, 62 Drawing Sheets

(51) Int. Cl.
*A61M 5/19* (2006.01)
*A61M 5/00* (2006.01)

(52) U.S. Cl.
CPC ............ *A61M 5/1409* (2013.01); *A61M 5/19* (2013.01); *A61M 5/31511* (2013.01); *A61M 5/31525* (2013.01); *A61M 2005/1403* (2013.01); *A61M 2005/31598* (2013.01)

(58) Field of Classification Search
CPC .. A61M 5/1409; A61M 5/19; A61M 5/31511; A61M 5/31525; A61M 5/31596
See application file for complete search history.

(56) References Cited

U.S. PATENT DOCUMENTS

| | | | |
|---|---|---|---|
| 3,872,864 A | 3/1975 | Allen, Jr. | |
| 3,881,484 A | 5/1975 | Gidcumb, Jr. | |
| 3,946,732 A | 3/1976 | Hurscham | |
| 3,985,122 A | 10/1976 | Topham | |
| 4,109,653 A | 8/1978 | Kozam et al. | |
| 4,185,628 A | 1/1980 | Kopfer | |
| 4,188,949 A | 2/1980 | Antoshkiw | |
| 4,439,184 A | 3/1984 | Wheeler | |
| 4,465,476 A | 8/1984 | Gahwiler | |
| 4,496,344 A | 1/1985 | Kamstra | |
| 4,610,666 A | 9/1986 | Pizzino | |
| 4,613,326 A | 9/1986 | Szwarc | |
| 4,655,747 A | 4/1987 | Allen, Jr. | |
| 4,713,060 A | 12/1987 | Riuli | |
| 4,861,335 A | 8/1989 | Reynolds | |
| 5,174,475 A * | 12/1992 | Day | A61K 31/415 222/135 |
| 5,372,586 A | 12/1994 | Haber et al. | |
| 5,395,325 A | 3/1995 | Moreno | |
| 5,496,284 A | 3/1996 | Waldenburg | |
| 5,971,953 A | 10/1999 | Bachynsky | |
| 7,892,210 B2 | 2/2011 | Ranalletta et al. | |
| 7,938,296 B2 | 5/2011 | Keller | |
| 7,951,108 B2 | 5/2011 | Harper et al. | |
| 7,998,106 B2 | 8/2011 | Thorne, Jr. et al. | |
| 8,936,577 B2 | 1/2015 | Lee et al. | |
| 2004/0044316 A1 | 3/2004 | Greenfield et al. | |
| 2005/0177100 A1 | 8/2005 | Harper et al. | |
| 2007/0088282 A1 | 4/2007 | Ranalletta | |
| 2007/0208295 A1 | 9/2007 | Oloodmiyazdi et al. | |
| 2008/0167621 A1 * | 7/2008 | Wagner | A61M 5/19 604/191 |
| 2009/0127289 A1 * | 5/2009 | Keller | B05C 17/00509 222/135 |
| 2010/0063474 A1 | 3/2010 | Evans, Jr. | |
| 2010/0114067 A1 | 5/2010 | Trieu et al. | |
| 2010/0228121 A1 | 9/2010 | Kazuhiro et al. | |
| 2011/0184348 A1 * | 7/2011 | Bates | A61M 5/14216 604/131 |
| 2012/0197232 A1 | 8/2012 | Lee | |
| 2012/0323173 A1 | 12/2012 | Thorne, Jr. et al. | |

FOREIGN PATENT DOCUMENTS

| | | |
|---|---|---|
| WO | 2007003063 | 1/2007 |
| WO | 2007041512 A2 | 4/2007 |
| WO | 2010030593 | 3/2010 |
| WO | 2010051376 | 5/2010 |
| WO | 2013010631 | 1/2013 |
| WO | 2013021186 | 2/2013 |

* cited by examiner

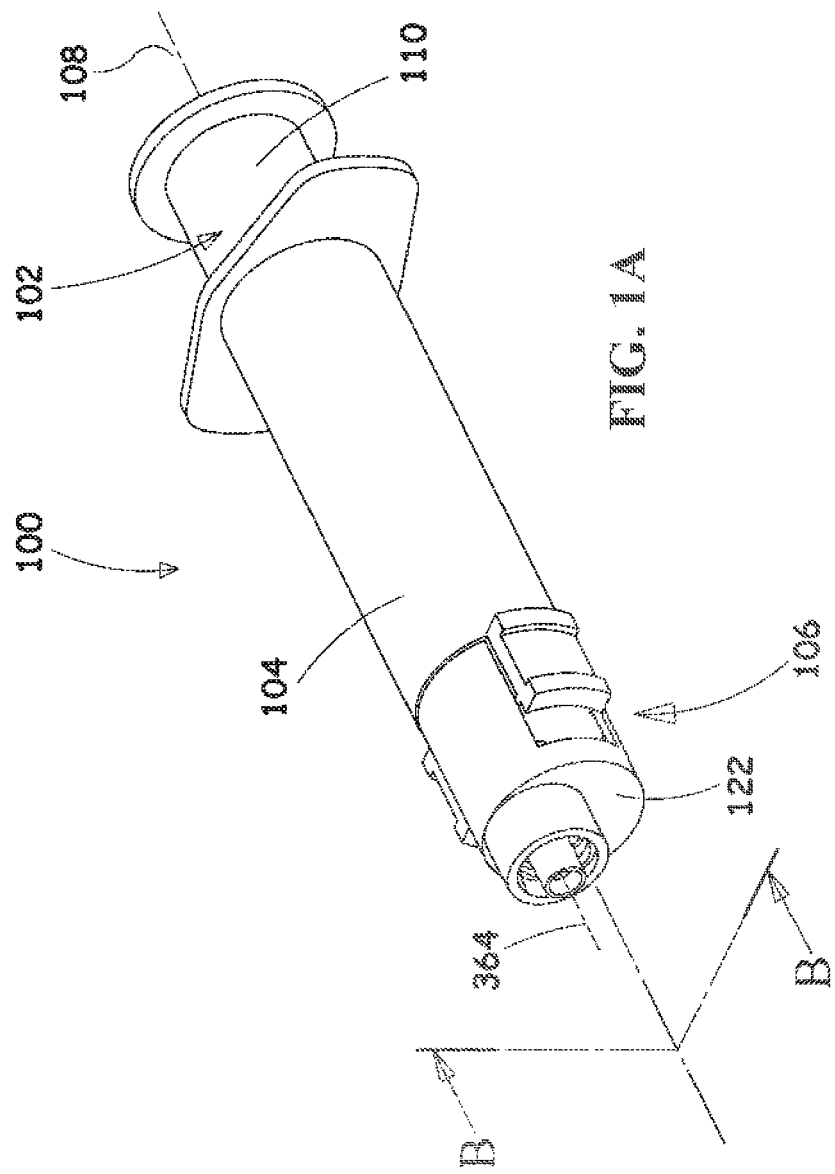

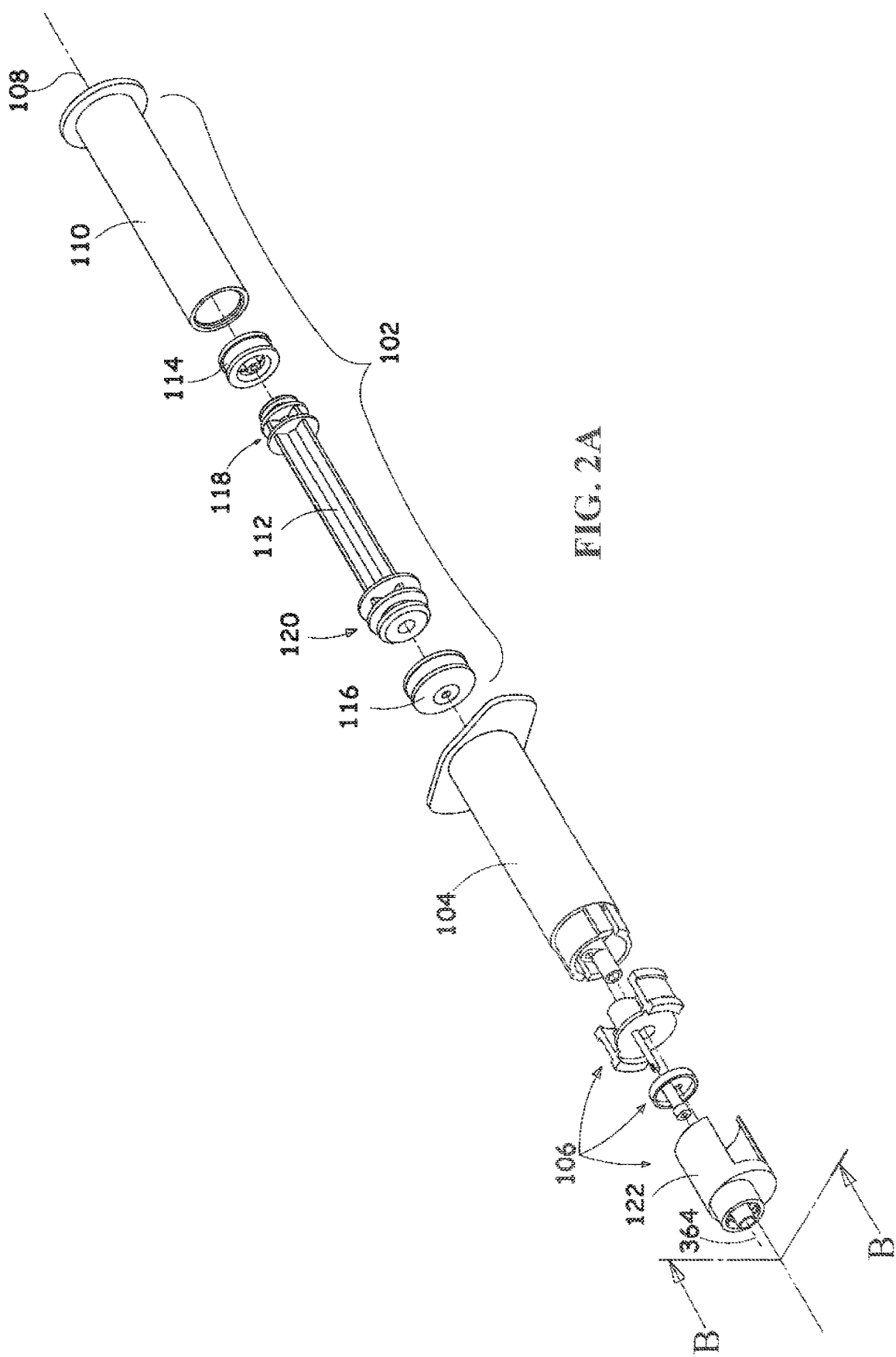

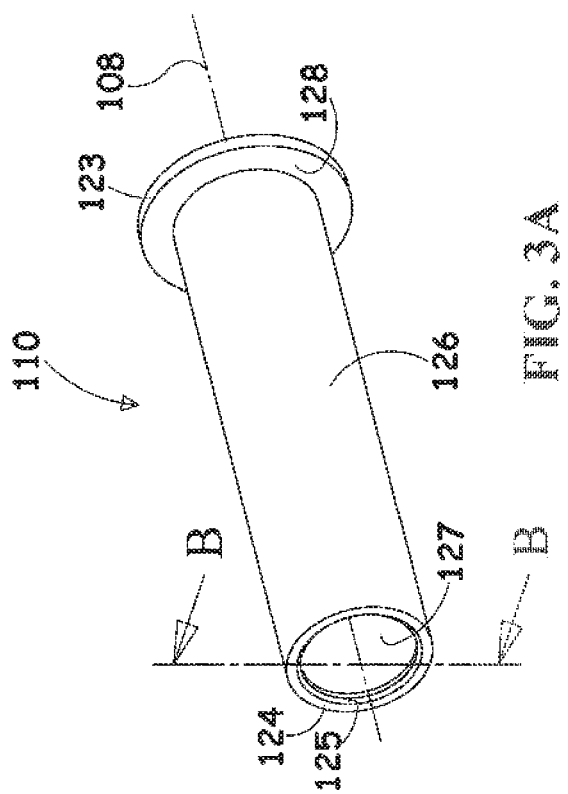
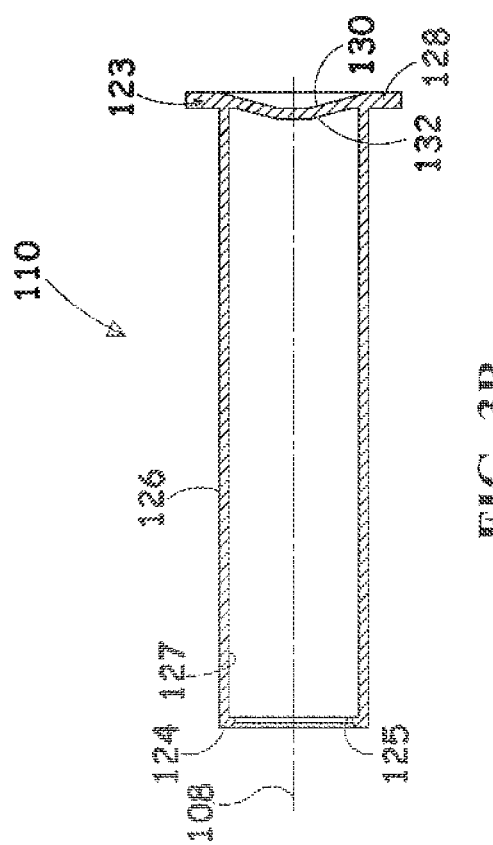

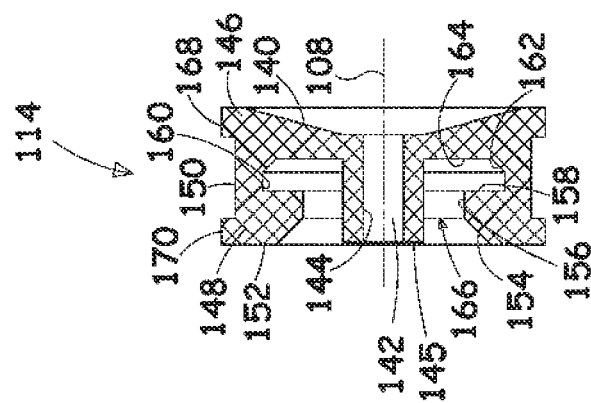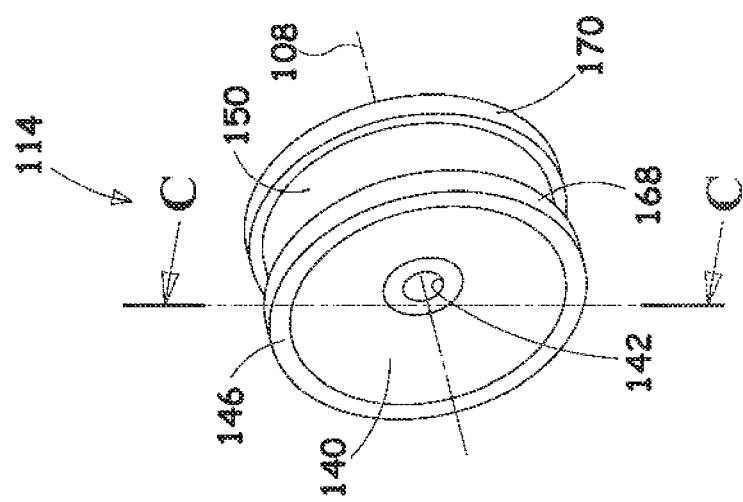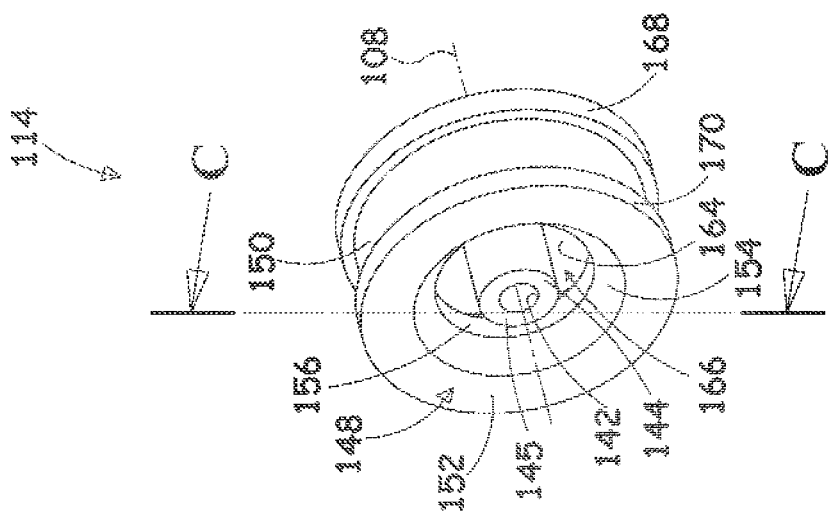

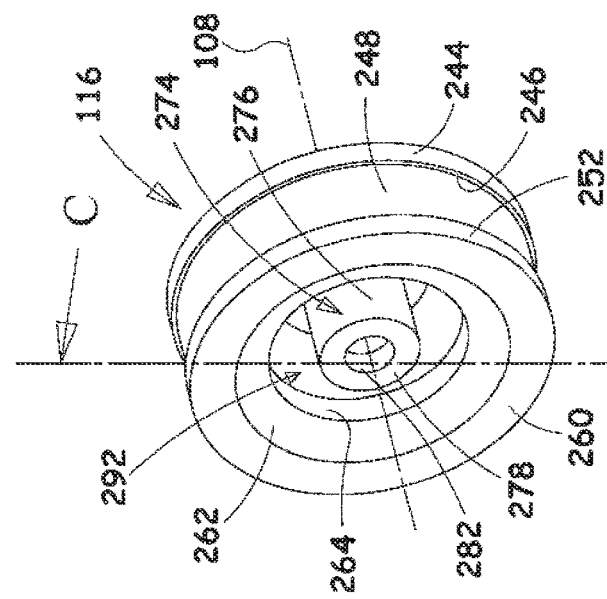
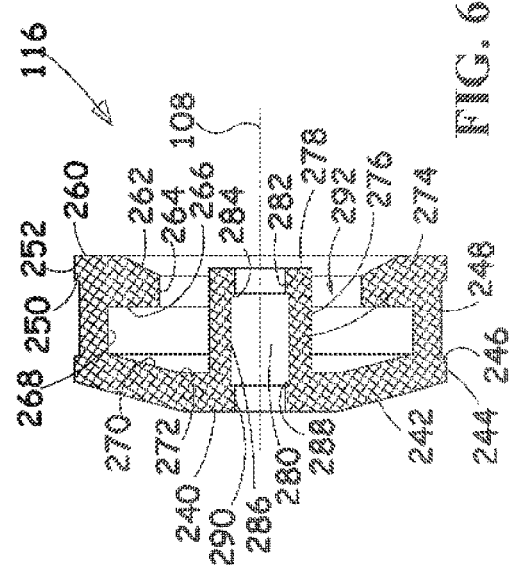
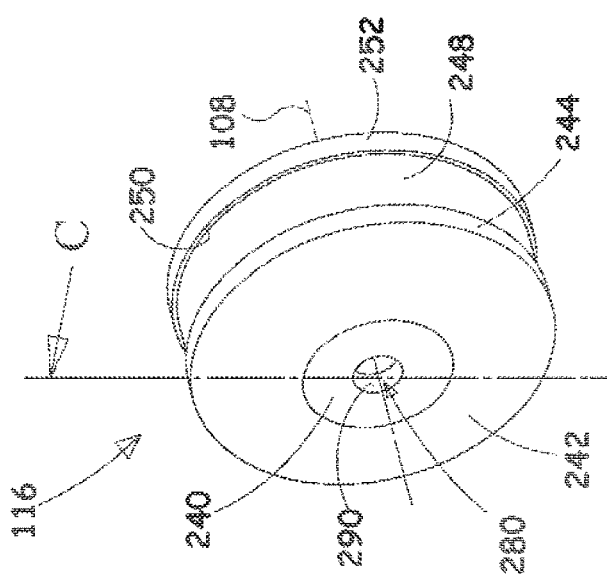

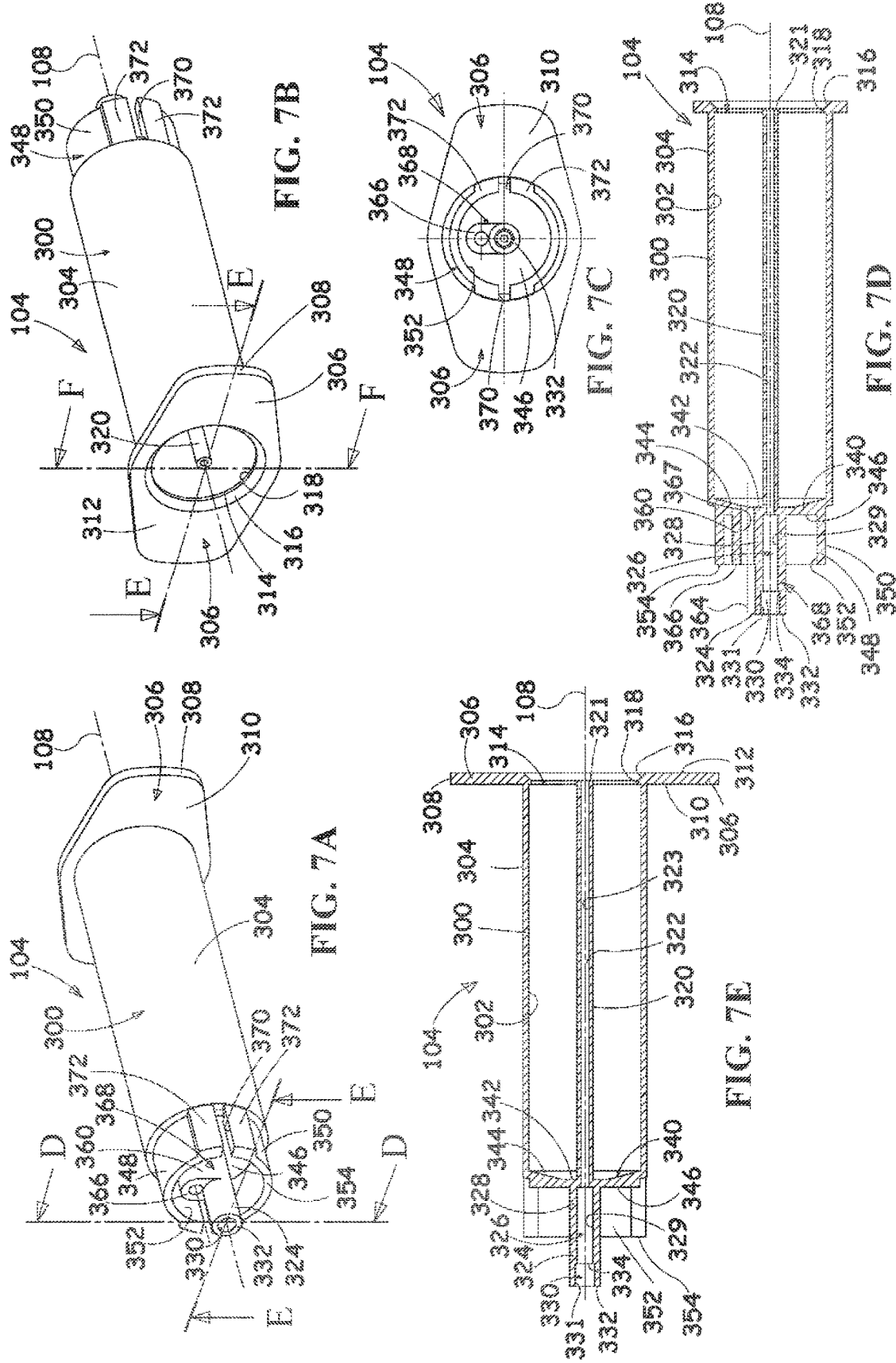

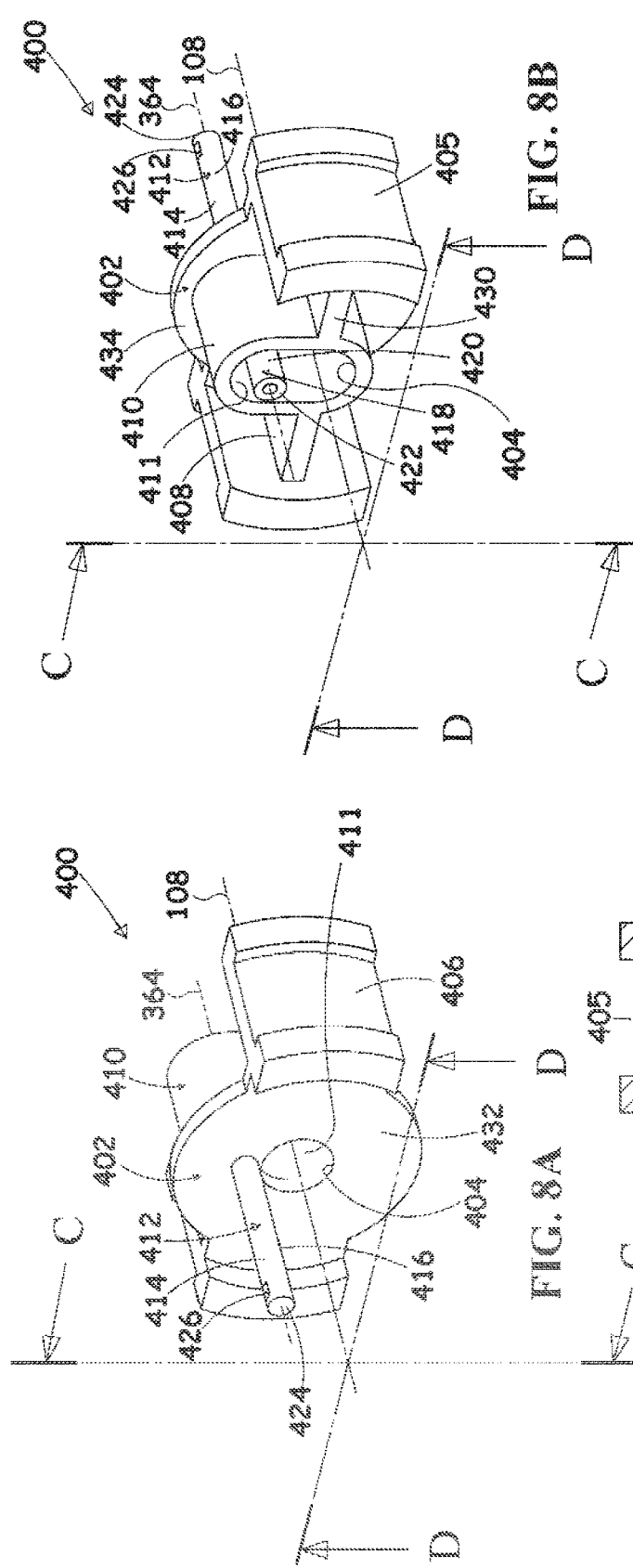

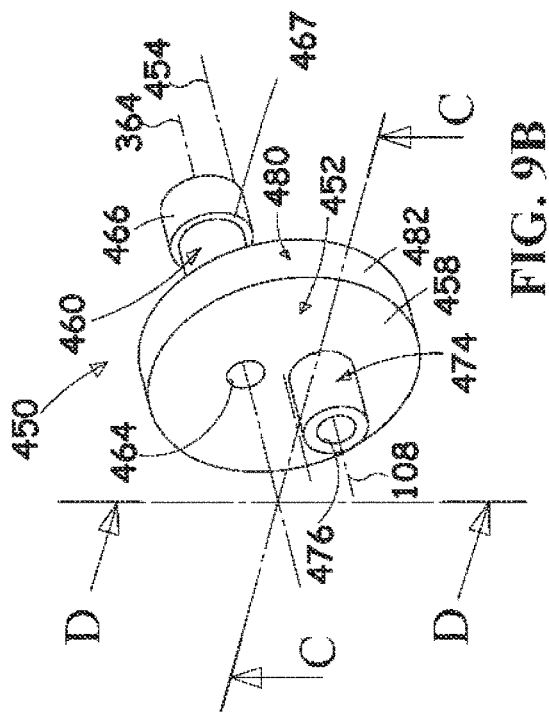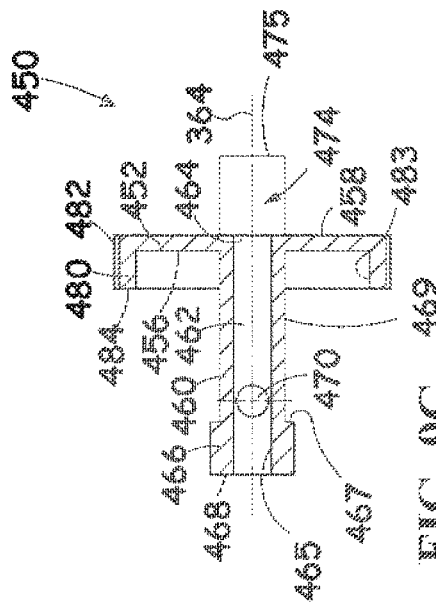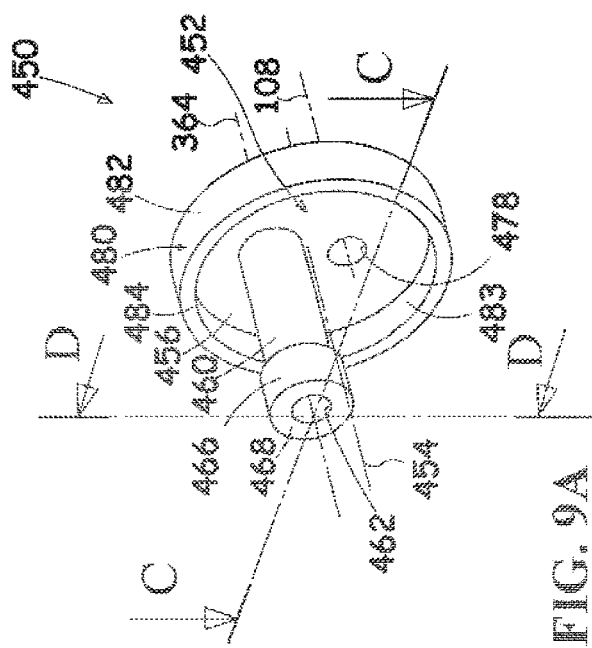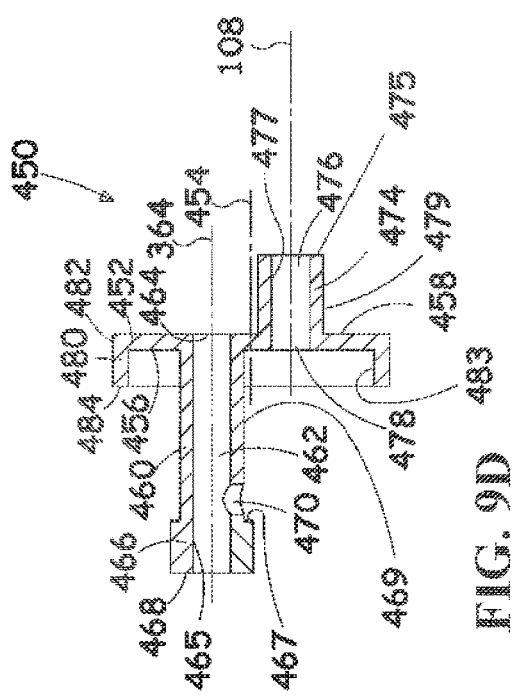

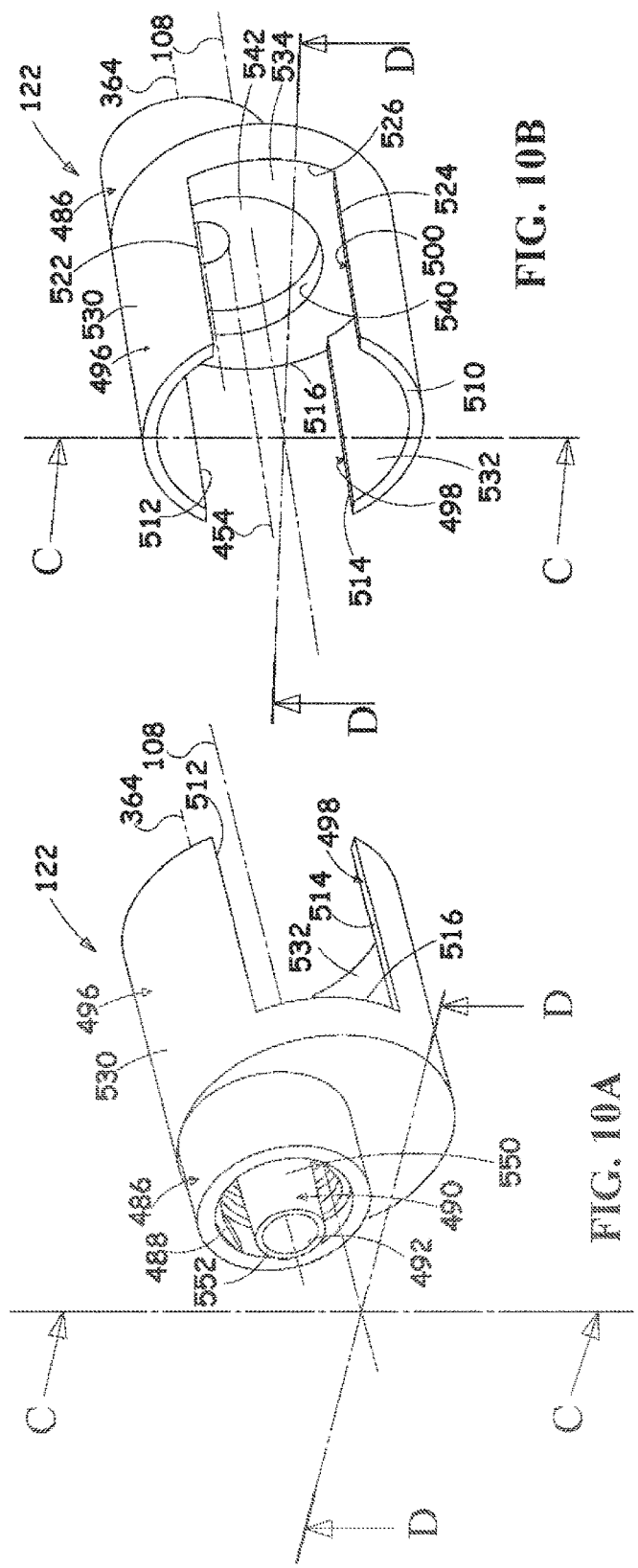
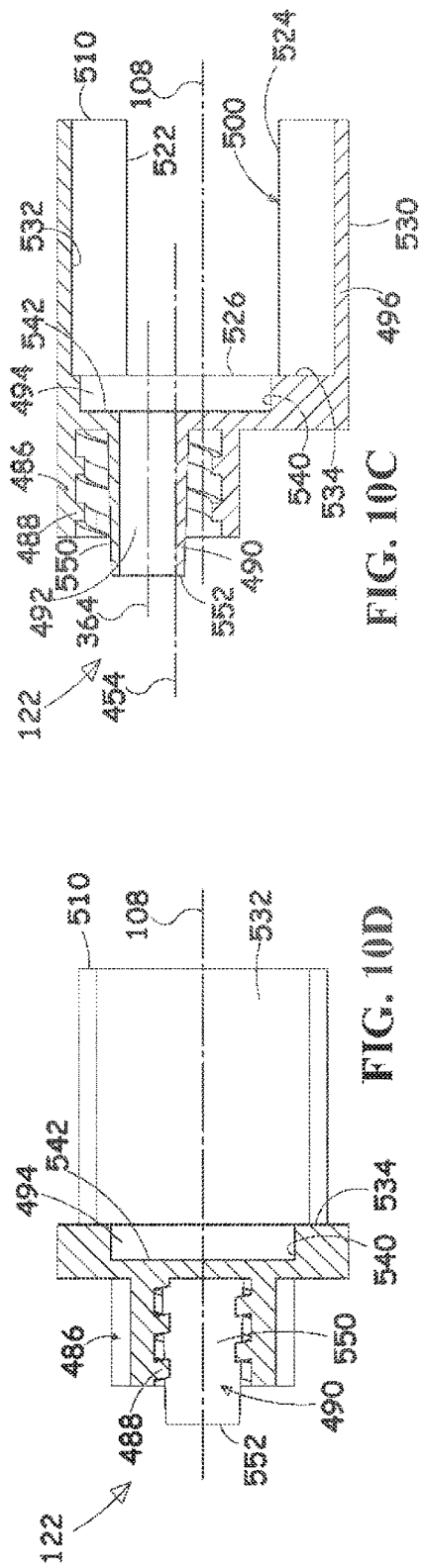
FIG. 10A
FIG. 10B
FIG. 10C
FIG. 10D

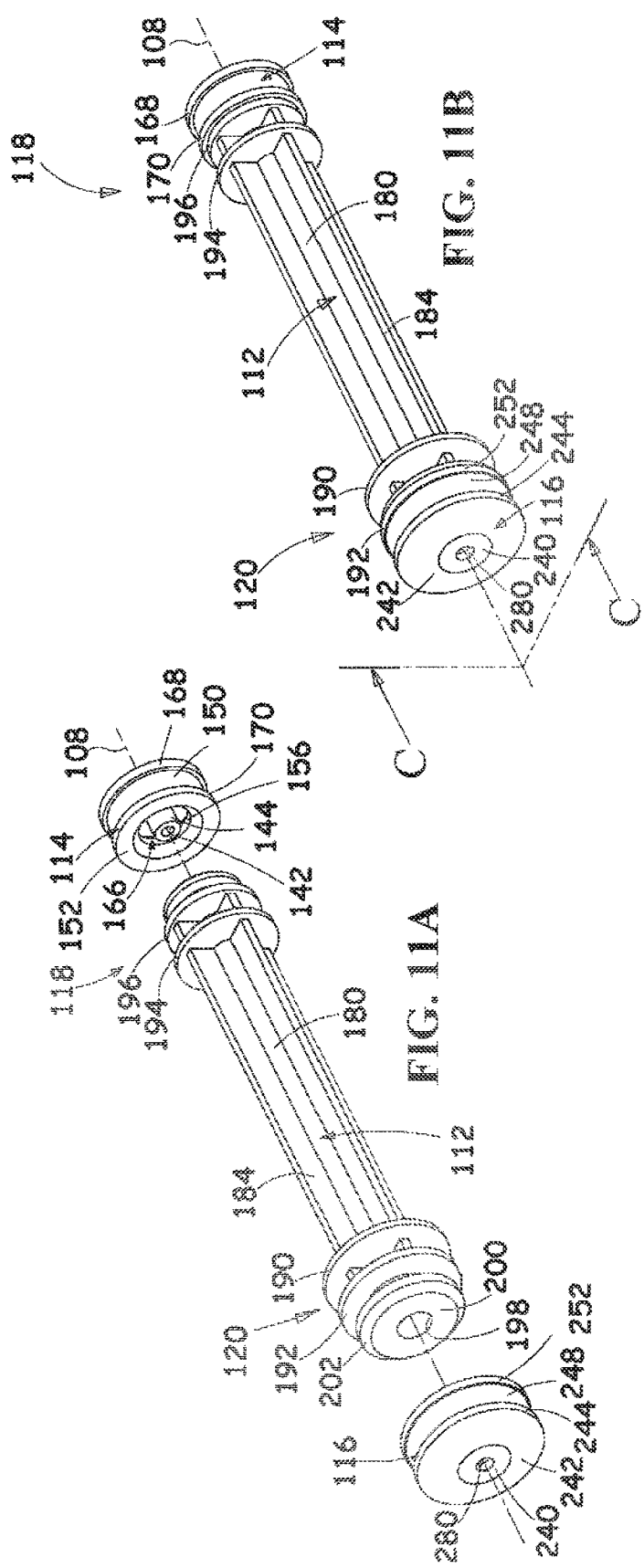

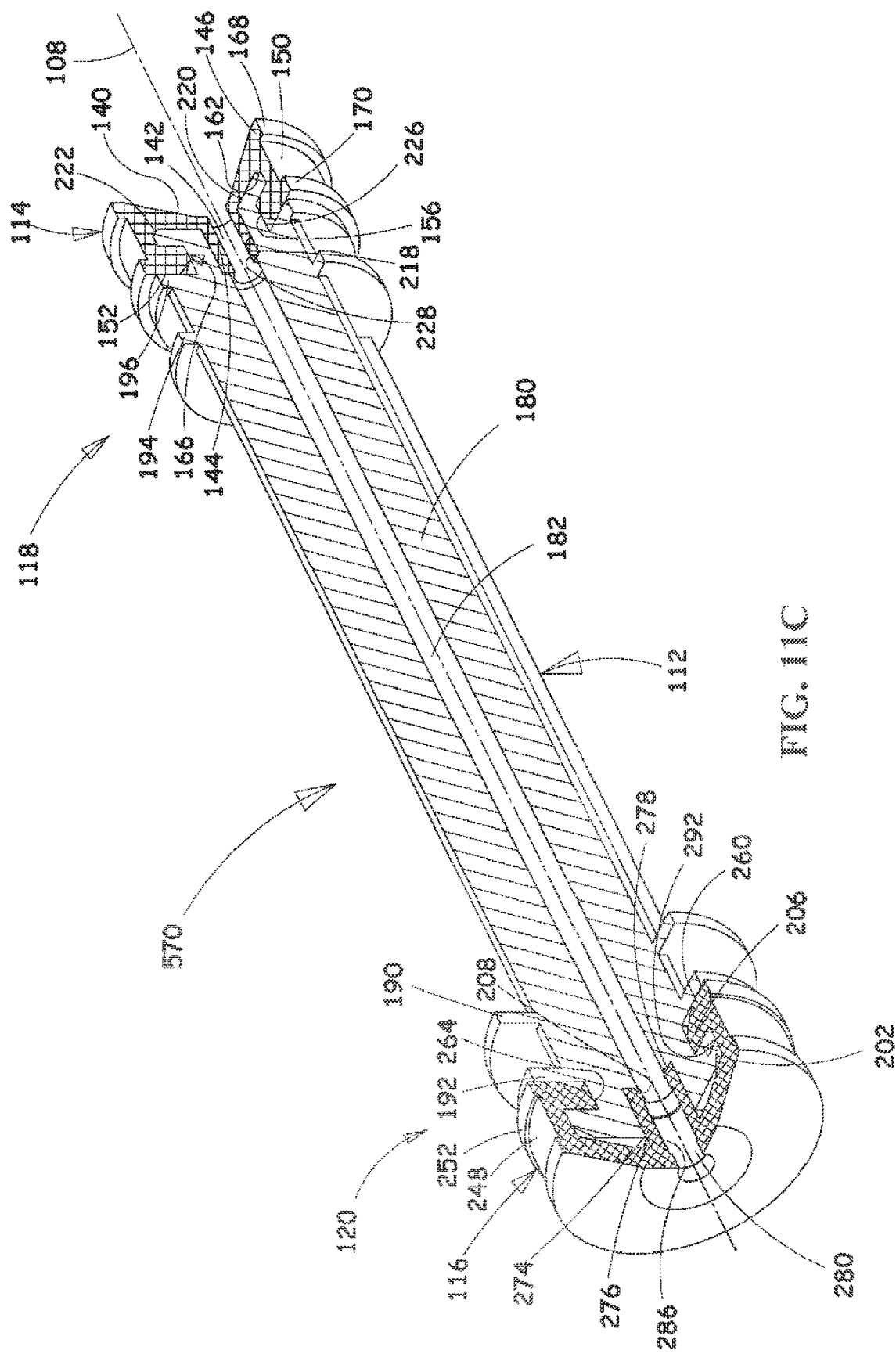

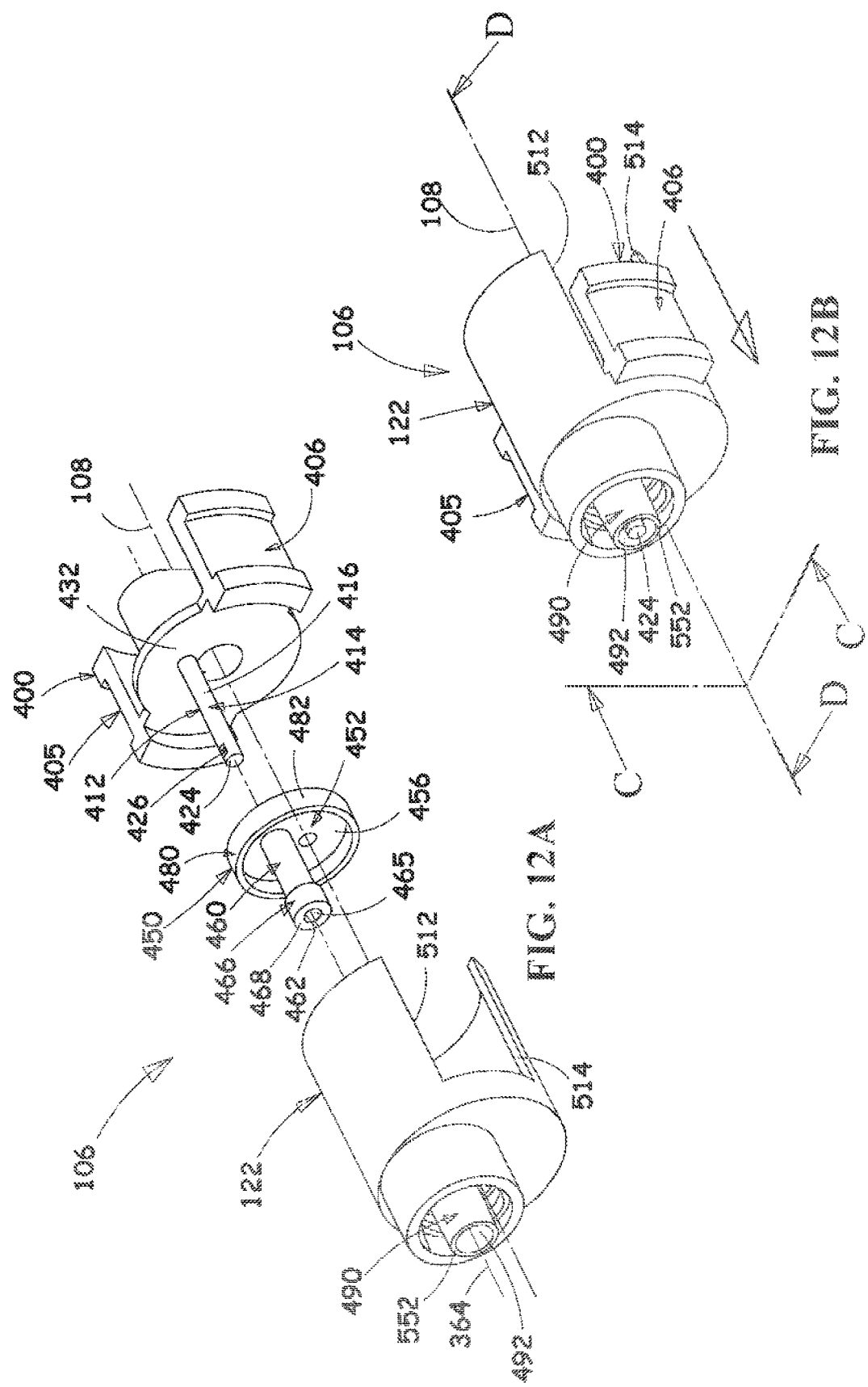

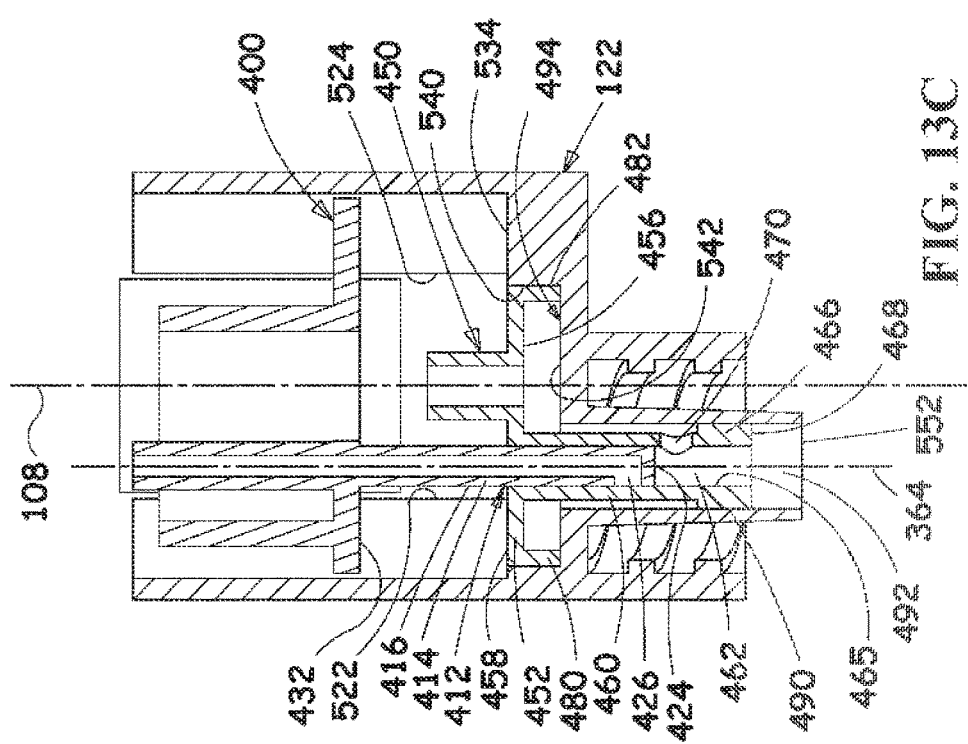
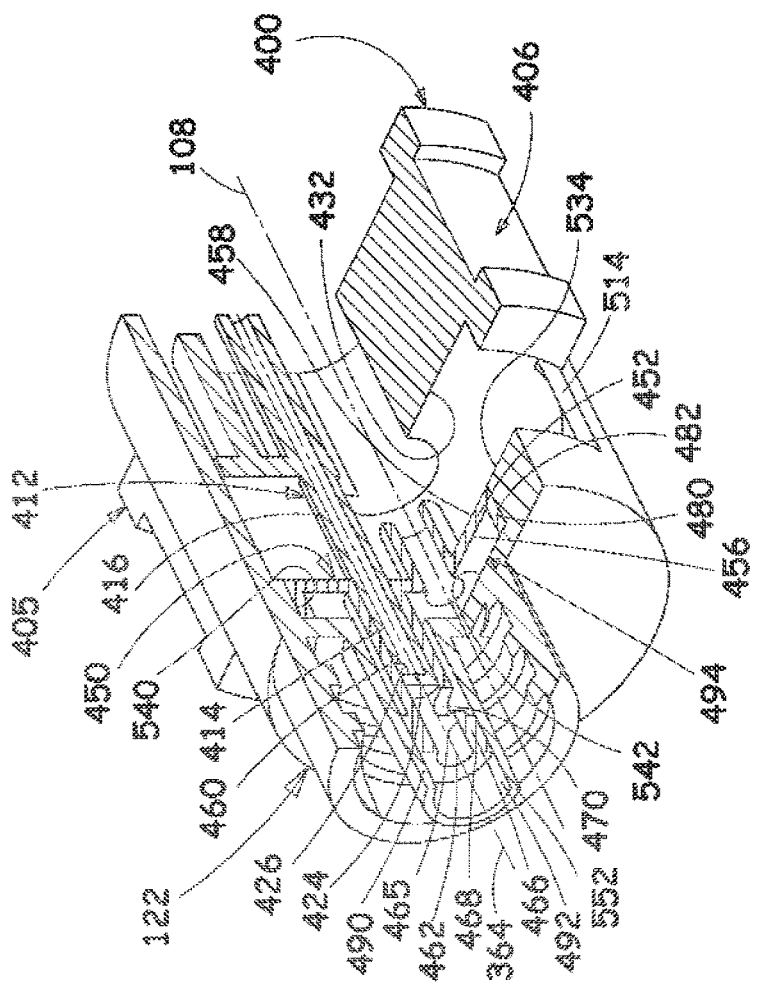
FIG. 13C
FIG. 13B

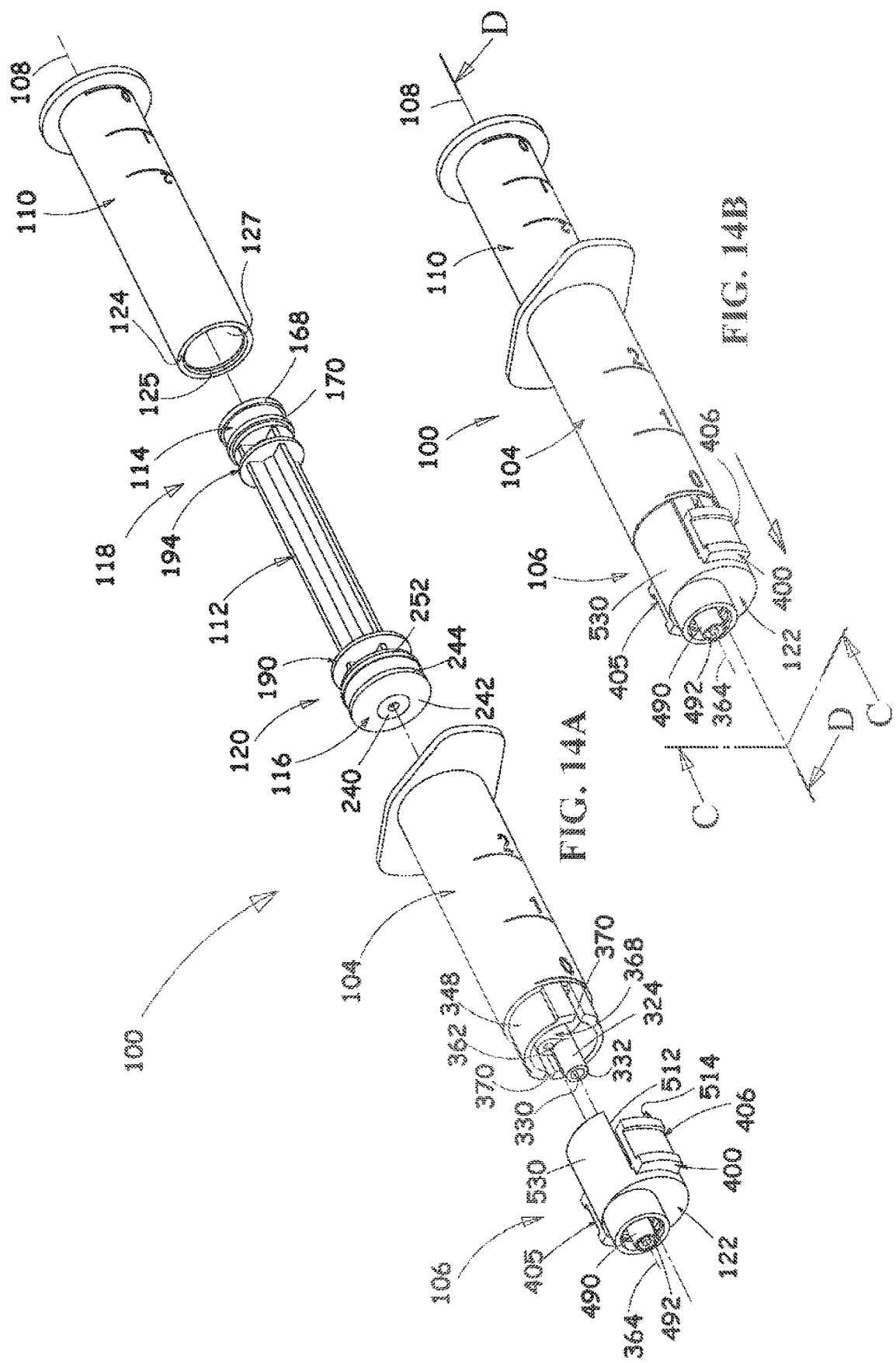

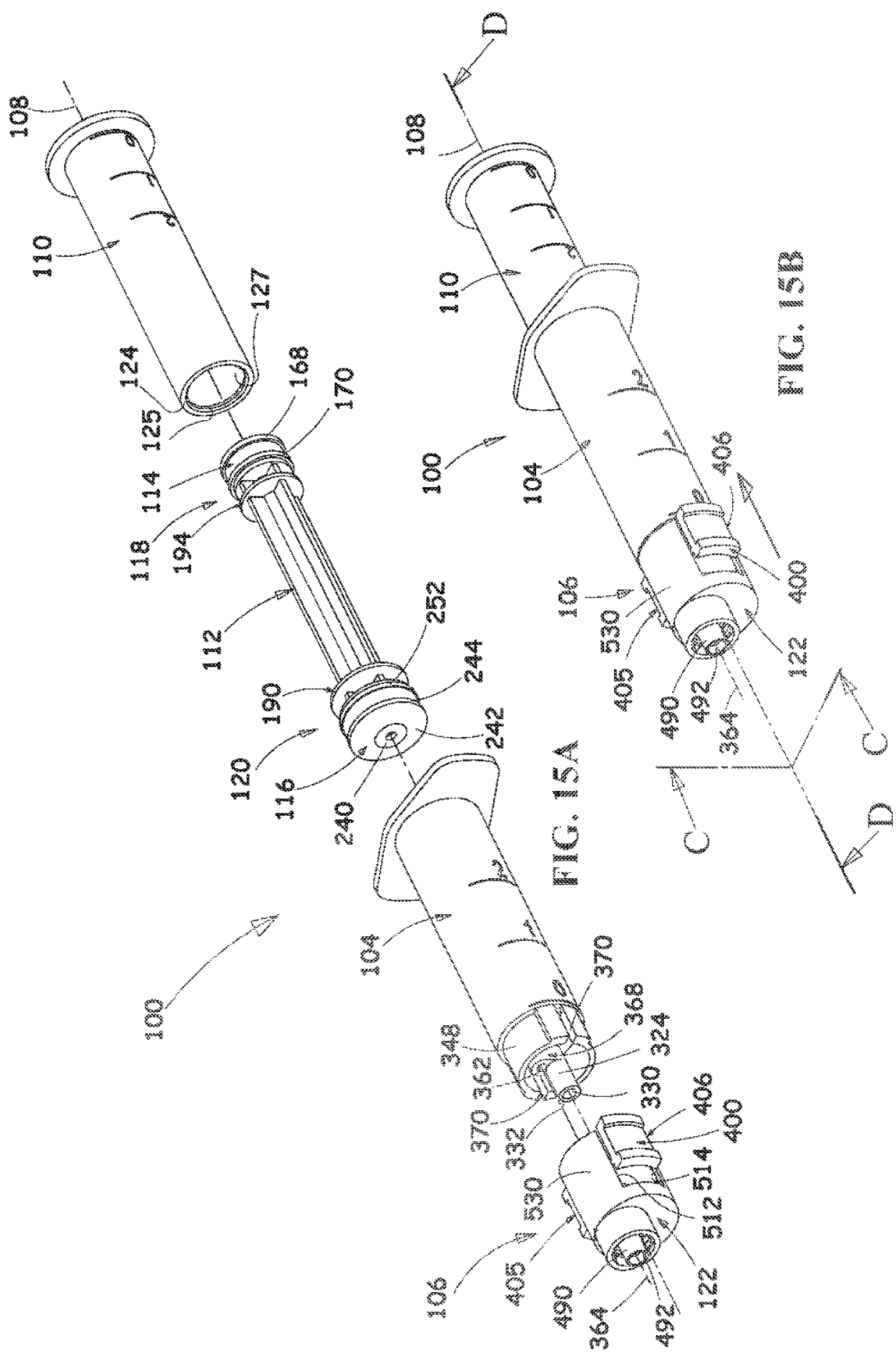

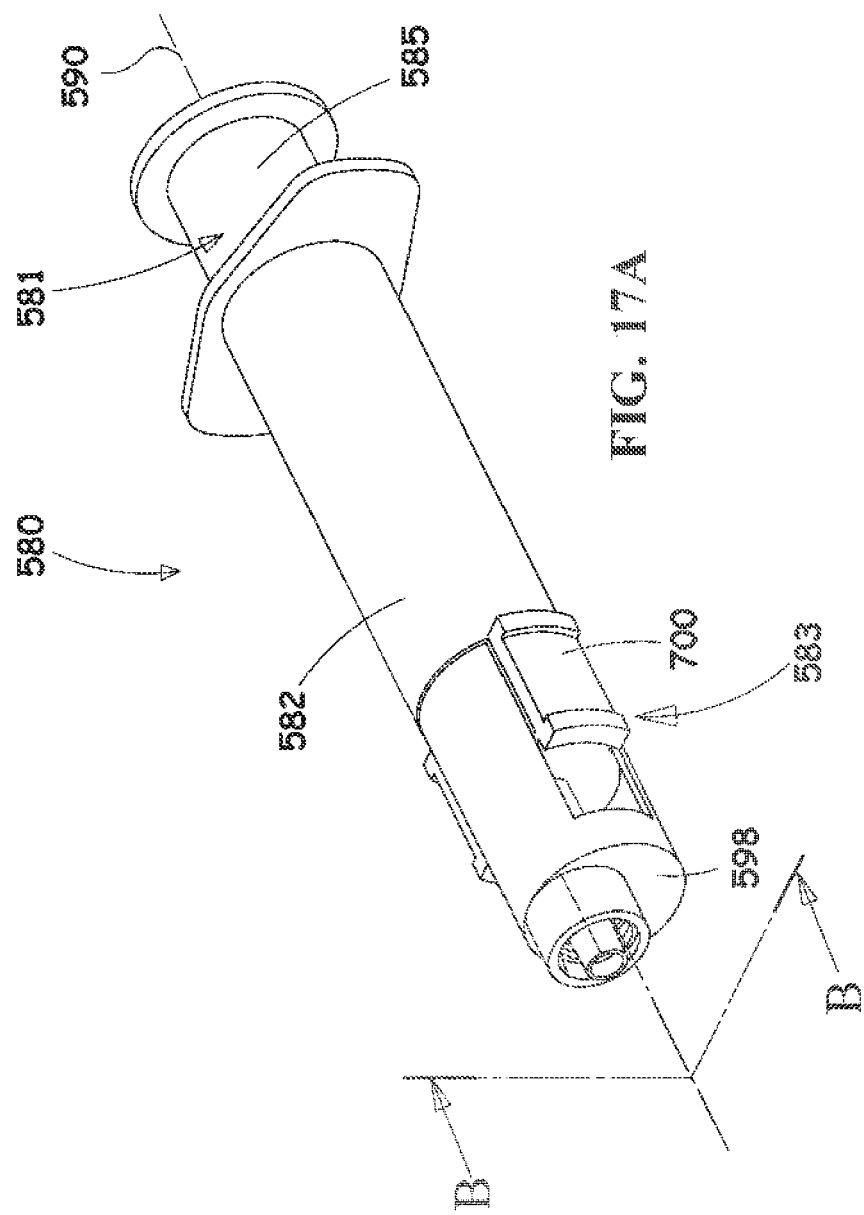

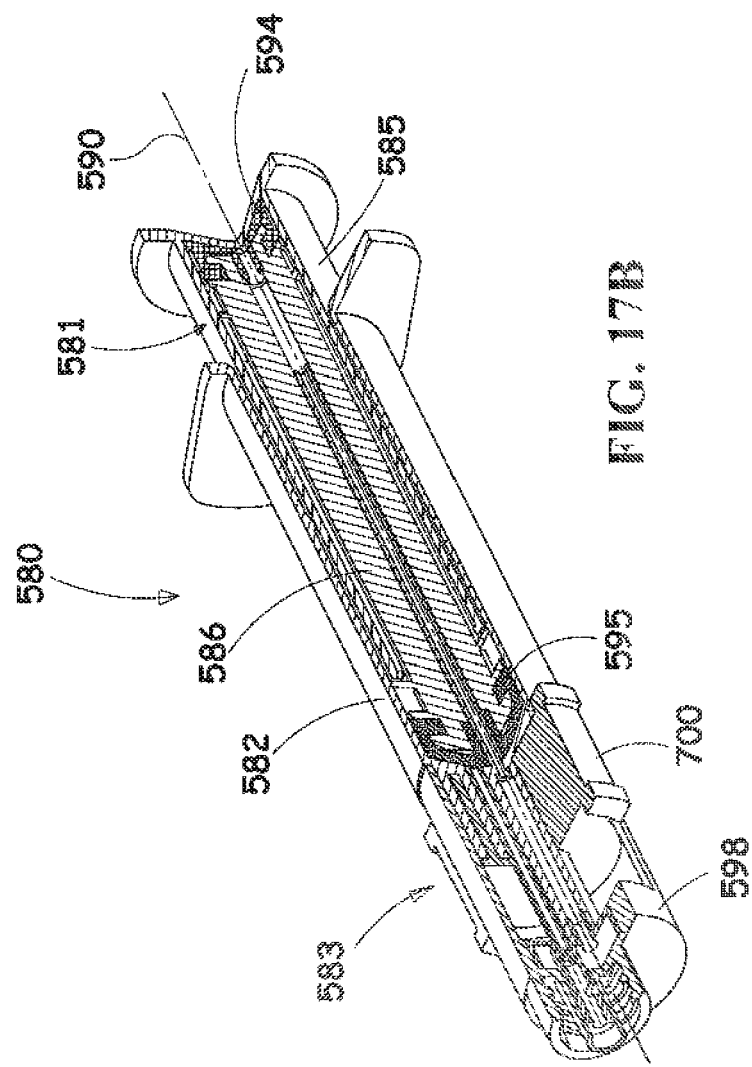

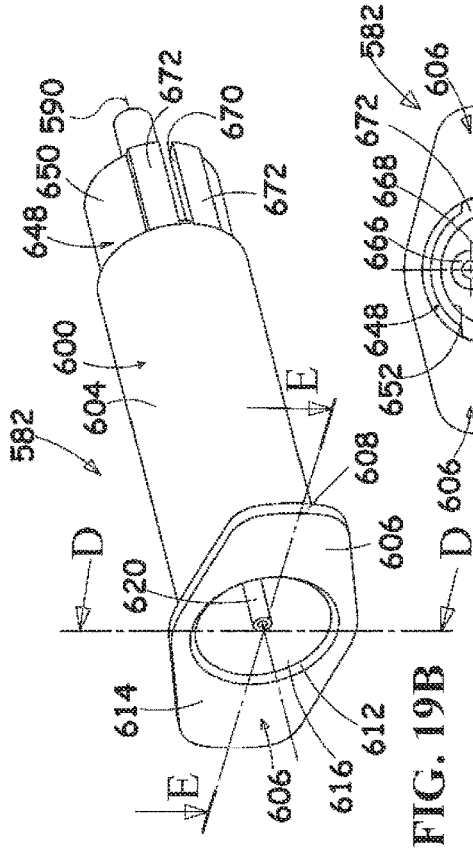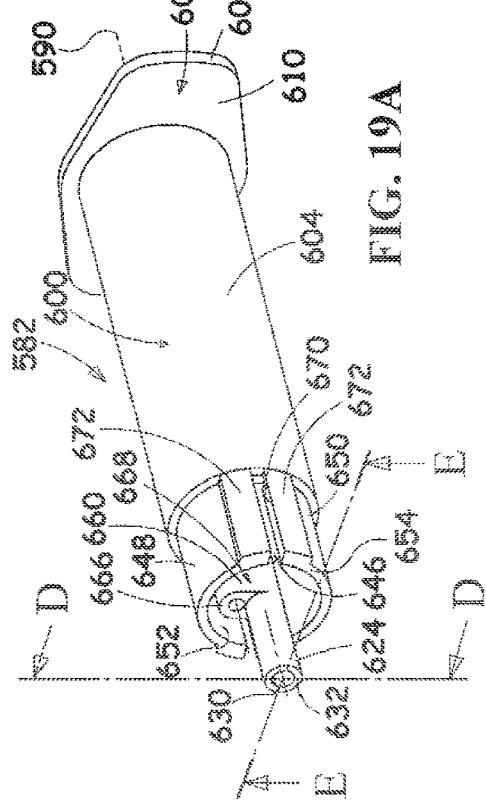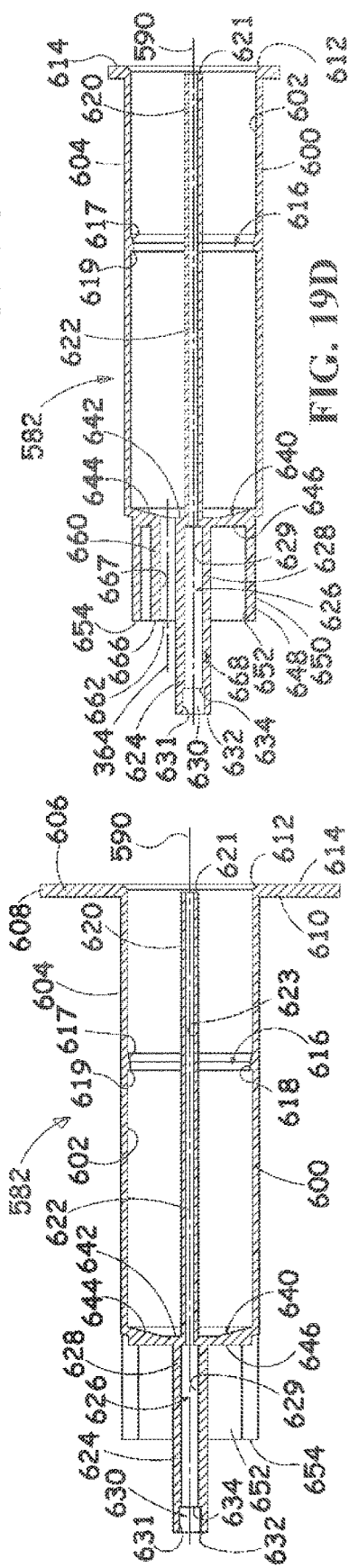

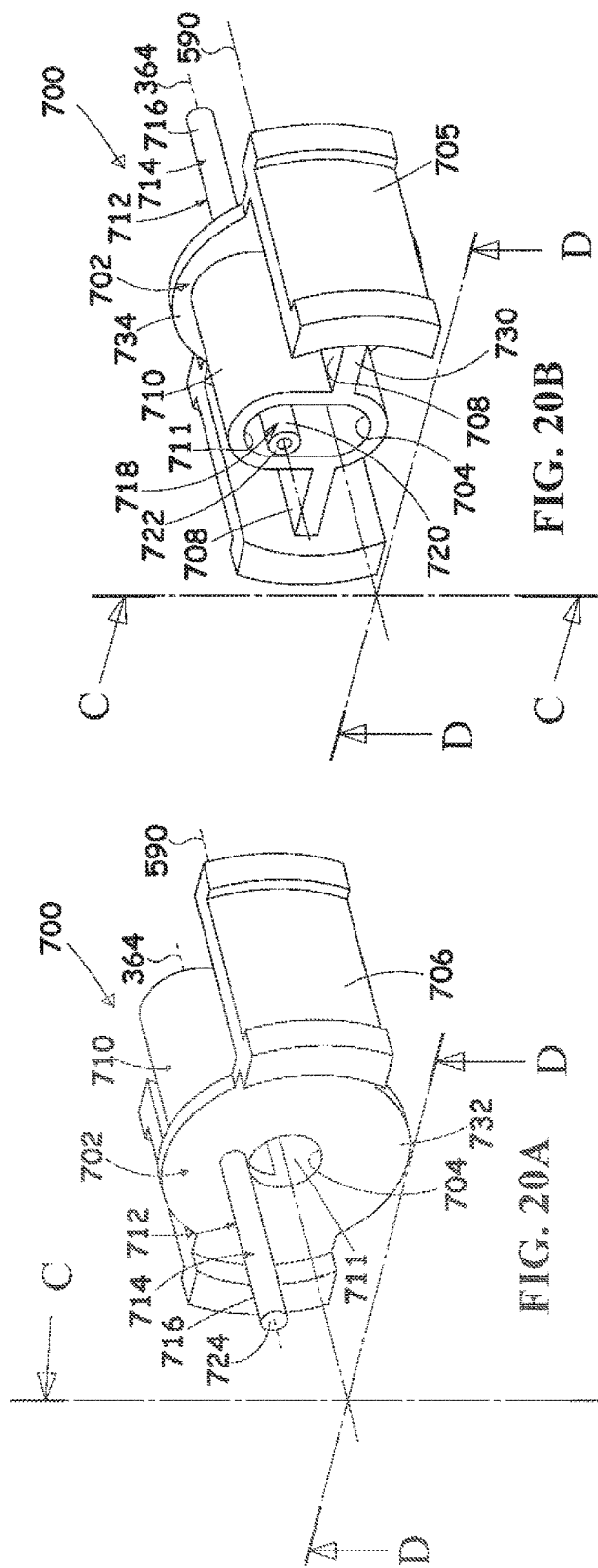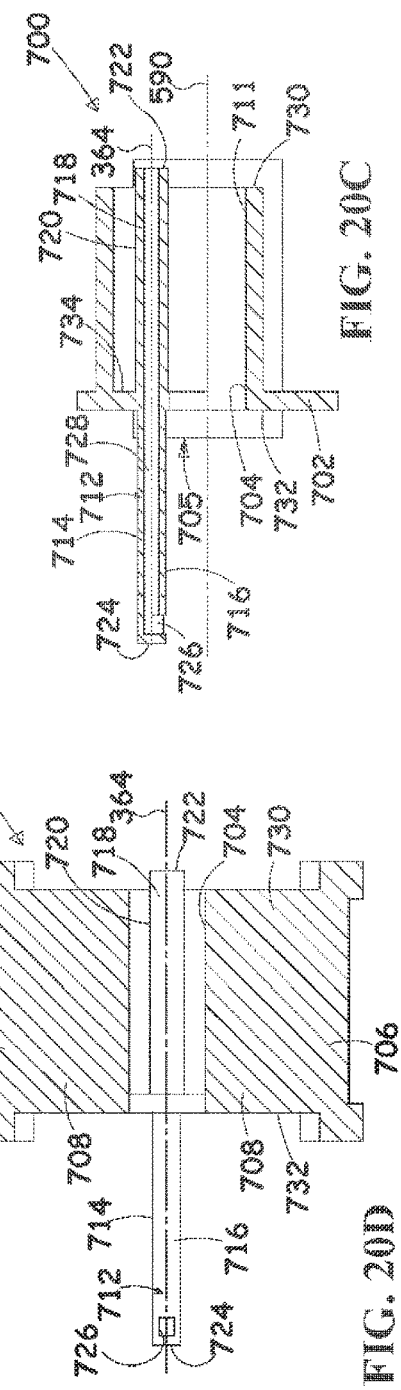
FIG. 20A
FIG. 20B
FIG. 20C
FIG. 20D

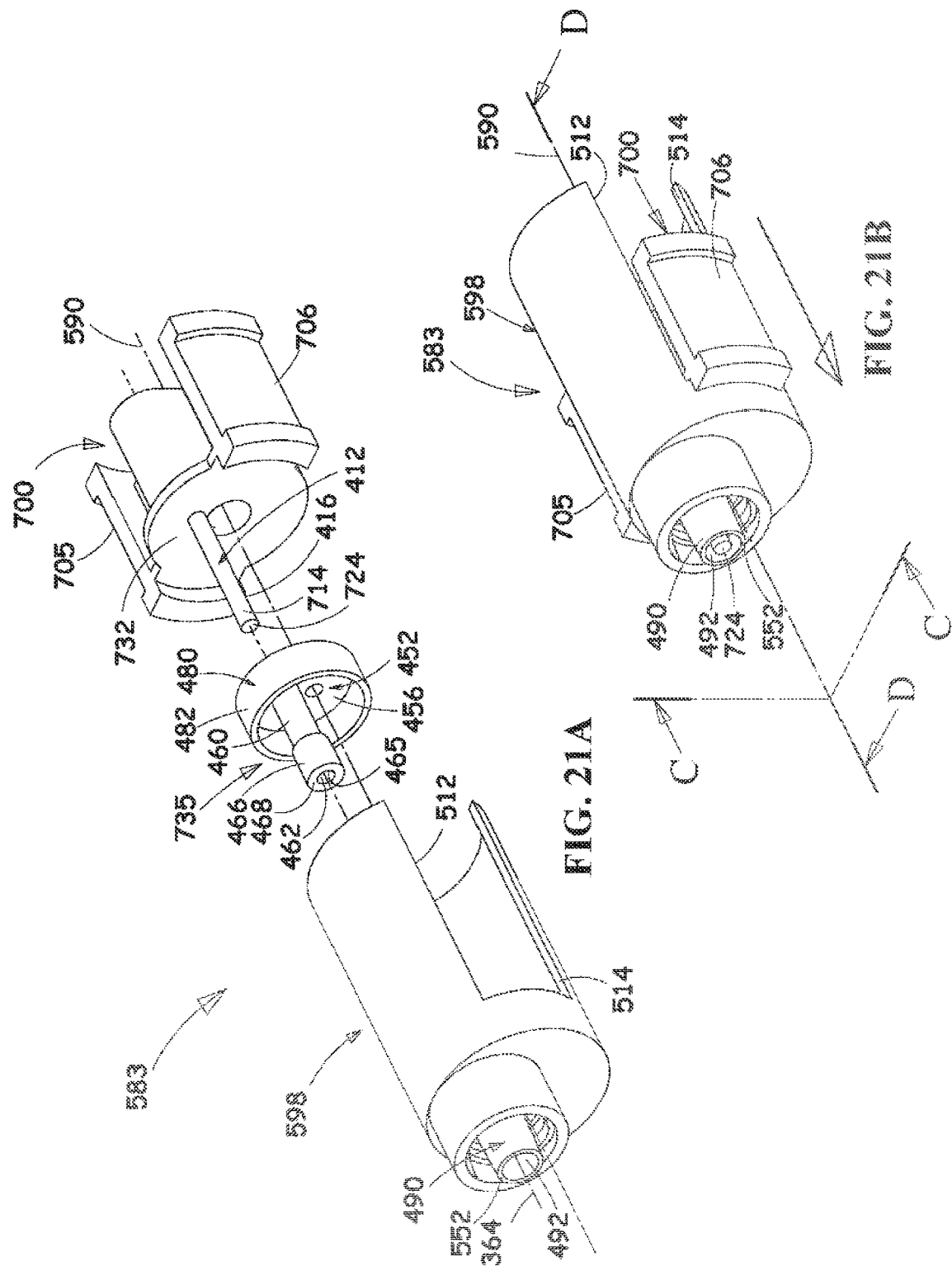

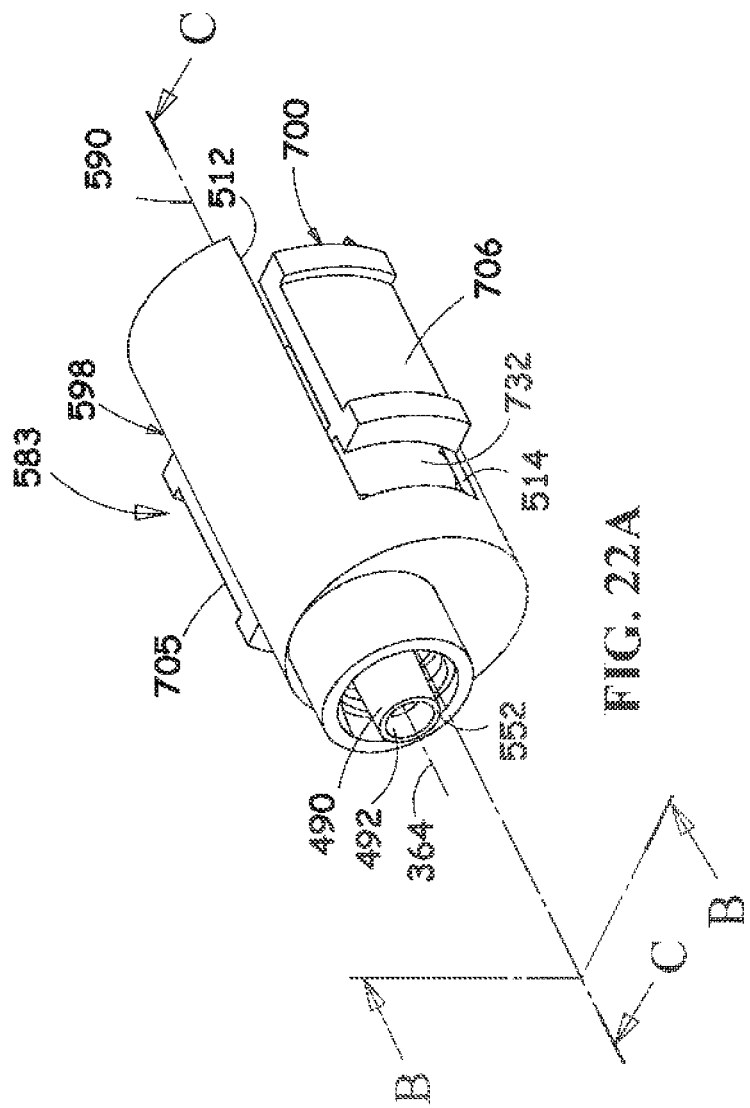

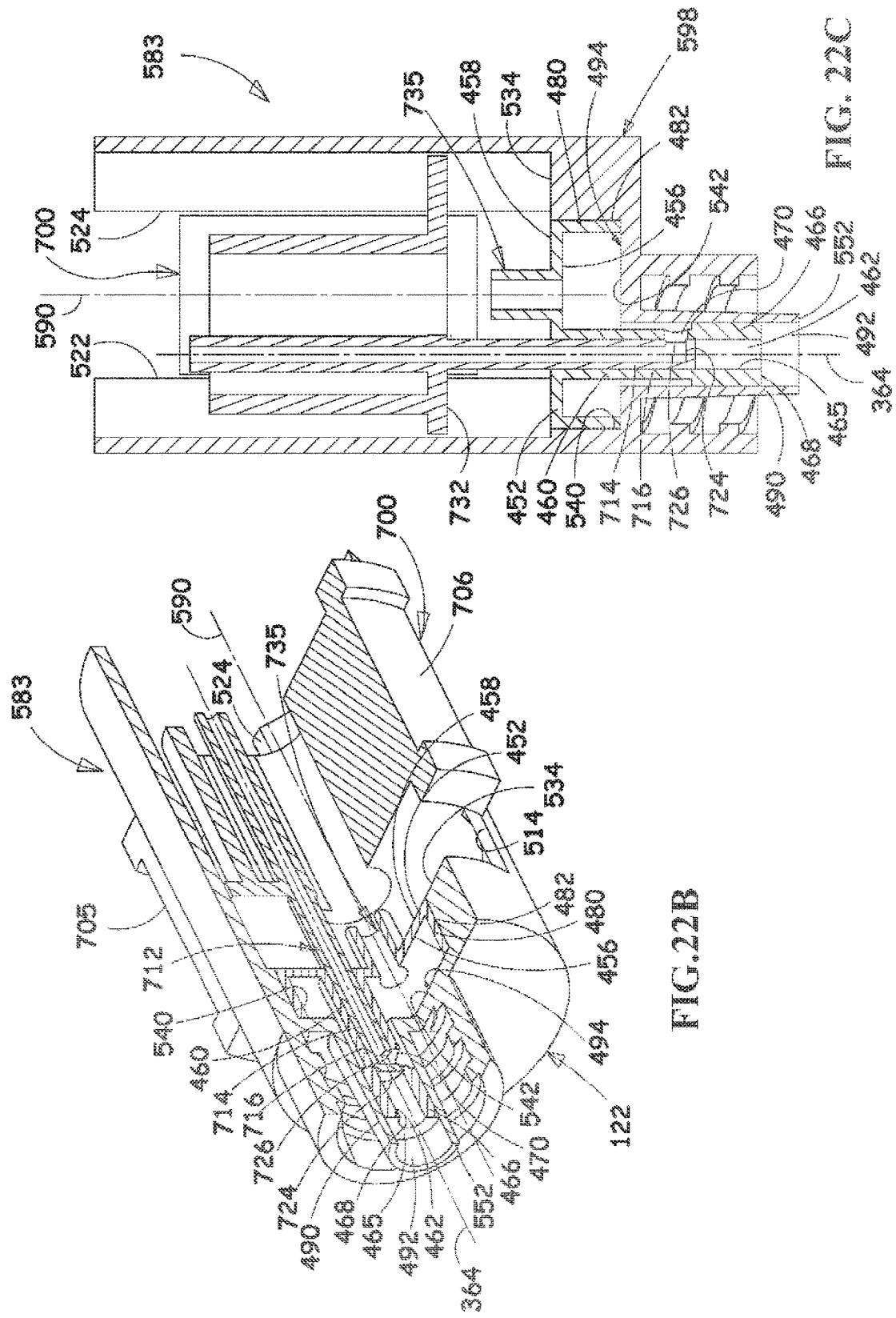

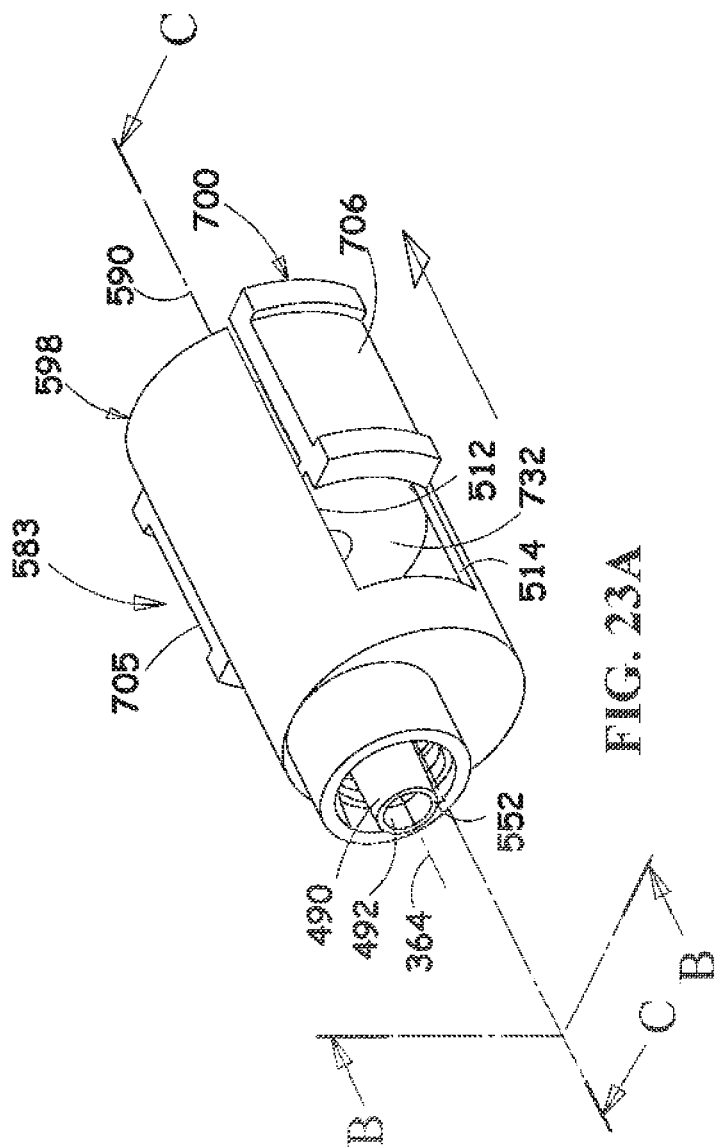

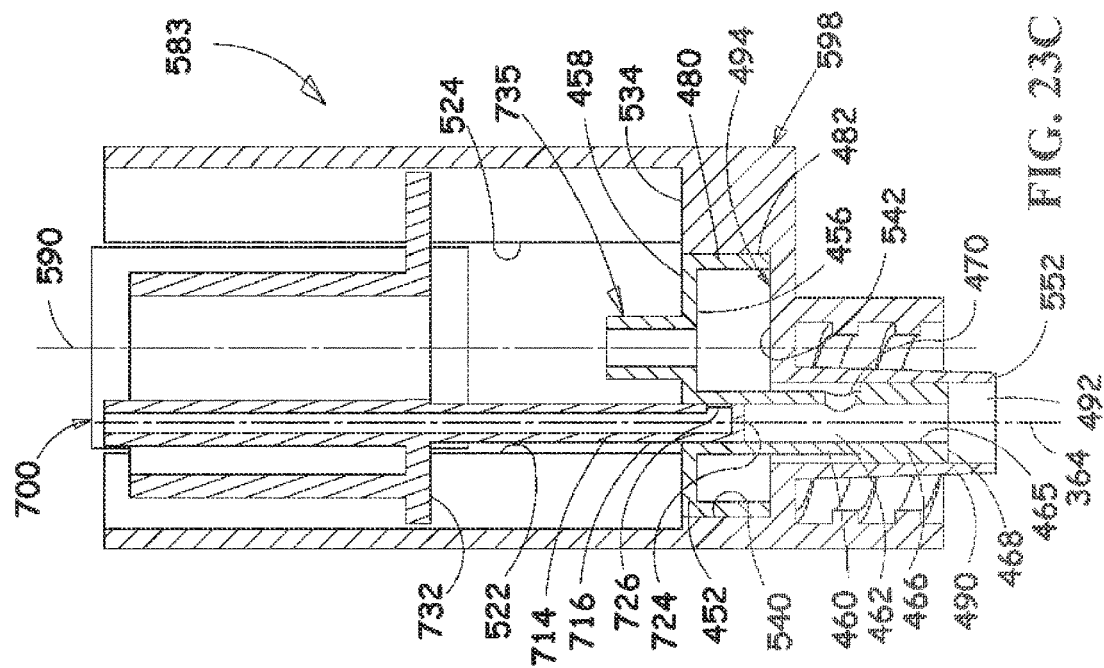
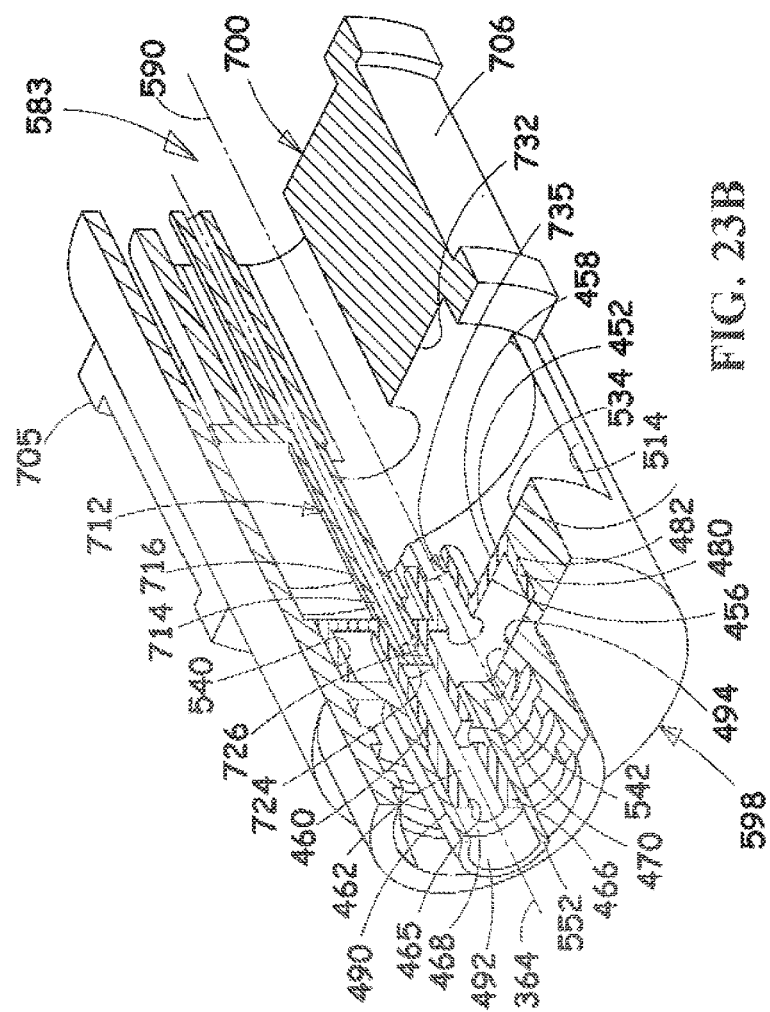
FIG. 23C
FIG. 23B

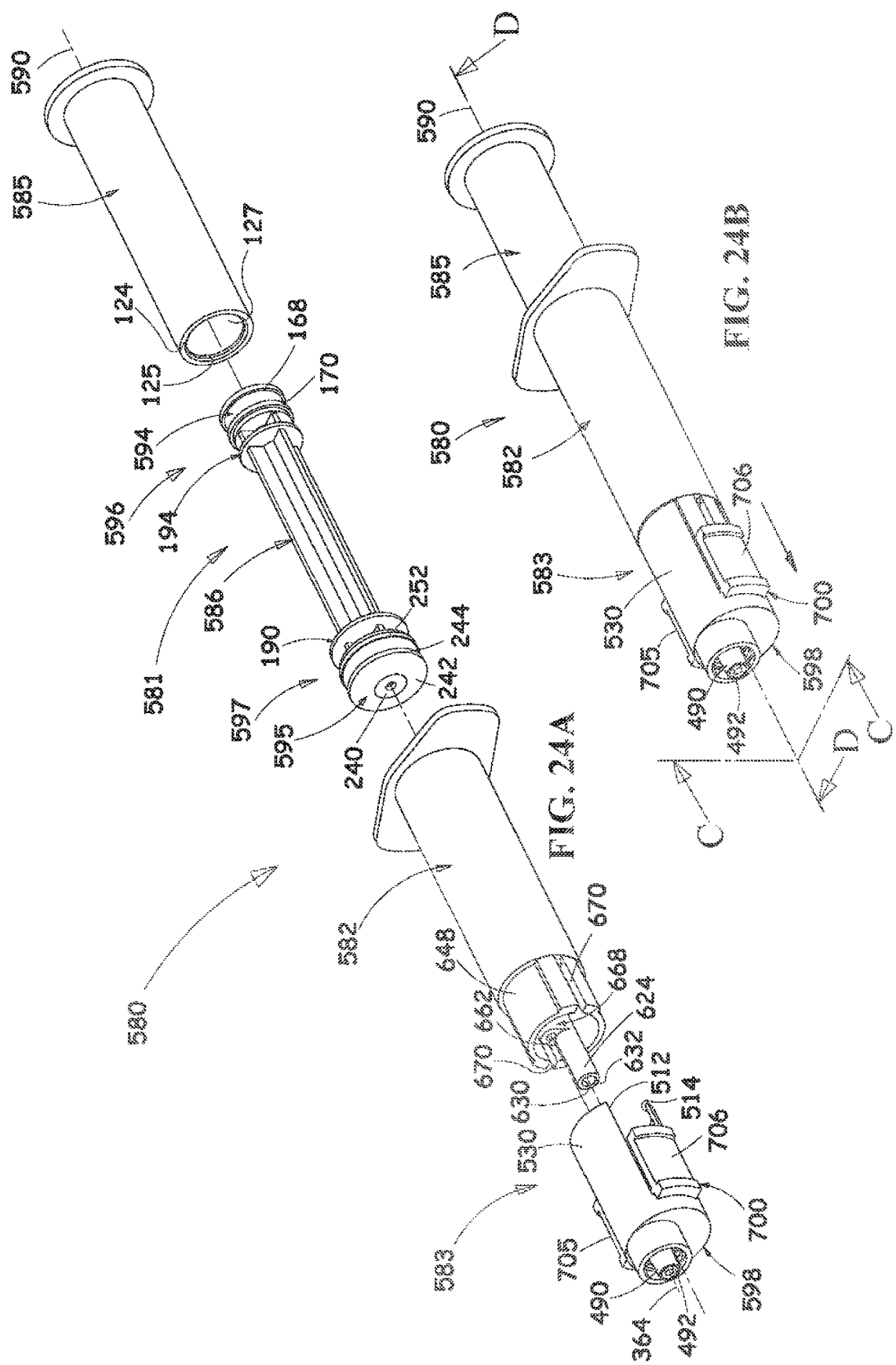

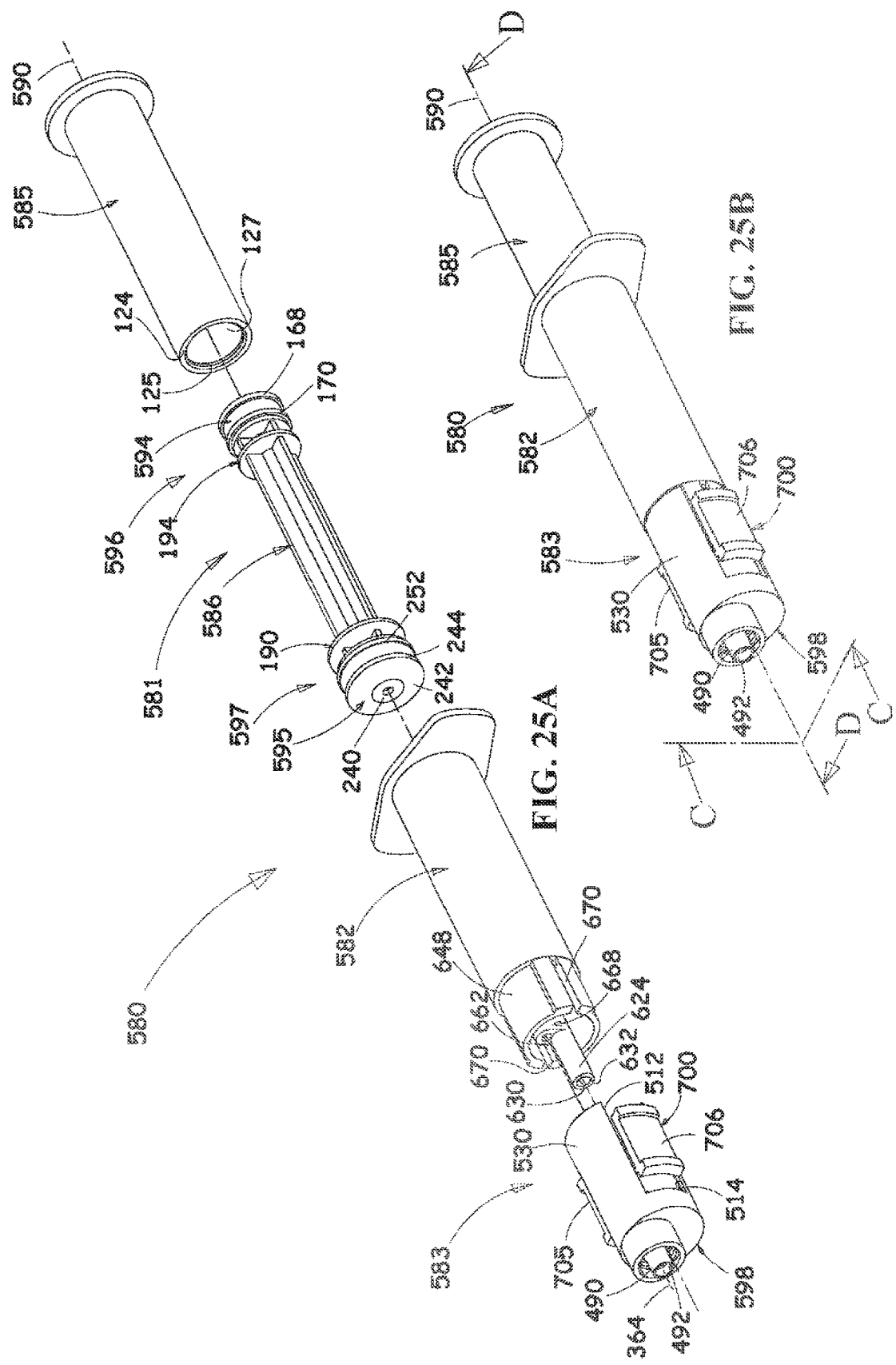

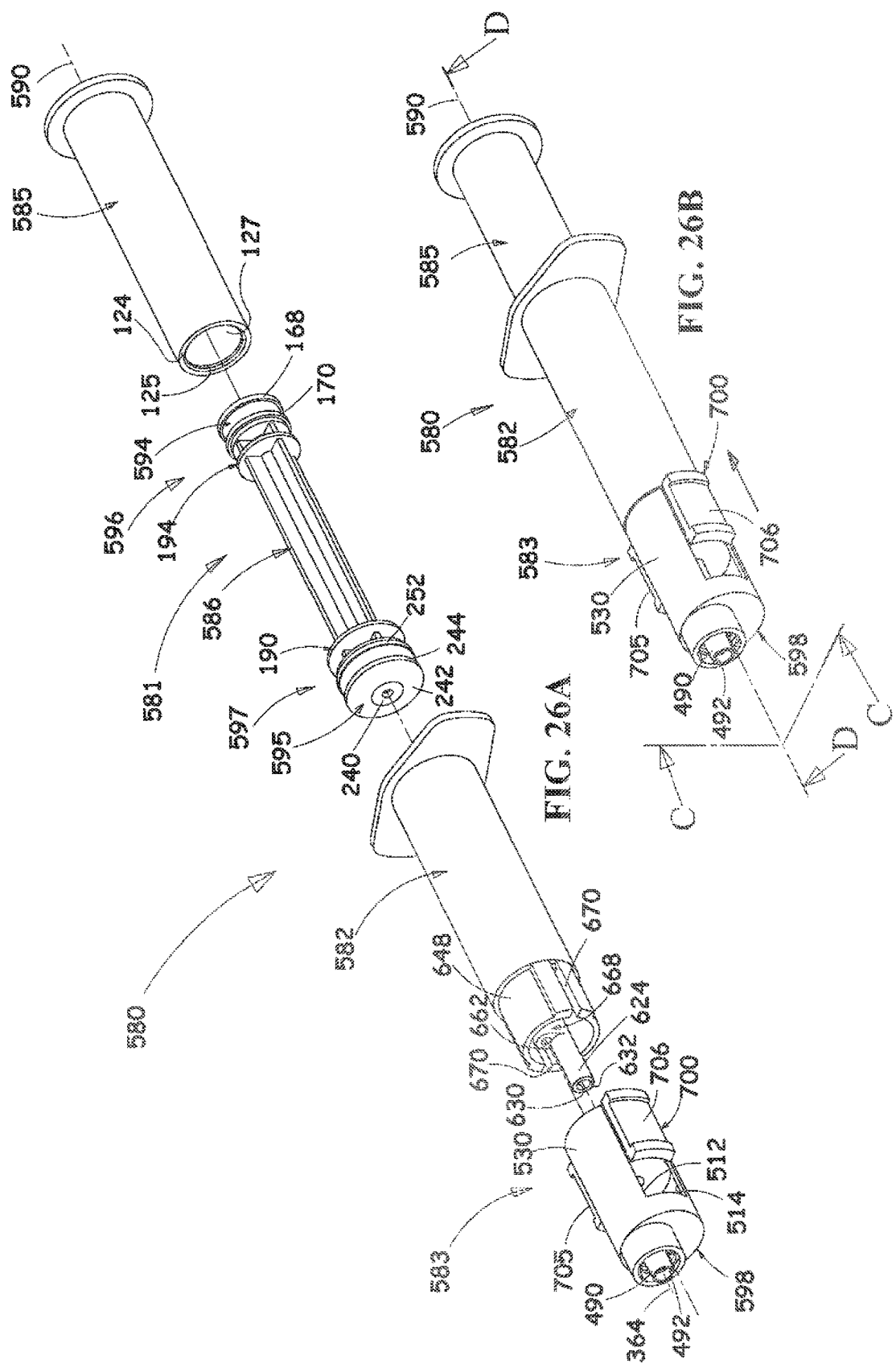

MULTI-CHAMBER SYRINGE

REFERENCE TO RELATED APPLICATIONS

Reference is made to U.S. Provisional Patent Application Ser. No. 61/713,946, filed Oct. 15, 2012 and entitled "MULTI-CHAMBER SYRINGE" and to U.S. Provisional Patent Application Ser. No. 61/835,611, filed Jun. 16, 2013 and entitled "MULTI-CHAMBER SYRINGE", the disclosures of which are hereby incorporated by reference and priority of which is hereby claimed pursuant to 37 CFR 1.78(a) (4) and (5)(i).

FIELD OF THE INVENTION

The present invention relates to syringes and more particularly multi-chamber syringes.

BACKGROUND OF THE INVENTION

Various fluid administration devices are known.

SUMMARY OF THE INVENTION

The present invention seeks to provide an improved multi-chamber syringe.

There is thus provided in accordance with a preferred embodiment of the present invention a medical fluid supply device including at least first and second fluid containers which are arranged to be mutually displaceable, at least first and second selectably openable fluid communication pathways associated with the first and second fluid containers and at least one selector switch assembly for selectably opening the first and second selectably openable fluid communication pathways, mutual displacement of the first and second fluid containers changing the amount of fluid in at least one of the at least first and second fluid containers in accordance with a state of the at least one selector switch assembly.

There is also provided in accordance with another preferred embodiment of the present invention a medical fluid supply device, including at least first and second fluid containers, at least one fluid flow passageway, at least first and second selectably openable fluid communication pathways connecting the at least first and second fluid containers with the fluid flow passageway and at least one selector switch assembly for selectably opening the first and second selectably openable fluid communication pathways in a manner that only one of the at least first and second fluid containers is connected to the at least one fluid flow passageway at any given time.

There is further provided in accordance with yet another preferred embodiment of the present invention a medical fluid supply device, including at least first and second fluid containers, the first fluid container containing a medicament and the second fluid container containing a flushing solution, a fluid flow passageway, at least first and second selectably openable fluid communication pathways connecting the at least first and second fluid containers with the fluid flow passageway and at least one selector switch assembly for selectably opening the first and second selectably openable fluid communication pathways, the at least one selector switch assembly having at least a first switch state in which only the flushing solution is in communication with the fluid flow passageway.

There is yet further provided thus provided in accordance with still another preferred embodiment of the present invention a medical fluid supply device, including at least first and second fluid containers, the first fluid container containing a medicament and the second fluid container containing a flushing solution, at least one fluid flow passageway, at least first and second selectably openable fluid communication pathways connecting the at least first and second fluid containers with the at least one fluid flow passageway and at least one selector switch assembly for selectably opening the first and second selectably openable fluid communication pathways, the at least one selector switch assembly including a luer connector and a valve assembly disposed within the luer connector, such that the valve assembly occupies a substantial portion of the volume of the luer connector.

There is even further provided in accordance with another preferred embodiment of the present invention a medical fluid supply device including at least first and second mutually displaceable fluid containers, the first fluid container being adapted to contain a medicament and the second fluid container being adapted to contain a flushing solution and at least first and second fluid communication pathways associated with the first and second fluid containers, mutual displacement of the first and second fluid containers supplying the medicament from the first fluid container and thereafter supplying the flushing solution from the second fluid container.

Preferably, the medical fluid supply device further includes a piston assembly and a barrel which are arranged for mutual telescopic displacement There is also provided in accordance with yet another preferred embodiment of the present invention a medical fluid supply device, including at least first and second fluid containers and a piston assembly and a barrel arranged for mutual telescopic displacement, the at least first and second fluid containers including a first fluid container located within the barrel and a second fluid container located within the piston assembly, a first scale indication provided on the barrel and a second scale indication provided on the piston assembly, each of the first scale indication and the second scale indication being operative to enable accurate determination of a quantity of fluid present in each of the at least first and second fluid containers.

In accordance with a preferred embodiment of the present invention the at least first and second fluid containers include a first fluid container located within the barrel and a second fluid container located within the piston assembly.

Preferably, the at least first and second fluid containers are arranged to be mutually displaceable along a common longitudinal axis and wherein mutual displacement of the first and second fluid containers along the common longitudinal axis changes the amount of fluid in at least one of the at least first and second fluid containers in accordance with a state of the at least one selector switch assembly.

Preferably, the medical fluid supply device also includes a valve assembly, which is operated by the at least one selector switch assembly for selectably opening the first and second selectably openable fluid communication pathways in response to positioning of the at least one selector switch assembly.

In accordance with a preferred embodiment of the present invention mutual displacement of the first and second fluid containers supplies the medicament from the first fluid container and thereafter supplies the flushing solution from the second fluid container, while some of the medicament remains in the first fluid container.

In accordance with a preferred embodiment of the present invention mutual displacement of the first and second fluid containers changes the amount of fluid in at least one of the at least first and second fluid containers in accordance with a state of the at least one selector switch assembly.

Preferably, the at least one selector switch assembly is manually operable for selectably opening at least one of the first and second fluid communication pathways associated with the first and second fluid containers.

In accordance with a preferred embodiment of the present invention the valve assembly is axially slidably movable within the luer connector.

Preferably, the first fluid container is adapted to contain a medicament and the second fluid container is adapted to contain a flushing solution.

In accordance with a preferred embodiment of the present invention the medical fluid supply device also includes a piston assembly and a barrel which are arranged for mutual telescopic displacement. Additionally, the at least first and second fluid containers include a first fluid container located within the barrel and a second fluid container located within the piston assembly.

In accordance with a preferred embodiment of the present invention the piston assembly includes a piston assembly housing portion and a plunger rod, which is disposed within the piston assembly housing portion and is slidable therewithin along a common longitudinal axis within predetermined axial limits. Additionally, the medical fluid supply device further includes rearward and forward piston rings, which are mounted on respective rearward and forward ends of the plunger rod for axial displacement together with the plunger rod in fluid engagement with an interior surface of the piston assembly housing portion.

In accordance with a preferred embodiment of the present invention the interior surface of the piston assembly housing portion defines part of the second fluid container. Additionally or alternatively, the selector switch assembly includes a luer connector portion for operative engagement with a medical device.

Preferably, the luer connector portion is operative for engagement with a medicament vial for enabling aspiration of medicament into the first fluid container. Additionally, the piston assembly housing portion is configured as a hollow cylinder, integrally formed at a rearward end thereof with an end plate and having an open forward end.

In accordance with a preferred embodiment of the present invention the end plate extends beyond the external surface of the piston assembly housing portion and defines a manual gripping flange. Additionally, the end plate is dimpled and defines a convex forward-facing surface defining part of the second fluid container and the rearward piston ring has a concave rearward facing surface, which matches the convex forward-facing surface of the piston assembly housing portion.

Preferably, the rearward piston ring has an axial bore extending along the longitudinal axis and communicating with the second fluid container. Additionally, the rearward piston ring includes flanges configured to provide axially displaceable sealing with the interior surface of the piston assembly housing portion.

In accordance with a preferred embodiment of the present invention the plunger rod includes a main portion, having an axial bore extending along the longitudinal axis, a rearward-facing end portion and a forward-facing end portion. Additionally, the rearward piston ring mounted on the rearward end of the plunger rod is slidably movable within the piston assembly housing portion from a first position to a second position, wherein when the rearward piston ring is in the first position, the end plate of the piston assembly housing portion engages the rearward-facing end of the rearward piston ring and when the rearward piston ring is in the second position, rearward-end portion of the plunger rod engages an inwardly directed flange formed adjacent an open end of the piston assembly housing portion. Additionally or alternatively, the rearward-facing end portion and the forward-facing end portion have bores which communicate with the axial bore.

Preferably, the forward piston ring includes a cylindrical portion defining an axial bore extending along the longitudinal axis and communicating with the second fluid container. Additionally, the forward piston ring is formed with a flat forward surface and a tapered ring surface extending radially outwardly and rearward from the flat forward surface.

In accordance with a preferred embodiment of the present invention the barrel is arranged along a common longitudinal axis and includes a cylindrical chamber having an inner and outer surface, wherein the inner surface forms part of the first fluid container. Additionally, the medical fluid supply device also includes an internal channel member extending along the radial center of the cylindrical chamber and defining a thoroughgoing internal bore.

Preferably, the internal channel member of the barrel is sealingly slidably arranged within the cylindrical portion of the forward piston ring due to engagement of the internal channel member with inwardly facing surfaces formed on the cylindrical portion of the forward piston ring. Additionally the medical fluid supply device further includes a forward channel portion arranged along the longitudinal axis and integrally formed with the cylindrical chamber and wherein an interior of the forward channel portion communicates with the thoroughgoing internal bore.

In accordance with a preferred embodiment of the present invention the inner surface terminates at a forward end of the cylindrical chamber in a bulkhead having a central flat surface surrounding the internal channel member and a radially outward tapered surface.

Preferably, the forward piston ring mounted on the forward end of the plunger rod is slidably movable within the barrel from a first position to a second position, wherein when the forward piston ring is in the first position, the central flat surface and the radially outward tapered surface of the barrel engage the corresponding flat forward surface and tapered ring surface of the forward piston ring and when the forward piston ring is in the second position, the forward-end portion of the plunger rod engages an inwardly directed flange formed adjacent a rearward end of the barrel.

Preferably, when the forward piston ring and the rearward piston ring are both positioned in the first position, the piston assembly housing portion is partially inserted into the barrel. Additionally or alternatively, when the forward piston ring and the rearward piston ring are both positioned in the second position, the forward end of the piston assembly housing portion is rearwardly spaced apart from the rearward end of the barrel.

In accordance with a preferred embodiment of the present invention the barrel also includes an additional channel portion extending forwardly from the bulkhead and including a bore arranged along an axis parallel to the longitudinal axis and extending through the bulkhead, wherein the bore communicates with the first fluid container. Additionally, the central flat surface surrounding the internal channel member and the radially outward tapered surface match the flat forward surface and the tapered ring surface of the forward piston ring.

Preferably, the forward piston ring includes flanges configured to provide axially displaceable sealing with the inner surface of the barrel.

In accordance with a preferred embodiment of the present invention the medical fluid supply device also includes an axially displaceable element which is selectably positionable along the longitudinal axis in at least a first state and a second state relative to the luer connector portion. Additionally, the axially displaceable element includes an apertured disc portion and a cannula portion extending forwardly and rearwardly of the disc portion and having inner and outer cylindrical surfaces, an open rearward end and a closed forward end. Preferably, the cannula portion has a side aperture adjacent the forward end, which side aperture is directed in a direction opposite to a direction facing the longitudinal axis. Additionally, the cannula portion is formed with an axial bore extending from the rearward end to the side aperture.

In accordance with a preferred embodiment of the present invention the barrel also includes also including a static element including a disc portion and arranged along an axis that is parallel to the longitudinal axis. Additionally, the static element includes a forward flow channel portion, extending forwardly from the disc portion and having an outer surface and an inner surface, and a bore, the forward flow channel portion having a thickened forward portion which defines a rearwardly facing shoulder.

Preferably, the static element also includes a side opening formed in the forward flow channel portion, the side opening facing in a direction toward the longitudinal axis. Additionally, the static element also includes a rearward flow channel portion having inner and outer surfaces extending rearwardly from the disc portion and defining a bore that communicates with the second fluid container.

In accordance with a preferred embodiment of the present invention the luer connector portion includes a flow channel having a bore and the forward flow channel portion of the static element is at least partially inserted into the flow channel of the luer connector portion, such that the thickened forward portion of the static element is fluid sealingly arranged within the bore of the flow channel of the luer connector portion.

Preferably, the cannula portion of the axially displaceable element is slidably fluid sealingly engaged with the inner surface of the forward flow channel of the static element. Additionally or alternatively, the side opening of the forward flow channel of the static element and the aperture of the cannula portion of the axially displaceable element face in mutually opposite directions. Additionally or alternatively, the side opening of the forward flow channel of the static element and the aperture of the cannula portion of the axially displaceable element face in the same direction.

In accordance with a preferred embodiment of the present invention when the axially displaceable element is selectably positioned in the first state, the side opening of the forward flow channel portion of the static element is sealed closed by fluid sealing engagement of the outer cylindrical surface of the cannula portion with the inner surface of the forward flow channel portion of the static element.

Preferably, when the axially displaceable element is selectably positioned in the second state, the forward end of the cannula portion is positioned rearwardly of the side opening of the forward flow channel portion of the static element, such that the side opening is open.

In accordance with a preferred embodiment of the present invention when the axially displaceable element is selectably positioned in the first state, the forward end of the cannula portion is positioned forwardly of a forward edge of the forward flow channel portion of the static element, such that the aperture of the cannula portion is open. Additionally or alternatively, when the axially displaceable element is selectably positioned in the second state, the aperture of the cannula portion of the axially displaceable element is closed by fluid sealing engagement of outer surface of the cannula portion with the inner surface of the forward flow channel portion of the static element.

In accordance with a preferred embodiment of the present invention the rearward flow channel portion of the static element is inserted into the forward flow channel portion of the barrel such that the outer surface of the rearward flow channel portion fluid sealingly engages the inner surface of the forward flow channel of the barrel.

Preferably, a rearward portion of the cannula portion of the axially displaceable element is at least partially inserted into the additional channel portion of the barrel in a slidably fluid sealing manner.

In accordance with a preferred embodiment of the present invention the first fluid communication pathway is defined by the inner surface of the chamber of the barrel, an outer surface of the internal channel member, the central flat surface and the radially outward tapered surface of the barrel, the flat forward surface and tapered ring surface of the forward piston ring, the inner surface of the forward flow channel portion of the barrel, the rearward end of the cannula portion, the aperture and the bore of the cannula portion.

Preferably, when the axially displaceable element is selectably positioned in the first state, the first fluid communication pathway is in open communication with an outlet defined by an inner surface of the flow channel of the luer connector portion.

In accordance with a preferred embodiment of the present invention the second fluid communication pathway is defined by the inner surface of the forward flow channel portion of the static element, the side opening of the forward flow channel portion, the rearwardly facing shoulder of the thickened portion of the forward flow channel portion, the outer surface of the forward flow channel portion, rearward flow channel portion of the static element, the forward end of the cannula portion of the axially displaceable element, the inner surface of the forward flow channel member of the barrel, the bore of the inner channel member of the barrel, the bore of the plunger rod, the bore of the rearward piston, the interior surface of the piston assembly housing portion and the end plate of the piston assembly housing portion.

In accordance with a preferred embodiment of the present invention when the axially displaceable element is selectably positioned in the first state, the second fluid communication pathway is sealed by closing of the side opening of the static element produced by sealing engagement of the outer surface of the cannula portion with the inner surface of the forward flow channel portion of the static element.

In accordance with a preferred embodiment of the present invention when the axially displaceable element is selectably positioned in the second state, the first fluid communication pathway is sealed from the outlet defined by an inner surface of the flow channel of the luer connector portion by virtue of the fact that the aperture of the cannula portion of the axially displaceable element is closed by engagement of outer surface of the cannula portion with the inner surface of the forward flow channel portion of the static element.

In accordance with a preferred embodiment of the present invention when the axially displaceable element is selectably positioned in the second state, the second fluid communication pathway is in open communication with the outlet defined by the inner surface of the flow channel of the luer connector portion by virtue of the fact that the forward end of the cannula portion is positioned rearwardly of the side opening of the forward flow channel portion of the static element, thereby causing the side opening to be open.

Preferably, when the axially displaceable element is selectably positioned in the first state, the rearward piston ring mounted on the rearward end of the plunger rod remains in a fixed position relative to the piston assembly housing portion due to negative pressure produced in the second fluid communication pathway following retraction of the piston assembly.

In accordance with a preferred embodiment of the present invention a medicament is sealingly retained in the first fluid communication pathway and does not remain in the outlet defined by an inner surface of the flow channel of the luer connector portion.

Preferably, when the axially displaceable element is selectably positioned in the first state, the rearward piston ring mounted on the rearward end of the plunger rod remains in a fixed position relative to the piston assembly housing portion due to positive pressure produced in the second fluid communication pathway by forward directed pressure exerted on the piston assembly.

In accordance with a preferred embodiment of the present invention the axially displaceable element is selectably positionable in a first state, an intermediate state and a second state relative to the luer connector portion.

Preferably, when the axially displaceable element is selectably positioned in the intermediate state, the forward end of the cannula portion is positioned forwardly of the side opening of the static element, such that the aperture of the cannula portion is open to the side opening of the static element. Preferably, when the axially displaceable element is selectably positioned in the intermediate state, fluid sealing engagement is provided between the inner surface of the forward flow channel portion of the static element and the outer surface of the cannula portion. Additionally, when the axially displaceable element is selectably positioned in the intermediate state, the first fluid communication pathway is in open communication with the second communication pathway for reconstitution of a medicament with a flushing solution.

In accordance with a preferred embodiment of the present invention when the axially displaceable element is selectably positioned in the intermediate state, the first fluid communication pathway is sealed from the outlet by virtue of a sealing engagement between the outer surface of the cannula portion and the inner surface of the forward flow channel portion of the static element. Additionally, when the axially displaceable element is selectably positioned in the intermediate state, there is an open communication between the first fluid container and the second fluid container via the flow channel of the luer connector portion, outer surface of the forward flow channel portion of the static element, the rearwardly facing shoulder and the side opening of the static element and via the aperture of the cannula portion.

Preferably, the first fluid container is adapted to contain a reconstitutable medicament and the second fluid container is adapted to contain a reconstitution and flushing solution. Additionally, the reconstitutable medicament is located within the barrel, within a reconstitutable medicament volume delimited by the forward flat surface and tapered ring surface of the forward piston ring and between the inner surface of the barrel, the central flat surface and radially outward tapered surface of the barrel and the internal channel member of the barrel. Preferably, the reconstitution and flushing solution is located within the piston assembly housing portion within a reconstitution and flushing solution initial volume delimited by the end plate and the inner surface of the piston assembly housing portion, the recess and the cylindrical portion of the rearward piston ring, the inner surface of the bore of the plunger rod, the inner surface of the bore of the internal channel member of the barrel, the inner surface of the bore of the forward flow channel portion of the barrel, the inner surface of the rearward channel portion of the static element, the rearward facing shoulder, the outer surface and the side opening of the forward channel portion of the static element, the forward end of the cannula portion, inner surface of the bore of the forward flow channel portion of the static element.

In accordance with a preferred embodiment of the present invention when the axially displaceable element is selectably positioned in the intermediate state and the piston assembly housing portion is displaced forwardly, the plunger rod is urged to be displaced rearwardly relative to the barrel, due to the fact that the total cross sectional area of the forward piston ring is substantially larger than the total cross sectional of the rearward piston ring, thus causing a greater first force to be exerted rearwardly on the forward piston than a second force exerted forwardly on the rearward piston ring. Additionally, the plunger rod also includes an inwardly facing plunger rod rearward motion limiting flange extending inwardly from the inner surface of the barrel, the location of the flange along the inner surface defining a medicament concentration. Additionally, the rearward displacement of the plunger rod is limited by engagement of the inwardly facing plunger rod rearward motion limiting flange of the plunger rod with the flange of the barrel, thereby limiting the amount of the reconstitution and flushing solution which is employed in reconstituting the reconstitutable medicament.

Preferably, the rearward displacement of the plunger rod occurs as the result of flow of the reconstitution and flushing solution from the reconstitution and flushing solution initial volume via the bore of the rearward piston ring, the bore of the plunger rod, the bore of the interior channel member of the barrel, the bore of the forward flow channel member of the barrel, the bore of the rearward flow channel portion of the static element, the side opening of the static element, the aperture of the cannula portion, the bore of the rearward flow channel portion of the static element and the bore of the cannula portion into the reconstitutable medicament volume.

There is also provided in accordance with yet another preferred embodiment of the present invention a medical fluid supply method including providing first and second mutually displaceable fluid containers, the first fluid container containing a medicament and the second fluid container containing a flushing solution, and at least first and second fluid communication pathways associated with the first and second fluid containers and mutually displacing the first and second fluid containers, thereby to supply medicament from the first fluid container and thereafter to supply the flushing solution from the second fluid container.

There is further provided in accordance with still another preferred embodiment of the present invention a medical fluid supply method including providing first and second mutually displaceable fluid containers, the first fluid container containing a medicament and the second fluid container containing a flushing solution, providing at least first and second selectably openable fluid communication pathways associated with the first and second fluid containers, providing at least one selector switch assembly, having a luer connector portion and a valve assembly disposed within the luer connector portion, for selectably opening the first and second selectably openable fluid communication pathways, initially positioning the selector switch assembly to a first orientation to provide flow of the medicament through the luer connector portion and repositioning the selector switch assembly to a second orientation to provide flow of the flushing solution through the luer connector portion, thereby wiping a residual amount of the medicament from the luer connector portion and sealing the medicament in the first fluid container.

There is even further provided in accordance with still another preferred embodiment of the present invention a medical fluid supply method including providing first and second mutually displaceable fluid containers, a plunger rod disposed partially within the first fluid container and the second fluid container, at least first and second fluid communication pathways associated with the first and second fluid containers and a selector switch assembly operative for selectably opening one of the at least first and second fluid communication pathways, positioning the selector switch assembly in one of its states and mutually displacing the first and second fluid containers, thereby causing the plunger rod to remain in a fixed position relative to one of the first and second containers.

There is still further provided in accordance with another preferred embodiment of the present invention a medical fluid supply method including providing first and second mutually displaceable fluid containers, a plunger rod disposed partially within the first fluid container and the second fluid container, at least first and second fluid communication pathways associated with the first and second fluid containers and a selector switch assembly operative for selectably opening one of the at least first and second fluid communication pathways, positioning the selector switch assembly in an intermediate state and mutually displacing the first and second fluid containers, thereby causing the plunger rod to be displaced rearwardly relative to the first and second fluid containers.

BRIEF DESCRIPTION OF THE DRAWINGS

The present invention will be understood and appreciated more fully from the following detailed description, taken in conjunction with the drawings in which:

FIG. 1A is a simplified pictorial illustration of a multi-chamber syringe constructed and operative in accordance with an embodiment of the invention;

FIG. 2A is a simplified exploded view illustration of the multi-chamber syringe of FIG. 1A;

FIG. 3A is a simplified pictorial illustration of a piston assembly housing portion of the multi-chamber syringe of FIGS. 1A-2B;

FIG. 3B is a simplified sectional view of the piston assembly housing portion, the sectional view being taken along lines B-B of FIG. 3A;

FIG. 4A is a simplified pictorial illustration of a rearward piston of the multi-chamber syringe of FIGS. 1A-2B, showing the rearward piston from the forward end;

FIG. 4B is a simplified pictorial illustration of the rearward piston of the multi-chamber syringe of FIGS. 1A-2B, showing the rearward piston from the rearward end;

FIG. 4C is a simplified sectional view of the rearward piston, the sectional view being taken along lines C-C of FIGS. 4A & 4B;

FIG. 6A is a simplified pictorial illustration of a forward piston of the multi-chamber syringe of FIGS. 1A-2B, showing the forward piston from the rearward end;

FIG. 6B is a simplified pictorial illustration of the forward piston of the multi-chamber syringe of FIGS. 1A-2B, showing the rearward piston from the forward end;

FIG. 6C is a simplified sectional view of the forward piston, the sectional view being taken along lines C-C of FIGS. 6A & 6B;

FIG. 7A is a simplified pictorial illustration of a barrel of the multi-chamber syringe of FIGS. 1A-2B, showing the barrel from the forward end;

FIG. 7B is a simplified pictorial illustration of the barrel of the multi-chamber syringe of FIGS. 1A-2B, showing the barrel from the rearward end;

FIG. 7C is a simplified view of the forward end of the barrel;

FIG. 7D is a sectional view of the barrel, this sectional view being taken along lines D-D of FIGS. 7A & 7B;

FIG. 7E is a simplified sectional view of the barrel, this sectional view being taken along lines E-E of FIGS. 7A & 7B, generally perpendicular to lines D-D;

FIG. 8A is a simplified pictorial illustration of an axially displaceable element of the multi-chamber syringe of FIGS. 1A-2B, showing the axially displaceable element from a forward end;

FIG. 8B is a simplified pictorial illustration of the axially displaceable element of the multi-chamber syringe of FIGS. 1A-2B, showing the axially displaceable element from a rearward end;

FIG. 8C is a simplified sectional view of the axially displaceable element, the sectional view being taken along lines C-C of FIGS. 8A & 8B;

FIG. 8D is a simplified sectional view of the axially displaceable element, the sectional view is taken along lines D-D of FIGS. 8A & 8B, generally perpendicular to lines C-C;

FIG. 9A is a simplified pictorial illustration of a static element of the multi-chamber syringe of FIGS. 1A-2B, showing the static element from a rearward end;

FIG. 9B is a simplified pictorial illustration of the static element of the multi-chamber syringe of FIGS. 1A-2B, showing the static element from a forward end;

FIG. 9C is a simplified sectional view of the static element, the section view being taken along lines C-C of FIGS. 9A & 9B;

FIG. 9D is a simplified sectional view of the static element, the section view being taken along lines D-D of FIGS. 9A & 9B, generally perpendicular to lines I-I;

FIG. 10A is a simplified pictorial illustration of a luer connector portion of the multi-chamber syringe of FIGS. 1A-2B, showing the luer connector portion from a rearward end;

FIG. 10B is a simplified pictorial illustration of the luer connector portion of the multi-chamber syringe of FIGS. 1A-2B, showing the luer connector portion from a forward end;

FIG. 10C is a simplified sectional view of the luer connector portion, the sectional view being taken along lines C-C of FIGS. 10A & 10B;

FIG. 10D is a simplified sectional view of the luer connector portion, the sectional view being taken along lines D-D of FIGS. 10A & 10B, generally perpendicular to lines C-C;

FIG. 11A is a simplified exploded view illustration of a plunger sub-assembly of the multi-chamber syringe of FIGS. 1A-2B;

FIG. 11B is a simplified pictorial illustration of the plunger sub-assembly of FIG. 11A;

FIG. 11C is a simplified cut-away view illustration of the plunger sub-assembly of FIG. 11B, along with two enlargement views shown for clarity;

FIG. 12A is a simplified exploded view illustration of a valve assembly of the multi-chamber syringe of FIGS. 1A-2B;

FIG. 12B is a simplified illustration of the valve assembly of FIG. 12A, shown in a first operative valve assembly orientation;

FIGS. 13B & 13C are simplified respective cut away and sectional views of the valve assembly of FIGS. 12A & 13A, shown in the second operative valve assembly orientation;

FIG. 14A is a simplified exploded-view illustration of the multi-chamber syringe of FIGS. 1A-2B;

FIG. 14B is a simplified illustration of the assembled multi-chamber syringe of FIGS. 1A-2B, shown in a first operative syringe orientation;

FIG. 15A is a simplified exploded-view illustration of the multi-chamber syringe of FIGS. 1A-2B;

FIG. 15B is a simplified illustration of the assembled multi-chamber syringe of FIGS. 1A-2B, shown in the second operative syringe orientation;

FIG. 17A is a simplified pictorial illustration of a multi-chamber syringe constructed and operative in accordance with another embodiment of the invention;

FIG. 17B is a simplified pictorial illustration of the multi-chamber syringe of FIG. 17A partially cut away to show the internal structure;

FIG. 19A is a simplified pictorial illustration of a barrel of the multi-chamber syringe of FIGS. 17A-18B, showing the barrel from the forward end;

FIG. 19B is a simplified pictorial illustration of the barrel of the multi-chamber syringe of FIGS. 17A-18B, showing the barrel from the rearward end;

FIG. 19C is a simplified view of the forward end of the barrel;

FIG. 19D is a sectional view of the barrel, this sectional view being taken along lines D-D of FIGS. 19A & 19B;

FIG. 19E is a simplified sectional view of the barrel, this sectional view being taken along lines E-E of FIGS. 19A & 19B, generally perpendicular to lines D-D;

FIG. 20A is a simplified pictorial illustration of an axially displaceable element of the multi-chamber syringe of FIGS. 17A-18B, showing the axially displaceable element from a forward end;

FIG. 20B is a simplified pictorial illustration of the axially displaceable element of the multi-chamber syringe of FIGS. 17A-18B, showing the axially displaceable element from a rearward end;

FIG. 20C is a simplified sectional view of the axially displaceable element, the sectional view being taken along lines C-C of FIGS. 20A & 20B;

FIG. 20D is a simplified sectional view of the axially displaceable element, the sectional view is taken along lines D-D of FIGS. 20A & 20B, generally perpendicular to lines C-C;

FIG. 21A is a simplified exploded view illustration of a valve assembly of the multi-chamber syringe of FIGS. 17A-18B;

FIG. 21B is a simplified illustration of the valve assembly of FIG. 21A, shown in a first operative valve assembly orientation;

FIG. 22A is a simplified illustration of the valve assembly of FIG. 21A, shown in an intermediate operative valve assembly orientation;

FIGS. 22B & 22C are simplified respective cut away and sectional views of the valve assembly of FIGS. 21A & 22B, shown in the intermediate operative valve assembly orientation;

FIG. 23A is a simplified illustration of the valve assembly of FIG. 21A, shown in a second operative valve assembly orientation;

FIGS. 23B & 23C are simplified respective cut away and sectional views of the valve assembly of FIGS. 21A & 23B, shown in the second operative valve assembly orientation;

FIG. 24A is a simplified exploded-view illustration of the assembled multi-chamber syringe of FIGS. 17A-18B;

FIG. 24B is a simplified illustration of the assembled multi-chamber syringe of FIGS. 17A-18B, shown in a first operative syringe orientation;

FIG. 25A is a simplified exploded-view illustration of the assembled multi-chamber syringe of FIGS. 17A-18B;

FIG. 25B is a simplified illustration of the assembled multi-chamber syringe of FIGS. 17A-18B, shown in an intermediate operative syringe orientation;

FIG. 26A is a simplified exploded view illustration of the assembled multi-chamber syringe of FIGS. 17A-18B;

FIG. 26B is a simplified illustration of the assembled multi-chamber syringe of FIGS. 17A-18B, shown in a second operative syringe orientation;

DETAILED DESCRIPTION OF PREFERRED EMBODIMENTS

Figure 1B:
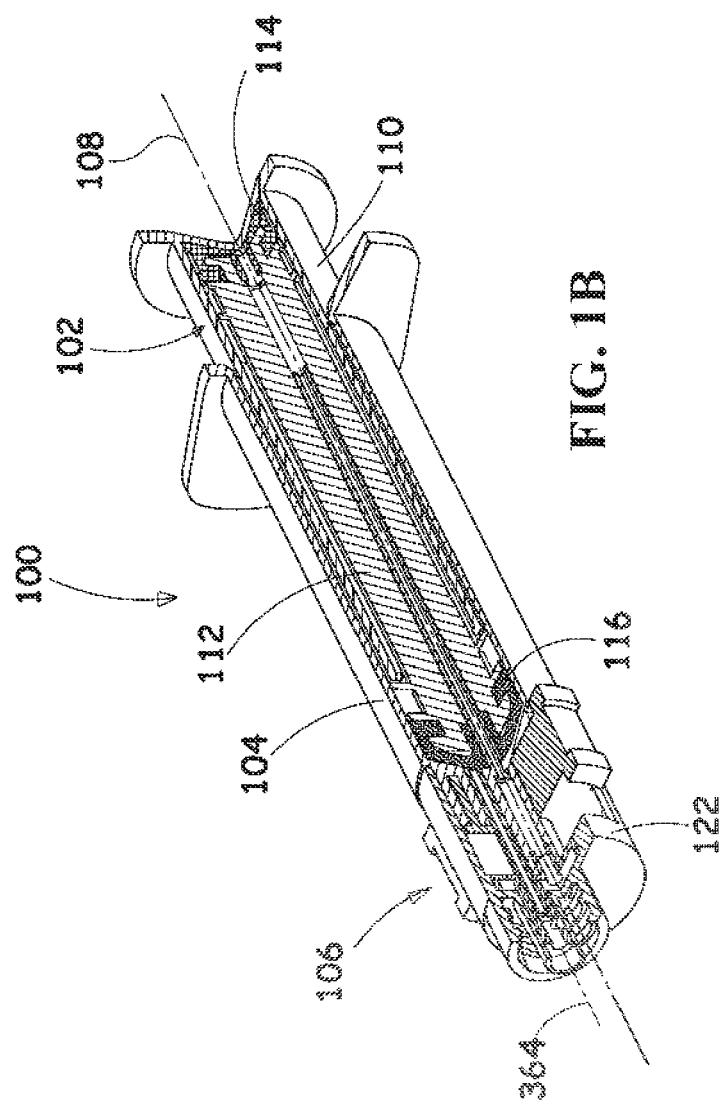
FIG. 1B is a simplified pictorial illustration of the multi-chamber syringe of FIG. 1A partially cut away to show the internal structure thereof.
Figure 2B:
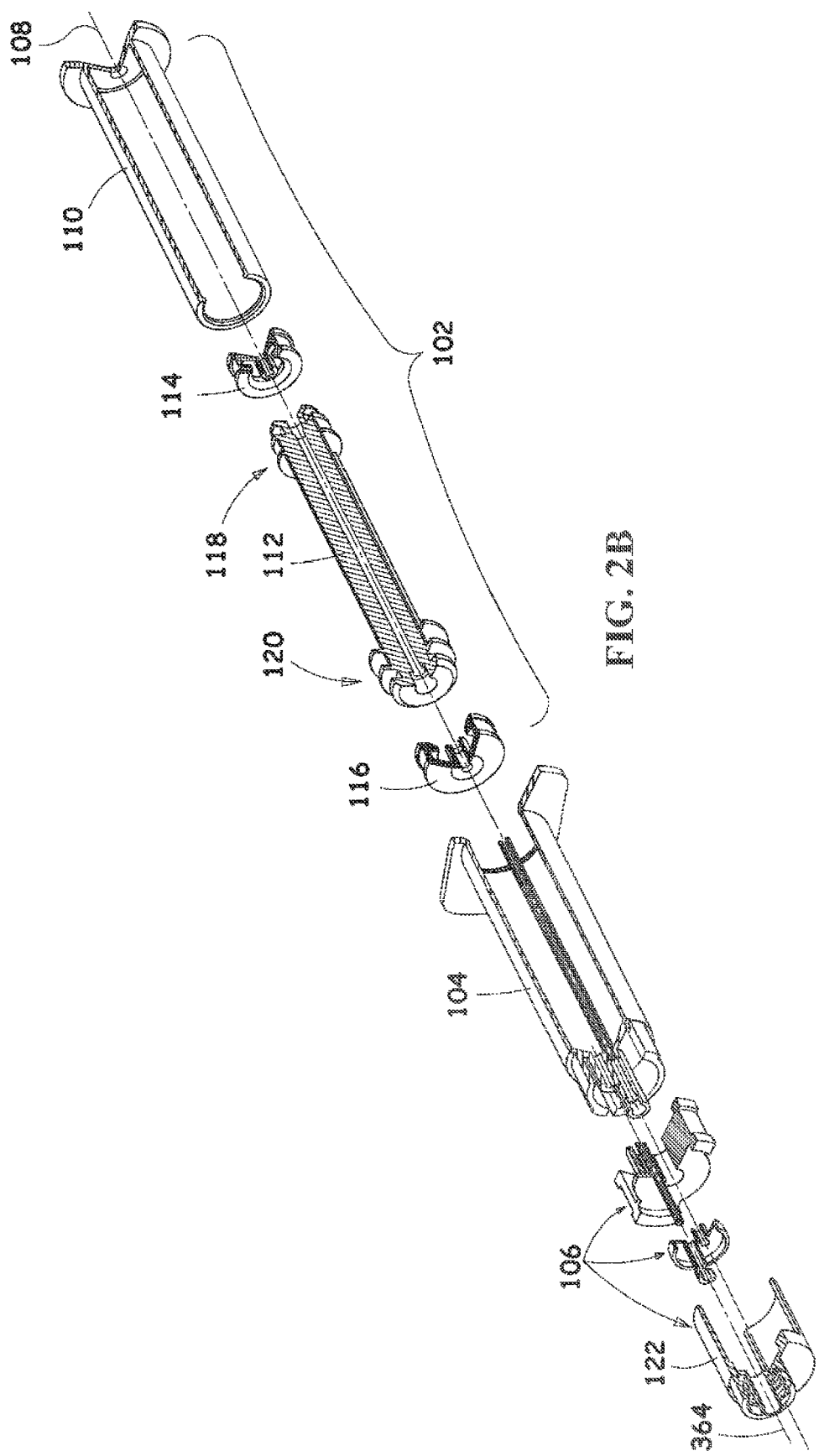
FIG. 2B is a simplified exploded illustration of the multi-chamber syringe of FIG. 2A partially cut away to show the internal structure.

Reference is now made to FIG. 1A, which is a simplified pictorial illustration of a multi-chamber syringe constructed and operative in accordance with an embodiment of the invention, and to FIG. 1B, which is a simplified pictorial illustration of the multi-chamber syringe of FIG. 1A, which is partially cut away to show the internal structure thereof. Reference is additionally made to FIG. 2A, which is a simplified exploded view illustration of the multi-chamber syringe of FIG. 1A and to FIG. 2B, which is a simplified exploded illustration of the multi-chamber syringe of FIG. 2A, which is partially cut away to show the internal structure thereof.

As will be described in greater detail hereinbelow, the multi-chamber syringe includes at least two separate fluid containers, at least two selectably openable fluid communication pathways associated with the fluid containers and a selector switch assembly that is operative to selectively fluidly interconnect either the first fluid container or the second fluid container with a syringe fluid flow passageway. Preferably, the selector switch assembly prevents simultaneous interconnection of both the first fluid container and the second fluid container with the syringe fluid flow passageway. Most preferably, at no point in time are both the first fluid container and the second fluid container interconnected with a syringe fluid flow passageway.

A multi-chamber syringe 100 preferably includes a piston assembly 102, which forms at least part of the second fluid container, a barrel 104, which forms at least part of the first fluid container and a valve assembly 106, which forms at least part of the selector switch assembly, which are preferably mutually aligned along a longitudinal axis 108. Piston assembly 102 and barrel 104 are arranged for mutual telescopic displacement along longitudinal axis 108.

The piston assembly 102 includes a piston assembly housing portion 110 and a plunger rod 112, which is partially disposed within piston assembly housing portion 110 and is slidable with respect thereto along longitudinal axis 108 within predetermined axial limits. Rearward and forward piston rings 114 and 116 are mounted on respective rearward and forward ends 118 and 120 of plunger rod 112 for axial displacement together with plunger rod 112 in fluid sealing engagement with an interior cylindrical surface of piston assembly housing portion 110.

Valve assembly 106 includes a luer connector portion 122 for operative engagement with any suitable medical device, such as a catheter, a vial adaptor or an IV set.

Reference is now made to FIGS. 3A & 3B, which illustrate the piston assembly housing portion 110, forming part of piston assembly 102.

The piston assembly housing portion 110 is preferably configured as a hollow cylinder integrally formed at a rearward end thereof with an end plate 123 and having an open forward end 124, preferably formed with an inwardly directed flange 125. Piston assembly housing portion 110 is formed with a generally circular cylindrical external surface 126 and a generally circular cylindrical internal surface 127, defining part of the first fluid chamber.

It is seen in FIG. 3B that the end plate 123 extends beyond external surface 126 and thus defines a flange 128 and is dimpled so as to define a concave rearward-facing surface 130 and a convex forward-facing surface 132.

Reference is now made to FIGS. 4A-4C which illustrate piston ring 114, forming part of piston assembly 112.

As seen in FIGS. 4A-4C, piston ring 114 is preferably integrally formed of a resilient material and is configured to be generally circularly symmetrical about axis 108. Piston ring 114 has a generally concave rearward facing surface 140, whose concavity preferably matches the convexity of forward-facing surface 132 of piston assembly housing portion 110 (FIGS. 3A & 3B). Surface 140 communicates with an axial bore 142, defined by an internal cylindrical portion 144, which extends to a forward end 145.

Surface 140 is surrounded by a rearward-facing flange 146, which is axially spaced from a forward-facing flange 148 by an external cylindrical surface 150.

Forward facing flange 148 has a generally flat forwardly-facing ring surface 152 interiorly of which is an inwardly tapered surface 154. Rearwardly of surface 154 is an inwardly facing cylindrical surface 156, which terminates in a rearwardly facing internal flat surface 158. Rearwardly of surface 158, there is provided an inwardly facing cylindrical surface 160 and rearwardly thereof there is provided an inwardly tapered surface 162 which terminates in a forwardly facing internal flat surface 164.

As shown in FIGS. 4A-4C, a circumferentially symmetric forward facing recess 166 is defined by surfaces 154, 156, 158, 160, 162 and 164 as clearly seen in FIG. 4C.

Figure 5A:
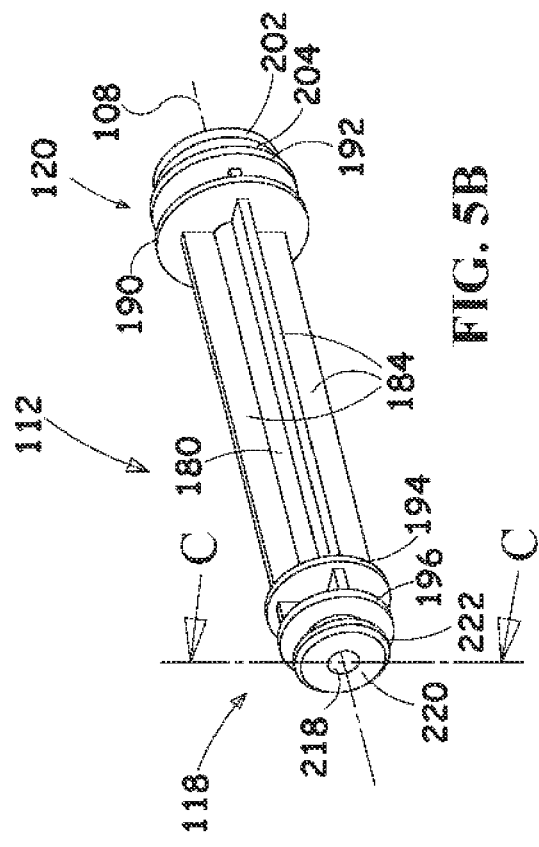
FIG. 5A is a simplified pictorial illustration of a plunger rod of the multi-chamber syringe of FIGS. 1A-2B, showing the plunger rod from the rearward end.
Figure 5B:
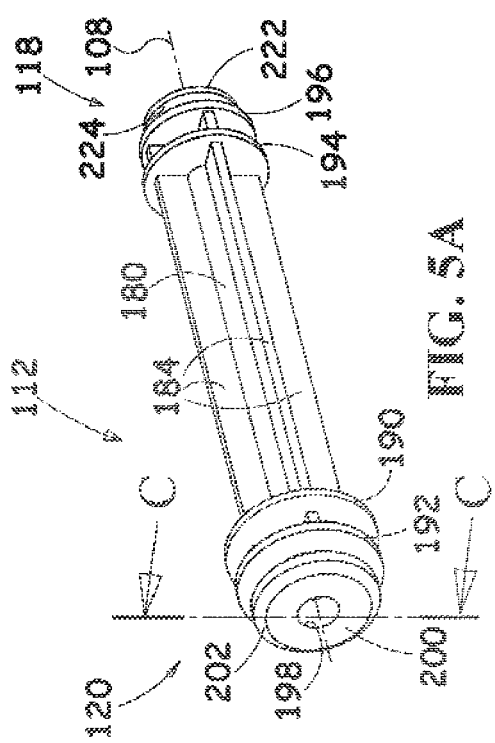
FIG. 5B is a simplified pictorial illustration of the plunger rod of the multi-chamber syringe of FIGS. 1A-2B, showing the plunger rod from the forward end.
Figure 5C:
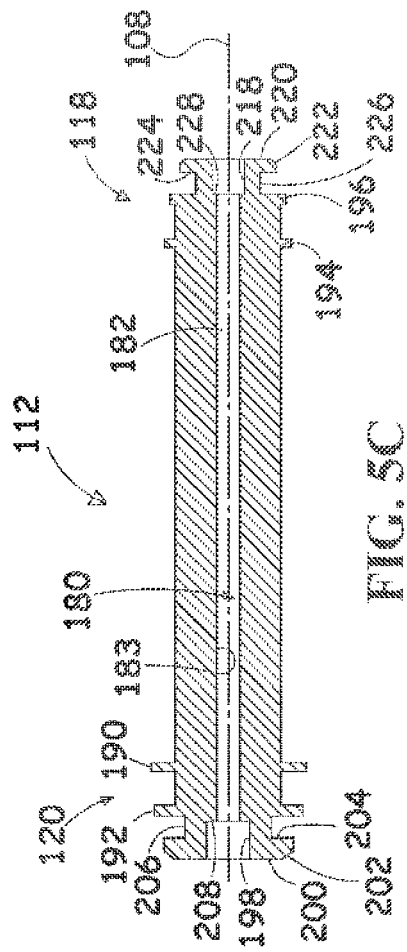
FIG. 5C is a simplified sectional view of the plunger rod, the sectional view being taken along lines C-C of FIGS. 5A & 5B.
Figure 12D:
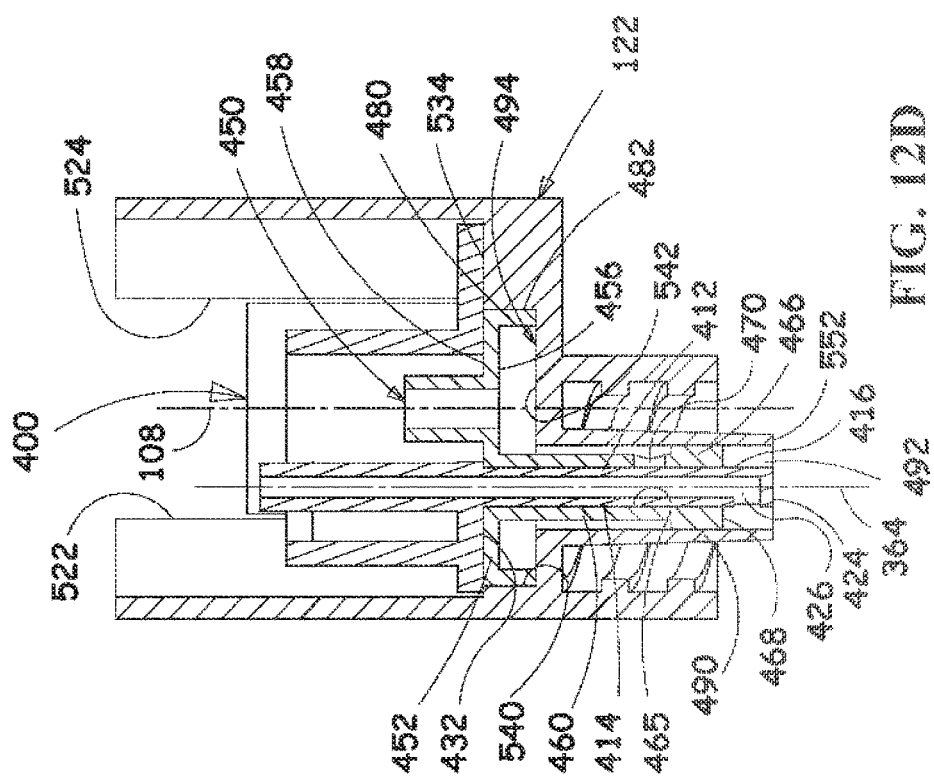
FIGS. 12C & 12D are simplified respective cut away and sectional views of the valve assembly of FIGS. 12A & 12B, shown in the first operative valve assembly orientation.
Figure 12C:
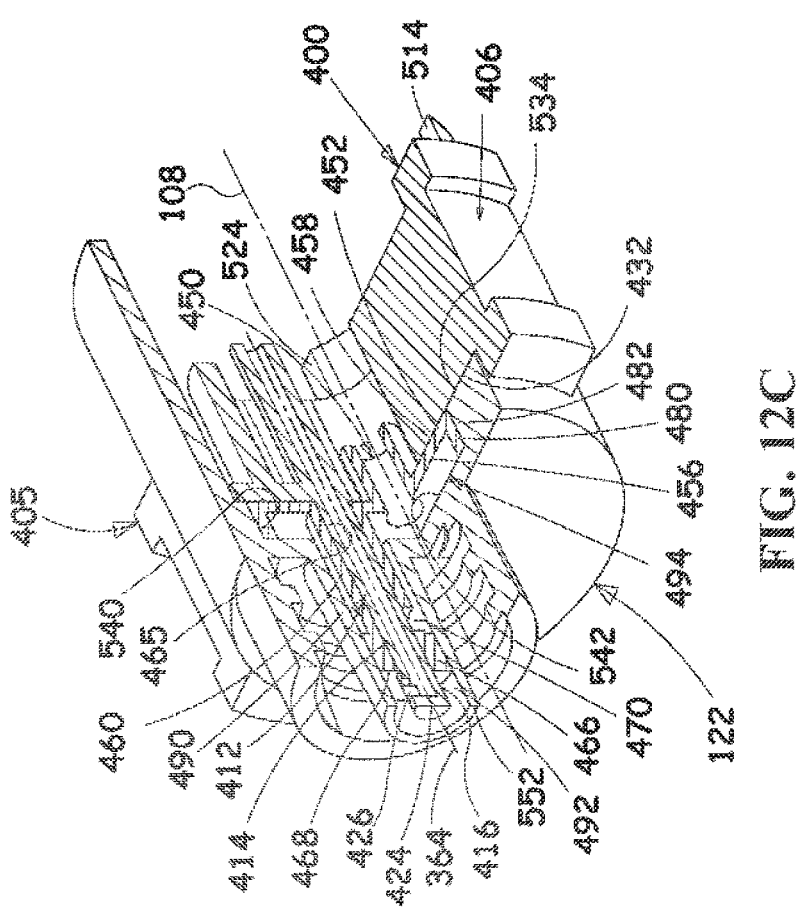
Figure 13A:
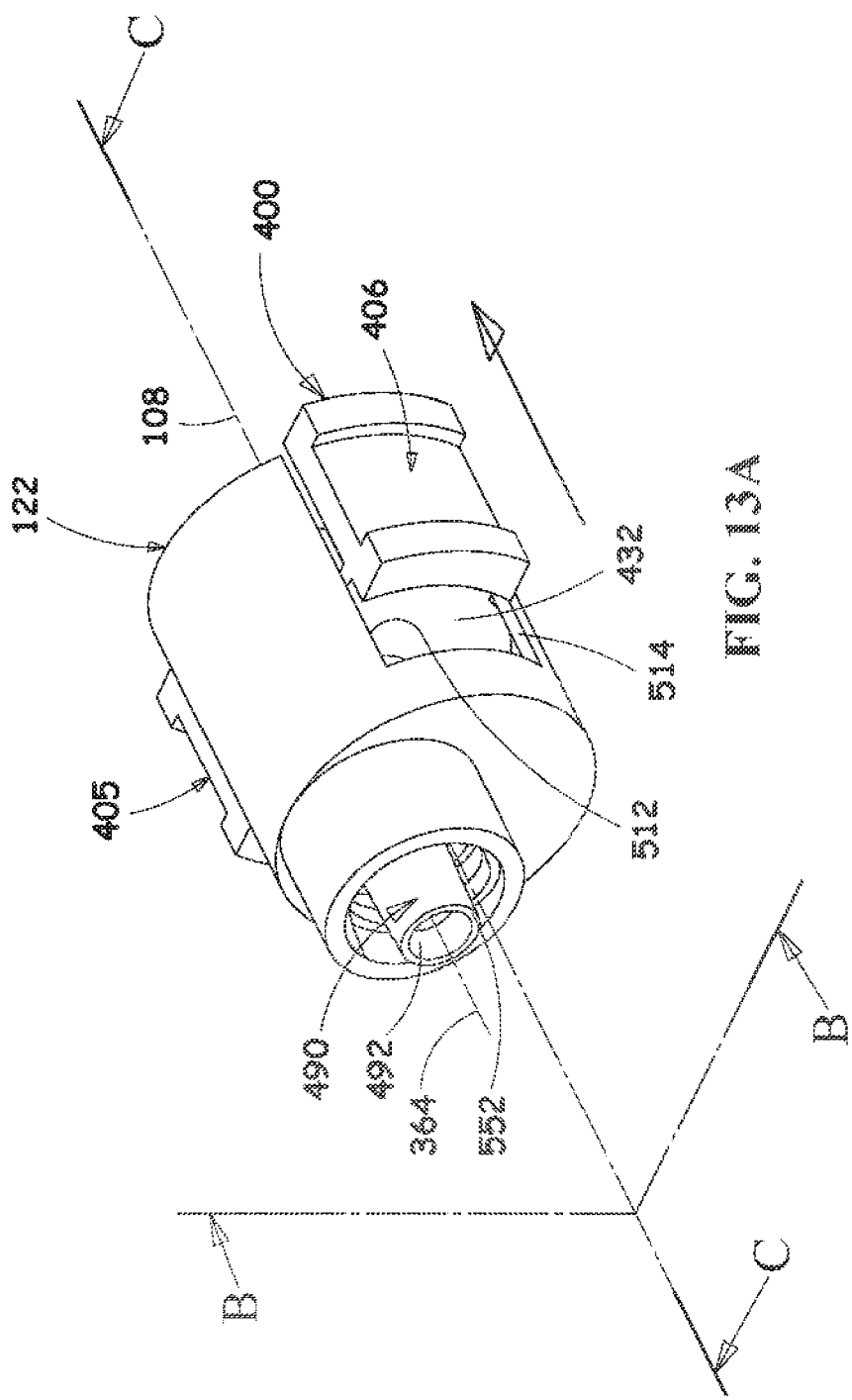
FIG. 13A is a simplified illustration of the valve assembly of FIG. 12A, shown in a second operative valve assembly orientation.
Figure 14C:
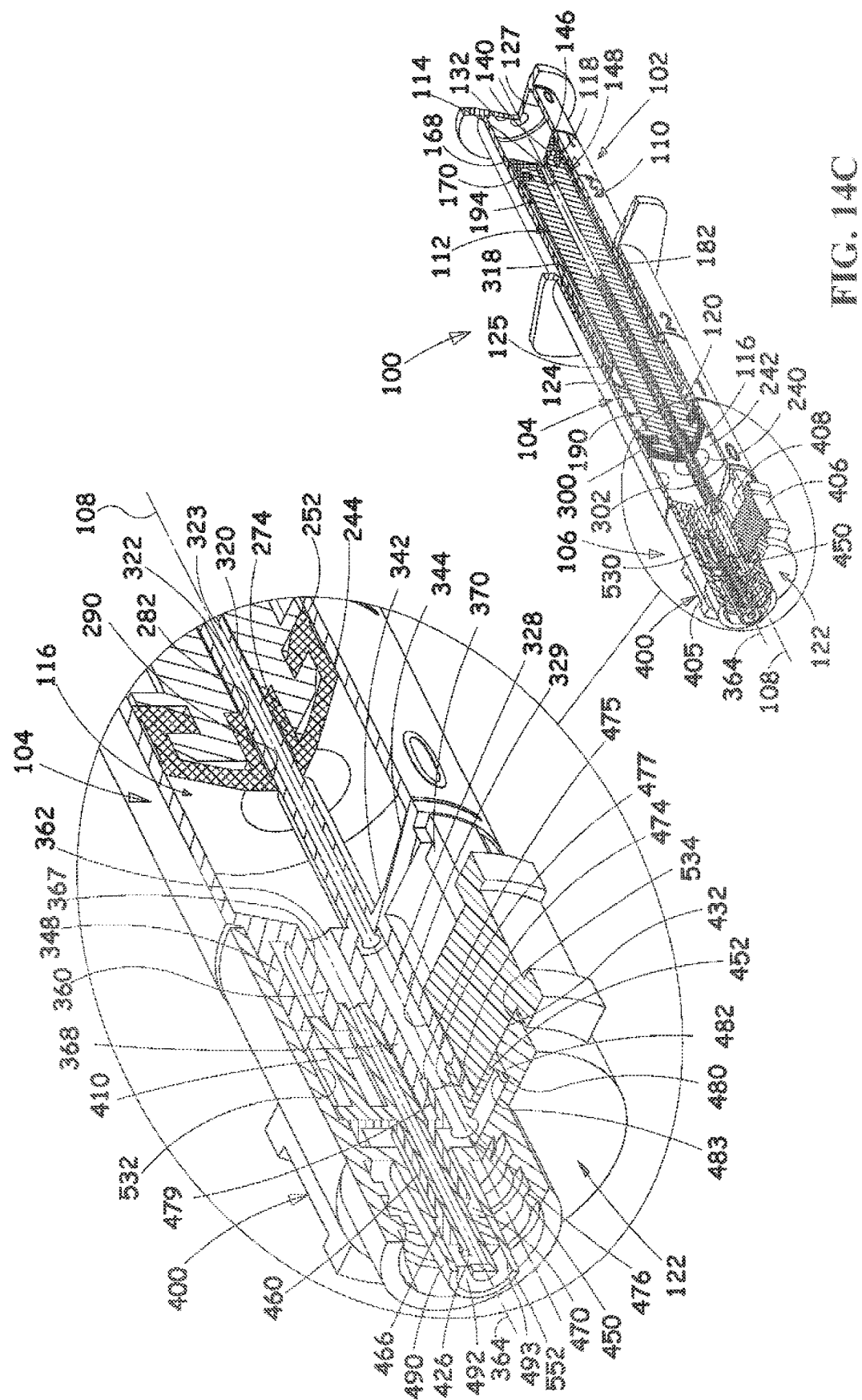
FIGS. 14C & 14D are simplified respective cut-away and sectional views of the assembled multi-chamber syringe of FIGS. 1A-2B, shown in the first operative syringe orientation.
Figure 14D:
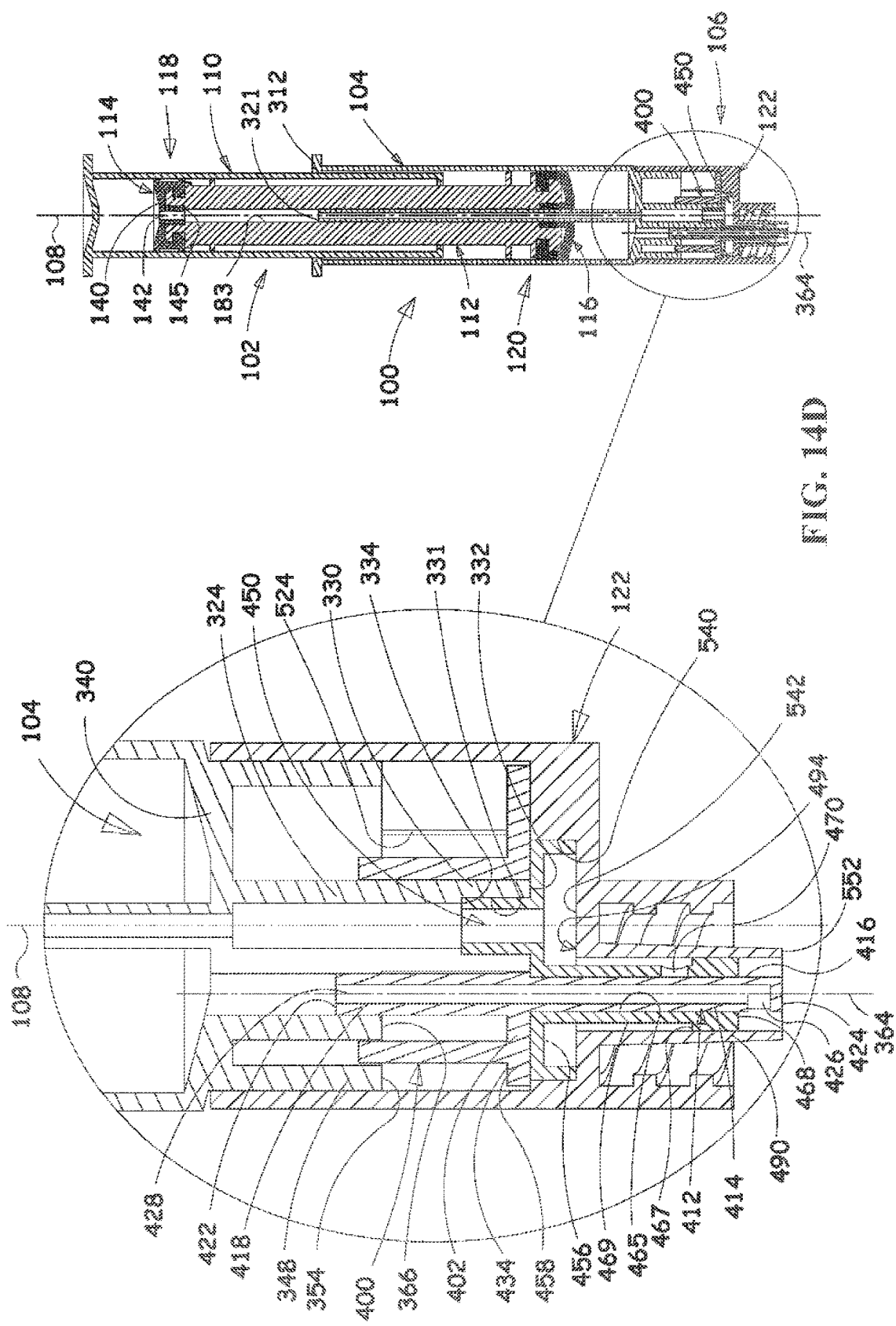

Outer cylindrical surfaces 168 and 170 of respective rearward-facing and forward-facing flanges 146 and 148 are preferably configured to provide axially displaceable sealing with interior surface 126 of piston assembly housing portion 110. Reference is now made to FIGS. 5A-5C, which illustrate plunger rod 112 of the multi-chamber syringe 100 of FIGS. 1A-2B.

Plunger rod 112 is preferably cylindrically symmetrical about longitudinal axis 108 and includes a generally cylindrical main portion 180, having an axial bore 182, defining an inner cylindrical surface 183, and typically four equally azimuthally mutually spaced radially outwardly facing fins 184, a rearward-facing end portion 118 and a forward-facing end portion 120.

Main portion 180 preferably includes, adjacent forward-facing end portion 120, a forward flange 190 which is axially spaced from an intermediate forward flange 192.

Main portion 180 also preferably includes adjacent rearward-facing end portion 118, a rearward flange 194 which is axially spaced from an intermediate rearward flange 196.

Forward-facing end portion 120 includes a central circular cylindrical bore 198, extending rearwardly from a forward flat surface 200 and communicating with axial bore 182. Extending radially outwardly and rearwardly from forward flat surface 200 is a tapered ring surface 202, which terminates in a rearwardly-facing ring surface 204. A circular cylindrical surface 206 extends rearwardly from surface 204 to intermediate forward flange 192. Bore 198 extends rearwardly to a forwardly facing ring surface 208, which is disposed radially inwardly of circular cylindrical surface 206.

Rearward-facing end portion 118 includes a central circular cylindrical bore 218, extending forwardly from a rearward flat surface 220 and communicating with axial bore 182. Extending radially outwardly and forwardly from rearward flat surface 220 is a tapered ring surface 222, which terminates in a forwardly-facing ring surface 224. A circular cylindrical surface 226 extends rearwardly from surface 224 to rearward intermediate flange 196. Bore 218 extends forwardly to a rearwardly facing ring surface 228, which is disposed radially inwardly of circular cylindrical surface 226.

Reference is now made to FIGS. 6A-6C, which illustrate piston ring 116 of the multi-chamber syringe 100 of FIGS. 1A-2B. The piston ring 116 is preferably integrally formed of a resilient material such as silicone or EPDM and is preferably circularly symmetric.

As seen in FIGS. 6A-6C, piston ring 116 is preferably formed with a generally flat forward surface 240. Extending radially outwardly and rearward from forward flat surface 240 is a tapered ring surface 242, which terminates in a generally circular cylindrical radially outward facing surface 244. Surface 244 extends rearwardly to a rearwardly facing ring surface 246.

Rearwardly of rearwardly facing ring surface 246 is a generally circular cylindrical radially outward facing surface 248, which is radially inwardly recessed with respect to surface 244. Surface 248 extends rearwardly to a forwardly facing ring surface 250. Rearwardly of forwardly facing ring surface 250 is a generally circular cylindrical radially outward facing surface 252, which is radially positioned similarly to surface 244 with respect to axis 108.

As also seen in FIGS. 6A-6C, the piston ring 116 is preferably formed with a generally flat rear surface 260 at the rearward end of surface 252. Extending radially inwardly and forward from rear flat surface 260 is a tapered ring surface 262, which terminates in a generally circular cylindrical radially inward facing surface 264. Surface 264 extends forwardly to a forwardly facing ring surface 266.

Forwardly of forwardly facing ring surface 266 is a generally circular cylindrical radially inward facing surface 268, which is radially outwardly recessed with respect to surface 264. Surface 268 extends forwardly to a rearwardly facing tapered ring surface 270, which terminates in a rearwardly facing ring surface 272. Extending rearwardly from surface 272 is a circular cylindrical portion 274 having an outer circular cylindrical surface 276 which terminates rearwardly in a rearward ring surface 278, which lies radially inwardly of tapered ring surface 262.

Extending forwardly of surface 278 is a central bore 280 having various internal cross-sectional dimensions. Adjacent surface 278 and forwardly thereof, bore 280 includes a radially inwardly-facing circular cylindrical surface 282, which terminates in a forwardly facing ring surface 284. Extending forwardly from surface 284 is a radially inwardly-facing circular cylindrical surface 286, which terminates in a rearward facing ring surface 288. Extending forwardly from surface 288 is a radially inwardly-facing circular cylindrical surface 290, which terminates at forward surface 240. Radially inwardly-facing circular cylindrical surface 290 is radially positioned similarly to surface 282 with respect to axis 108.

A circumferentially symmetric rearward facing recess 292 is defined by surfaces 262, 264, 266, 268, 270, 272 and 274 as clearly seen in FIG. 6C.

Reference is now made to FIGS. 7A-7E, which illustrate barrel 104 of the multi-chamber syringe 100 of FIGS. 1A-2B. Barrel 104 is preferably integrally formed of plastic, such as polyethylene or polypropylene and is 180 degree side-to-side symmetric about axis 108.

As seen in FIGS. 7A-7E, barrel 104 includes a circular cylindrical chamber 300 having a circular cylindrical inner surface 302 and a circular cylindrical outer surface 304. A pair of generally flat circular protrusions 306 extend radially outwardly from cylindrical outer surface 304 at a rearward end of chamber 300 and together define a circumferential edge surface 308, a forwardly facing surface 310, surrounding the rear end of chamber 300 and a corresponding rearwardly facing surface 312, surrounding an inwardly facing flange 314. Inwardly facing flange 314 includes a rearwardly-facing tapered ring surface 316 which terminates in a narrow cylindrical ring surface 318.

Arranged along the radial center of chamber 300 is an internal channel member 320 having an edge surface 321 defining an opening of a throughgoing internal bore 322 having an inner cylindrical surface 323. At a forward end thereof, internal bore 322 communicates with the interior of a generally cylindrical forward channel portion 324, which is coaxial therewith along axis 108. Forward channel portion 324 has an internal bore 326, which includes a rearward portion 328, having an inner cylindrical surface 329 and having an inner radius substantially greater than that of bore 322, and a forward portion 330, having an inner cylindrical surface 331 and having an inner radius somewhat greater than that of rearward portion 328. Forward channel portion 324 has a forward end surface 332 and an intermediate forward facing shoulder surface 334 between bore portions 328 and 330.

Circular cylindrical inner surface 302 terminates at a forward end of circular cylindrical chamber 300 in a rearward facing bulkhead 340 having a central flat rearward facing surface 342 surrounding a forward end of internal channel member 320. Extending rearwardly and radially outward from surface 342 is a tapered surface 344 which terminates at a forward end of circular cylindrical inner surface 302.

Bulkhead 340 defines a flat forward-facing surface 346 which terminates in an axially slotted generally cylindrical wall 348. Generally cylindrical wall 348 defines an outer cylindrical wall surface 350 and an inner cylindrical wall surface 352 which terminate forwardly at a forward edge surface 354. It is noted that forward channel portion 324 extends forwardly of forward edge surface 354.

An additional channel portion 360 extends forwardly from bulkhead 340 and includes a bore 362 which extends along an axis 364 through bulkhead 340 and communicates with the interior of chamber 300. Bore 362 terminates forwardly at a forward edge surface 366 thereof, which is preferably coplanar with edge surface 354. Bore 362 defines a cylindrical surface 367.

Channel portion 324 and additional channel portion 360 together define an obround cylindrical surface 368.

Generally cylindrical wall 348 is provided with a pair of axially extending slots 370, which are mutually separated by 180 degrees with respect to axis 108. Generally cylindrical wall is provided with a pair of enhanced thickness wall portions 372 which extends along both sides of each of slots 370.

Reference is now made to FIGS. 8A-8D, which illustrate an axially displaceable element 400, forming part of the valve assembly 106 of the multi-chamber syringe 100 of FIGS. 1A-2B. As seen in FIGS. 8A-8D, element 400 is preferably integrally formed of plastic, such as polyethylene or polypropylene and is 180 degree side-to-side symmetric about axis 108.

Element 400 preferably includes a flat apertured disc portion 402 arranged such that axis 108 extends though the center of an aperture 404 formed therein. Disposed axially outwardly of disc portion 402 are a pair of mutually 180 degree spaced finger grip portions designated by reference numerals 405 and 406, which are joined together to disc portion 402 by vanes 408. As seen with particularity in FIG. 8B, vanes 408 extend outwardly from a cylindrical portion 410, having an obround cross section, which portion 410 extends rearwardly from disc portion 402. Cylindrical portion 410 defines a bore 411, having an obround cross section.

A generally circular cylindrical cannula portion 412 extends forwardly and rearwardly of disc portion 402. A forward portion 414 of cannula portion 412 has an outer cylindrical surface 416 and has an outer diameter, which is slightly less than the outer diameter of a rearward portion 418, having an outer cylindrical surface 420. Cannula portion 412 is arranged to extend along axis 364 (FIGS. 7A-7E) and extends through and slight rearwardly of cylindrical portion 410, terminating in an open back end having an end surface 422.

Forward portion 414 is slightly longer than rearward portion 418 and has a closed forward end having an end surface 424 and a side aperture 426 just rearward of end surface 424, which is preferably directed in a direction opposite to that facing axis 106. Cannula portion 412 is formed with an axial bore 428 extending from end surface 422 along axis 364 to aperture 426. Cylindrical portion 410 and vanes 408 preferably have a mutually coplanar rearward facing edge 430. Flat apertured disc portion 402 has a forward facing surface 432 and a rearward facing surface 434.

Reference is now made to FIGS. 9A-9D, which illustrate a static element 450 forming part of valve assembly 106 of the multi-chamber syringe 100 of FIGS. 1A-2B. As seen in FIGS. 9A-9D, element 450 is preferably integrally formed of plastic, such as polyethylene or polypropylene and is 180 degree side-to-side symmetric about axis 108.

As seen in FIGS. 9A-9D, the static element 450 includes a generally circular shaped disc portion 452 centered on an axis 454, parallel to axes 108 and 364 and having a forward facing flat surface 456 and a rearward facing flat surface 458. A forward flow channel portion 460 extends forwardly of surface 456 and is formed with a circular cylindrical bore 462 that communicates with rearward facing flat surface 458 via an aperture 464 and has an inner cylindrical surface 465. Forward flow channel portion 460 has a thickened forward portion 466 which defines a rearwardly facing shoulder 467 and terminates in a forward edge 468. Forward flow channel 460 has an outer cylindrical surface 469. A side opening 470 facing in a direction towards axis 108, is formed in forward flow channel 460.

A rearward flow channel portion 474 extends rearwardly of surface 458, defines a rearward end surface 475 and is formed with a circular cylindrical bore 476, having an inner cylindrical surface 477. Bore 476 communicates with forward facing flat surface 456 via an aperture 478. Channel portion 474 has an outer cylindrical surface 479.

A circular cylindrical circumferential wall 480 extends forwardly from rearward facing flat surface 458 and has a radially outwardly facing surface 482, an inwardly facing surface 483 and a forward facing circumferential edge surface 484.

Reference is now made to FIGS. 10A-10D, which illustrate the luer connector 122 portion of valve assembly 106. As seen in FIGS. 10A-10D, luer connector portion 122 is preferably integrally formed of plastic, such as polyethylene or polypropylene and is 180 degree side-to-side symmetric about axis 108.

As seen in FIGS. 10A-10D, the luer connector portion 122 preferably includes a standard luer lock type connector portion 486 having internal threading 488 surrounding a flow channel 490 having a bore 492. Bore 492 communicates with a rearward-facing recess 494, which, in turn, communicates with the interior of a cylindrical housing portion 496. Cylindrical housing portion 496 is formed with a pair of side wall cut outs 498 and 500.

Cylindrical housing portion 496 is preferably formed with a rearward facing edge 510. Cut out 498 has side edges 512 and 514 and a rearward facing edge 516. Cut out 500 has side edges 522 and 524 and a rearward facing edge 526. Cylindrical housing portion 496 is preferably formed of an outer cylindrical wall surface 530 and an inner cylindrical wall surface 532. Inner cylindrical wall surface 532 terminates in a rearward facing flat wall surface 534 in which recess 494 is formed. Recess 494 has an inner facing cylindrical surface 540 and a rearward facing flat surface 542.

Standard luer lock type connector portion flow channel 490 has an outer tapered surface 550 which terminates in a forward facing edge 552.

Reference is now made to FIGS. 11A-11C, which illustrate a plunger sub-assembly 570 of the piston assembly 102, which subassembly includes plunger rod 112 (FIGS. 5A-5C), piston ring 114 (FIGS. 4A-4C) and piston ring 116 (FIGS. 6A-6C).

It is specifically seen that the piston ring 114 is mounted onto the plunger rod 112, such that the tapered ring surface 222 of the plunger rod 112 is retained within the forward facing recess 166 of the piston ring 114. Inwardly facing cylindrical surface 156 of the piston ring 114 abuts cylindrical surface 226 of the rearward facing end-portion 118 of the plunger rod 112. Forwardly-facing ring surface 152 of the piston ring 114 abuts intermediate rearward flange 196 of the plunger rod 112.

Pressure sealing engagement is provided between the internal cylindrical portion 144 of the piston ring 114 and cylindrical bore 218 of the plunger rod 112. A forward end of the internal cylindrical portion 144 lies against rearwardly facing ring surface 228 of the plunger rod 112. Axial bore 142 of the piston ring 114 communicates with axial bore 182 of the plunger rod 112.

It is further seen in FIGS. 11A-11C that the piston ring 116 is mounted onto the plunger rod 112 such that the tapered ring surface 202 of the plunger rod 112 is retained within rearward facing recess 292 of the piston ring 116. Surface 264 of the piston ring 116 abuts circular cylindrical surface 206 of the forward-facing end portion 120 of the plunger rod 112. Rear surface 260 of the piston ring 116 abuts a forward facing surface of intermediate forward flange 192 of the plunger rod 112.

Pressure sealing engagement is provided between the circular cylindrical portion 274 of the piston ring 116 and circular cylindrical bore 198 of the plunger rod 112. The rearward ring surface 278 of the circular cylindrical portion 274 lies against the forwardly facing ring surface 208 of the plunger rod 112. It is further seen that central bore 280 formed in cylindrical surface 286 fluidly communicates with axial bore 182 of the plunger rod 112.

Reference is now made to FIGS. 12A-12D, which illustrate valve assembly 106 of the multi-chamber syringe 100, which assembly includes axially displaceable element 400 (FIGS. 8A-8D), static element 450 (FIGS. 9A-9D) and luer connector portion 122 (FIGS. 10A-10D), in a first operative valve assembly orientation.

Thereafter, reference will be made to FIGS. 13A-13D, which illustrate the valve assembly 106 in a second operative valve assembly orientation.

It is appreciated that in both the first and second operative valve assembly orientations the following spatial relationships exist between the various elements:

Grip portion 405 of axially displaceable element 400 is positioned between side edges 522 and 524 of luer connector portion 122 and grip portion 406 is positioned between side edges 512 and 514 of luer connector portion 122;

The disc portion 452 of the static element 450 is positioned within the recess 494 of the luer connector portion 122, in a manner that the outwardly facing surface 482 of circumferential wall 480 of the static element 450 tightly and fluid sealingly fits cylindrical surface 540 of recess 494;

Forward facing flat surface 456 of the disc portion 452 of the static element 450 is spaced apart from the rearward facing flat surface 542 of recess 494 of luer connector portion 122;

Forward flow channel portion 460 of the static element 450 is partially inserted into flow channel 490 of the luer connector portion 122, such that thickened forward portion 466 of forward flow channel portion 460 of the static element 450 is fluid sealingly arranged within bore 492 of flow channel 490 of the luer connector portion 122 and the forward edge 468 of forward flow channel portion 460 is positioned rearwardly from forward facing edge 552 of flow channel 490 of the luer connector portion 122;

Cannula portion 412 of the axially displaceable element 400 is slidably fluid sealingly engaged with surface 465 of bore 462 of forward flow channel portion 460 of the static element 450; and The side opening 470 of forward flow channel portion 460 of the static element 450 and aperture 426 of cannula portion 412 of the axially displaceable element 400 face in opposite directions.

In the first operative valve assembly orientation, shown in FIGS. 12A-12D, the axially displaceable element 400 is positioned in a first orientation relative to the static element 450 and luer connector portion 122. Specifically forward facing surface 432 of the axially displaceable element 400 is positioned rearwardly of and abutting flat wall surface 534 of the luer connector portion 122.

The rearward facing flat surface 458 of disc portion 452 is located forwardly of and abutting forward facing surface 432 of the axially displaceable element 400.

End surface 424 of cannula portion 412 is positioned forwardly of forward edge 468 of forward flow channel portion 460 of the static element 450, at a location which does not block aperture 426 of the cannula 112. Accordingly, aperture 426 of cannula portion 412 of axially displaceable element 400 is open.

The side opening 470 of forward flow channel portion 460 of static element 450 is sealed closed by fluid sealing engagement of outer cylindrical surface 416 of forward portion 414 of axially displaceable element 400 with surface 465 of cylindrical bore 462 of forward flow channel portion 460 of the static element 450.

In the second operative valve assembly orientation, shown in FIGS. 13A-13D, the axially displaceable element 400 is positioned in a second orientation relative to the static element 450 and luer connector portion 122. Specifically, forward facing surface 432 of the axially displaceable element 400 is positioned rearwardly of and spaced from flat wall surface 534 of the luer connector portion 122.

The rearward facing flat surface 458 of disc portion 452 is spaced forwardly from forward facing surface 432 of the axially displaceable element 400.

End surface 424 of cannula portion 412 is positioned slightly rearwardly of side opening 470 of forward flow channel portion 460 of the static element 450. Accordingly, the side opening 470 of forward flow channel portion 460 of static element 450 is open.

Aperture 426 of cannula portion 412 of axially displaceable element 400 is closed by fluid sealing engagement of outer cylindrical surface 416 of forward portion 414 of axially displaceable element 400 with surface 465 of cylindrical bore 462 of forward flow channel portion 460 of the static element 450.

Reference is now made to FIGS. 14A-14D, which illustrate the multi-chamber syringe 100 in a first operative syringe orientation. Thereafter, reference will be made to FIGS. 15A-15D, which illustrate the multi-chamber syringe 100 in a second operative syringe orientation.

It is appreciated that in both the first and second operative syringe orientations the following spatial relationships exist between the various elements:

The rearward-facing end portion 118 of the plunger rod 112 is inserted into the piston assembly housing portion 110, in a manner that outer cylindrical surfaces 168 and 170 of rearward-facing and forward-facing flanges 146 and 148 of the piston ring 114 are sealingly slidably arranged within interior surface 127 of piston assembly housing portion 110;

The forward-facing end portion 120 of the plunger rod 112 is inserted into the barrel 104 in a manner that radially outward facing surfaces 244 and 252 of the piston ring 116 are sealingly slidably arranged within cylindrical inner surface 302 of circular cylindrical chamber 300 of barrel 104;

The rearward-facing end portion 118 of the plunger rod 112 with the piston ring 114 mounted thereon are slidably movable within piston assembly housing portion 110 from a first position to a second position. The first position is defined by engagement of forward-facing surface 132 of the piston assembly housing portion 110 with rearward facing recess 140 of the piston ring 114. The second position is defined by engagement of rearward flange 194 of the plunger rod 112 with inwardly directed flange 125 of the piston assembly housing portion 110;

The forward-facing end portion 120 of the plunger rod 112 and the piston ring 116 mounted thereon are slidably movable within barrel 104 from a first position to a second position. The first position is defined by engagement of forward flat surface 240 and tapered ring surface 242 of the piston ring 116 with the rearward facing surface 342 and tapered surface 344 of the barrel 104 respectively. The second position is defined by engagement of forward flange 190 of the plunger rod 112 with cylindrical ring surface 318 of barrel 104;

Internal channel member 320 of barrel 104 is inserted into axial bore 182 of the plunger rod 112 through circular cylindrical portion 274 of the piston ring 116. It is appreciated that internal channel member 320 of the barrel 104 is sealingly slidably arranged within the circular cylindrical portion 274 of the piston ring 116 due to engagement of the internal channel member 320 with inwardly-facing surfaces 282 and 290 of the circular cylindrical portion 274 of the piston ring 116;

The outer circumference of rearward flange 194 of plunger rod 112 substantially corresponds to internal surface 127 of the piston assembly housing portion 110. The outer circumference of the forward flange 190 of plunger rod 112 substantially corresponds to inner surface 302 of the barrel 104;

When the piston ring 114 and the piston ring 116 are both positioned in the first position, the piston assembly housing portion 110 is partially inserted into the barrel 104. When the piston rings 114 and 116 are both positioned in the second position, the forward end 124 of piston assembly housing portion 110 is rearwardly spaced apart from rearward end 312 of barrel 104;

The valve assembly 106 is attached to the barrel 104, preferably by heat welding and alternatively by use of an adhesive or via a snap-fit arrangement. Inner cylindrical wall surface 532 of outer cylindrical wall surface 530 of luer connector portion 122 is preferably attached to slotted cylindrical wall 348 of barrel 104;

The obround cylindrical surface 368 of barrel 104 is at least partially inserted into a corresponding obround cylindrical portion 410 of axially displaceable element 400. Flow channel portion 474 of static element 450 is inserted into forward portion 330 of the forward channel portion 324 of barrel 104 such that surface 479 of flow channel portion 474 fluid sealingly engages surface 330 of forward channel portion 324. A rearward end of flow channel portion 474 abuts forward facing ring portion 334 of forward flow channel portion 324. Rearward facing flat surface 458 of the static element 450 abuts forward end surface 332 of barrel 104;

Rearward portion 418 of cannula portion 412 of axially displaceable element 400 is at least partially inserted into bore 362 of channel portion 360 of barrel 104 in a slidably fluid sealing manner;

Vanes 408 of the axially displaceable element 400 are at least partially inserted into axially extending slots 370 of the barrel 104;

Grip portion 405 of axially displaceable element 400 is positioned between side edges 512 and 514 of luer connector portion 122 and grip portion 406 is positioned between side edges 522 and 524 of luer connector portion 122;

The disc portion 452 of the static element 450 is positioned within the recess 494 of the luer connector portion 122, in a manner that the outwardly facing surface 482 of circumferential wall 480 of the static element 450 tightly and fluid sealingly fits cylindrical surface 540 of recess 494;

Forward facing flat surface 456 of the disc portion 452 of the static element 450 is spaced apart from the rearward facing flat surface 542 of recess 494 of luer connector portion 122;

Forward flow channel portion 460 of the static element 450 is inserted into flow channel 490 of the luer connector portion 122, such that thickened forward portion 466 of forward flow channel portion 460 of the static element 450 is fluid sealingly arranged within bore 492 of flow channel 490 of the luer connector portion 122 and the forward edge 468 of forward flow channel portion 460 is positioned rearwardly from forward facing edge 552 of flow channel 490 of the luer connector portion 122;

Cannula portion 412 of the axially displaceable element 400 is fluid sealingly fitted within forward flow channel portion 460 of the static element 450; and The side opening 470 of forward flow channel portion 460 of the static element 450 and aperture 426 of cannula portion 412 of the axially displaceable element 400 face in mutually opposite directions.

It is a particular feature of an embodiment of the present invention that each of the barrel 104 and the piston assembly housing portion 110 are provided with a scale indication, as seen in FIGS. 14A-15C. The scale indication on the barrel 104 enables accurate determination of the amount of medicament remaining in the first fluid container at any given point in time and the scale indication of the piston assembly housing portion 110 enables accurate determination of the amount of flushing solution remaining in the second fluid container any given point in time.

In the first operative syringe orientation, the rearward portion 418 of cannula portion 412 of the axially displaceable element 400 is sealingly inserted through bore 362 of channel portion 360 of the barrel 104, in a manner that end surface 422 of cannula portion 412 is forwardly spaced apart from flat rearward facing surface 342 of bulkhead 340 of barrel 104.

Rearward facing surface 434 of disc portion 402 of the axially displaceable element 400 is forwardly spaced from forward edge surface 354 of cylindrical wall 348 and forward edge surface 366 of additional channel portion 360 of barrel 104.

The axially displaceable element 400 is selectively positioned in the first orientation relative to the static element 450 and luer connector portion 122. Specifically, forward facing surface 432 of the axially displaceable element 400 is positioned rearwardly of and abutting flat wall surface 534 of the luer connector portion 122.

The rearward facing flat surface 458 of disc portion 452 is located forwardly of and abutting forward facing surface 432 of the axially displaceable element 400.

End surface 424 of cannula portion 412 is positioned forwardly of side opening 470 of forward flow channel portion 460 of the static element 450.

The side opening 470 of forward flow channel portion 460 of static element 450 is closed by fluid sealing engagement of outer cylindrical surface 416 of forward portion 414 of axially displaceable element 400 with cylindrical bore 462 of forward flow channel portion 460 of the static element 450.

Aperture 426 of cannula portion 412 of axially displaceable element 400 is open.

Cylindrical portion 410 of the axially displaceable element 400 surrounds rearward flow channel portion 474 of the static element 450.

End surface 424 of cannula portion 412 of element 400 is coplanar with forward facing edge 552 of flow channel 490 of luer connector portion 122.

In this first operative syringe orientation the following relationships exist between fluid volumes:

A first fluid volume is defined by surfaces 302, 320, 342, 344 of chamber 300; surface 367 of bore 362 of barrel 104; surface 422, aperture 426 and bore 428 of cannula 412 of the axially displaceable element 400; and surfaces 240 and 242 of piston ring 116.

In the first operative syringe orientation, the first fluid volume defined hereinabove is in open communication with an outlet, which forms part of the syringe fluid flow passageway and is defined by surface 493 of bore 492 of flow channel 490 of the luer connector portion 122.

A second fluid volume is defined by surface 465, side opening 470, shoulder surface 467 and surface 469 of flow channel 460; surface 456 of disc portion 452; surface 483 of peripheral wall 480; surfaces 475 and 477 of bore 476 of rearward flow channel 474 of static element 450; surface 424 of axially displaceable element 400; and inner cylindrical surface 329 of portion 328 of channel portion 324; surfaces 321 and 323 associated with bore 322; surface 183 of bore 182 of the plunger rod 112; surface 145 associated with bore 142, surface 140 of flange 146 of rearward piston 114; and surfaces 127 and 132 of piston assembly housing portion 110.

In the first operative syringe orientation, the second fluid volume defined hereinabove is sealed by closing of aperture 470 produced by sealing engagement of outer surface 416 of cannula 412 with inner surface 465 of flow channel 460.

Reference is now made to FIGS. 15A and 15B which illustrate the multi-chamber syringe 100 in a second operative syringe orientation.

In the second operative syringe orientation, shown in FIGS. 15A-15D, the rearward portion 418 of cannula portion 412 of the axially displaceable element 400 is sealingly inserted through bore 362 of channel portion 360 of the forward housing portion 104, in a manner that end surface 422 of cannula portion 412 is generally coplanar with flat rearward facing surface 342 of bulkhead 340 of barrel 104.

Rearward facing surface 434 of disc portion 402 of the axially displaceable element 400 abuts forward edge surface 354 of cylindrical wall 348 and forward edge surface 366 of additional channel portion 360 of barrel 104.

The axially displaceable element 400 is selectively positioned in the second position relative to the static element 450 and luer connector 116. Specifically forward facing surface 432 of the axially displaceable element 400 is positioned rearwardly of and spaced from flat wall surface 534 of the luer connector portion 122.

The rearward facing flat surface 458 of disc portion 452 is spaced forwardly from forward facing surface 432 of the axially displaceable element 400.

End surface 424 of cannula portion 412 is positioned slightly rearwardly of side opening 470 of forward flow channel portion 460 of the static element 450. Accordingly, the side opening 470 of forward flow channel portion 460 of static element 450 is open.

Aperture 426 of cannula portion 412 of axially displaceable element 400 is closed by engagement of outer cylindrical surface 416 of forward portion 414 of axially displaceable element 400 with inner surface 465 of cylindrical bore 462 of forward flow channel portion 460 of the static element 450.

In this second operative syringe orientation the following relationships exist between the first and second fluid volumes:

The first fluid volume is sealed from the outlet, which forms part of the syringe fluid flow passageway and is defined by surface 493 of bore 492 of flow channel 490 of the luer connector portion 122 by virtue of the fact that aperture 426 of cannula portion 412 of axially displaceable element 400 is closed by engagement of outer cylindrical surface 416 of forward portion 414 of axially displaceable element 400 with inner surface 465 of cylindrical bore 462 of forward flow channel portion 460 of the static element 450.

The second fluid volume communicates with the outlet defined by surface 493 of bore 492 of flow channel 490 of the luer connector portion 122 via a forward portion of bore 462 by virtue of the fact that end surface 424 of cannula portion 412 is positioned slightly rearwardly of side opening 470 of forward flow channel portion 460 of the static element 450, thereby causing the side opening 470 of forward flow channel portion 460 of static element 450 to be open. It is appreciated that various clinical procedures require administration of several medical fluids, such as a medicament and a flushing solution, which, prior to the present invention, usually required a separate medicament syringe and a separate flushing solution syringe.

Typically for an intraveneous (IV) administration, a clinician used a first syringe containing flushing solution in order to draw a minimal amount of blood from a patient into the IV line thereby to check the patency of the patient's catheter. Thereafter, the clinician flushed the IV line and catheter with flushing solution from the first syringe. The first syringe was then discarded. Thereafter, the clinician used a second syringe with medicament in order to inject the medication into the patient's blood vessel. Following injection of the entire amount of medication is administered, the second syringe was discarded. A third syringe containing flushing solution was then used to flush the IV line to remove residual medication from the IV line. The aforementioned procedure required frequent connection and disconnection of syringes containing different substances in order to achieve an IV administration. This procedure increased the risk of introducing an infection into the patient and increased the risk of release of the medicament to the environment. Similar procedures were when delivering fluids through non-intravenous routes.

A clinical procedure employing an embodiment of the present invention and overcoming the aforementioned disadvantages is described in detail hereinbelow.

Figure 16A:
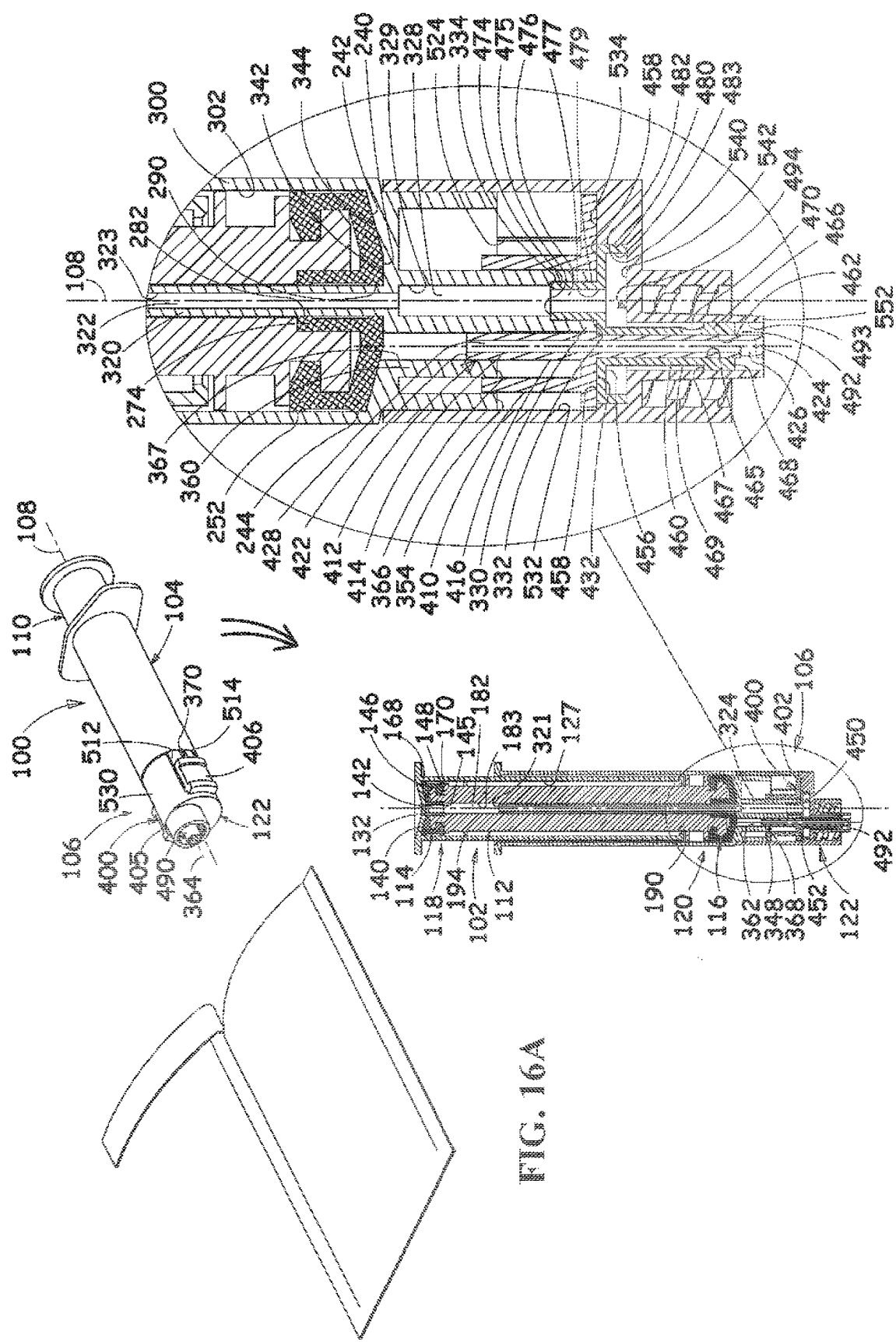
FIG. 16A is a simplified combined pictorial and sectional view illustration of the multi-chamber syringe in a first operative state, which is preferably the state in which the multi-chamber syringe is shipped and stored prior to use.

Reference is now made to FIG. 16A, which illustrates the multi-chamber syringe 100 in a first operative state, which is preferably the state in which the multi-chamber syringe 100 is shipped and stored prior to use.

As seen in FIG. 16A, in the first operative state, piston assembly 102 is fully inserted within barrel 104 along longitudinal axis 108.

It is appreciated that the following spatial relationships exist between the various elements:

The rearward-facing end portion 118 of the plunger rod 112 is inserted into the piston assembly housing portion 110, in a manner that outer cylindrical surfaces 168 and 170 of rearward-facing and forward-facing flanges 146 and 148 of the piston ring 114 are sealingly slidably arranged within interior surface 127 of piston assembly housing portion 110;

The forward-facing end portion 120 of the plunger rod 112 is inserted into the barrel 104 in a manner that radially outward facing surfaces 244 and 252 of the piston ring 116 are sealingly slidably arranged within cylindrical inner surface 302 of circular cylindrical chamber 300 of barrel 104;

The rearward-facing end portion 118 of the plunger rod 112 with the piston ring 114 mounted thereon are in the first position, defined by engagement of forward-facing surface 132 of the piston assembly housing portion 110 with rearward facing recess 140 of the piston ring 114;

The forward-facing end portion 120 of the plunger rod 112 with the piston ring 116 mounted thereon are in the first position defined by engagement of forward flat surface 240 and tapered ring surface 242 of the piston ring 116 with the rearward facing surface 342 and tapered surface 344 of the barrel 104 respectively;

Internal channel member 320 of barrel 104 is inserted into axial bore 182 of the plunger rod 112 through circular cylindrical portion 274 of the piston ring 116. It is appreciated that internal channel member 320 of the barrel 104 is sealingly slidably arranged within the circular cylindrical portion 274 of the piston ring 116 due to engagement of the internal channel member 320 with inwardly-facing surfaces 282 and 290 of the circular cylindrical portion 274 of the piston ring 116;

The outer circumference of rearward flange 194 of plunger rod 112 substantially corresponds to internal surface 127 of the piston assembly housing portion 110. The outer circumference of the forward flange 190 of plunger rod 112 substantially corresponds to inner surface 302 of the barrel 104;

In this first operative state, the piston ring 114 and the piston ring 116 are both positioned in the first position and the piston assembly housing portion 110 is partially inserted into the barrel 104;

The valve assembly 106 is attached to the barrel 104, preferably by heat welding and alternatively by use of an adhesive or via a snap-fit arrangement. Inner cylindrical wall surface 532 of outer cylindrical wall surface 530 of luer connector portion 122 is preferably attached to slotted cylindrical wall 348 of barrel 104;

The obround cylindrical surface 368 of barrel 104 is at least partially inserted into a corresponding obround cylindrical portion 410 of axially displaceable element 400. Flow channel portion 474 of static element 450 is inserted into forward portion 330 of the forward channel portion 324 of barrel 104 such that surface 479 of flow channel portion 474 fluid sealingly engages surface 330 of forward channel portion 324. A rearward end of flow channel portion 474 abuts forward facing ring portion 334 of forward flow channel portion 324. Rearward facing flat surface 458 of the static element 450 abuts forward end surface 332 of barrel 104;

Rearward portion 418 of cannula portion 412 of axially displaceable element 400 is at least partially inserted into bore 362 of channel portion 360 of barrel 104 in a slidably fluid sealing manner;

Vanes 408 of the axially displaceable element 400 are at least partially inserted into axially extending slots 370 of the barrel 104;

Grip portion 405 of axially displaceable element 400 is positioned between side edges 512 and 514 of luer connector portion 122 and grip portion 406 is positioned between side edges 522 and 524 of luer connector portion 122;

The disc portion 452 of the static element 450 is positioned within the recess 494 of the luer connector portion 122, in a manner that the outwardly facing surface 482 of circumferential wall 480 of the static element 450 tightly and fluid sealingly fits cylindrical surface 540 of recess 494;

Forward facing flat surface 456 of the disc portion 452 of the static element 450 is spaced apart from the rearward facing flat surface 542 of recess 494 of luer connector portion 122;

Forward flow channel portion 460 of the static element 450 is inserted into flow channel 490 of the luer connector portion 122, such that thickened forward portion 466 of forward flow channel portion 460 of the static element 450 is fluid sealingly arranged within bore 492 of flow channel 490 of the luer connector portion 122 and the forward edge 468 of forward flow channel portion 460 is positioned rearwardly from forward facing edge 552 of flow channel 490 of the luer connector portion 122;

Cannula portion 412 of the axially displaceable element 400 is fluid sealingly fitted within forward flow channel portion 460 of the static element 450; and The side opening 470 of forward flow channel portion 460 of the static element 450 and aperture 426 of cannula portion 412 of the axially displaceable element 400 face in mutually opposite directions.

In the first operative state, which corresponds to the first operative syringe orientation, the rearward portion 418 of cannula portion 412 of the axially displaceable element 400 is sealingly inserted through bore 362 of channel portion 360 of the barrel 104, in a manner that end surface 422 of cannula portion 412 is forwardly spaced apart from flat rearward facing surface 342 of bulkhead 340 of barrel 104.

Rearward facing surface 434 of disc portion 402 of the axially displaceable element 400 forwardly spaced from forward edge surface 354 of cylindrical wall 348 and forward edge surface 366 of additional channel portion 360 of barrel 104.

The axially displaceable element 400 is selectively positioned in the first orientation relative to the static element 450 and luer connector portion 122 (FIGS. 12A-12D. Specifically forward facing surface 432 of the axially displaceable element 400 is positioned rearwardly of and abutting flat wall surface 534 of the luer connector portion 122.

The rearward facing flat surface 458 of disc portion 452 is located forwardly of and abutting forward facing surface 432 of the axially displaceable element 400.

End surface 424 of cannula portion 412 is positioned forwardly of side opening 470 of forward flow channel portion 460 of the static element 450.

The side opening 470 of forward flow channel portion 460 of static element 450 is closed by fluid sealing engagement of outer cylindrical surface 416 of forward portion 414 of axially displaceable element 400 with cylindrical bore 462 of forward flow channel portion 460 of the static element 450.

Aperture 426 of cannula portion 412 of axially displaceable element 400 is open.

Cylindrical portion 410 of the axially displaceable element 400 surrounds rearward flow channel portion 474 of the static element 450.

End surface 424 of cannula portion 412 of element 400 is coplanar with forward facing edge 552 of flow channel 490 of luer connector portion 122.

In this first operative state, the following relationships exist between fluid volumes:

The first fluid volume defined by surfaces 302, 320, 342, 344 of chamber 300; surface 367 of bore 362 of barrel 104; surface 422, aperture 426 and bore 428 of cannula 412 of the axially displaceable element 400; and surfaces 240 and 242 of piston ring 116 is in open communication with an outlet defined by surface 493 of bore 492 of flow channel 490 of the luer connector portion 122.

The second fluid volume defined by surface 465, side opening 470, shoulder surface 467 and surface 469 of flow channel 460; surface 456 of disc portion 452; surface 483 of peripheral wall 480; surfaces 475 and 477 of bore 476 of rearward flow channel 474 of static element 450; surface 424 of axially displaceable element 400; and inner cylindrical surface 329 of portion 328 of channel portion 324; surfaces 321 and 323 associated with bore 322; surface 183 of bore 182 of the plunger rod 112; surface 145 associated with bore 142, surface 140 of flange 146 of rearward piston 114; and surfaces 127 and 132 of piston assembly housing portion 110 is sealed by closing of aperture 470, produced by sealing engagement of outer surface 416 of cannula 412 with inner surface 465 of flow channel 460.

In the first operative state, due to the full forward insertion of the piston assembly 102 in the barrel 104:

the first fluid volume is minimized, specifically the portion of the first fluid volume defined by surfaces 302, 320, 342, 344 of chamber 300 is effectively eliminated; and the second fluid volume is minimized, specifically the portion of the second fluid volume defined by surface 140 of flange 146 of rearward piston 114 and surfaces 127 and 132 of piston assembly housing portion 110 is effectively eliminated.

It is appreciated that the visually sensible different orientations of the axially displaceable member 400 for different operations may provide a safety feature. In the illustrated embodiment, when the axially displaceable element 400 is positioned in its first orientation, FIGS. 14A-14C, the medicament is in open communication with the syringe opening and thus the syringe 100 may present a hazard. When the axially displaceable element 400 is positioned at its second orientation, FIGS. 15A-15C, the flushing solution is in open communication with the syringe opening and thus the syringe 100 does not present a hazard.

Figure 16B:
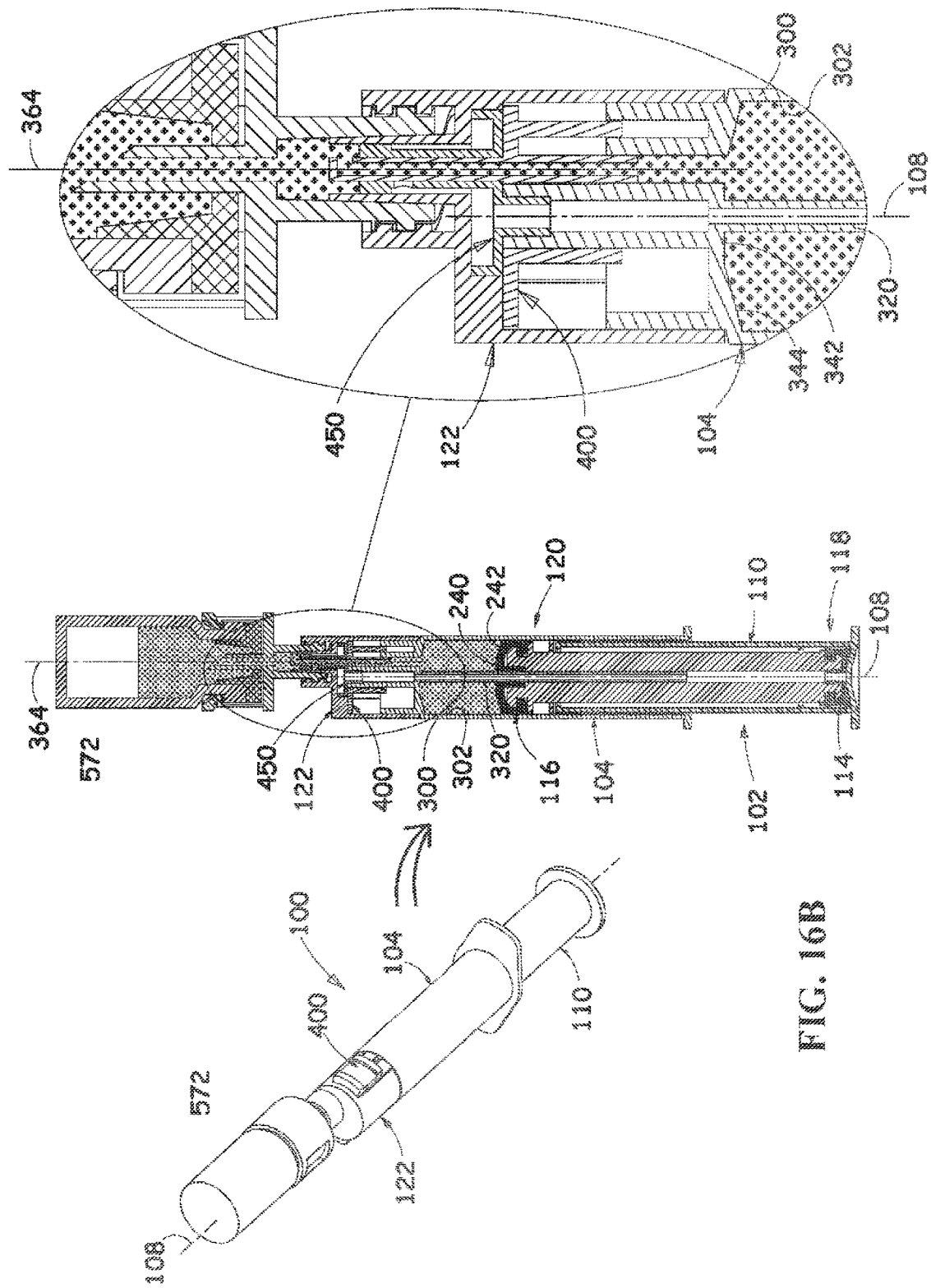
FIG. 16B is a simplified combined pictorial and sectional view illustration of the multi-chamber syringe in a second operative state, which is preferably the state in which the multi-chamber syringe is operative for aspiration of a medication from a medicament vial.

Reference is now made to FIG. 16B, which illustrates the multi-chamber syringe 100 in a second operative state, which is preferably the state in which the multi-chamber syringe 100 is operative for aspiration of a medication from a medicament vial 572.

As seen in FIG. 16B, in the second operative state, as compared with FIG. 16A, which illustrates the first operative state, piston assembly 102 is partially retracted from barrel 104 along longitudinal axis 108.

The mutual orientations of the various elements described in FIG. 16A remains essentially the same, other than as specifically set forth hereinbelow:

The piston assembly 102 is in a partially retracted orientation with respect to barrel 104. Accordingly, forward flat surface 240 and tapered ring surface 242 of the piston ring 116 are rearwardly spaced from rearward facing surface 342 and tapered surface 344 of the barrel 104 respectively.

The piston ring 116 is located between its first and second positions, piston ring 114 remains in the first position due to the negative pressure produced in the second volume by retraction of the piston assembly. This is a particular feature of this embodiment of the present invention.

In the second operative state, due to the partially retracted orientation of the piston assembly 102 in the barrel 104:

the first fluid volume is enlarged relative to its minimized state in the first operative state and at least a portion of the portion of the first fluid volume defined by surfaces 302, 320, 342, 344 of chamber 300 is filled with the medicament aspirated from the medicament vial 572 as may be additional portions of the first fluid volume.

Figure 15C:
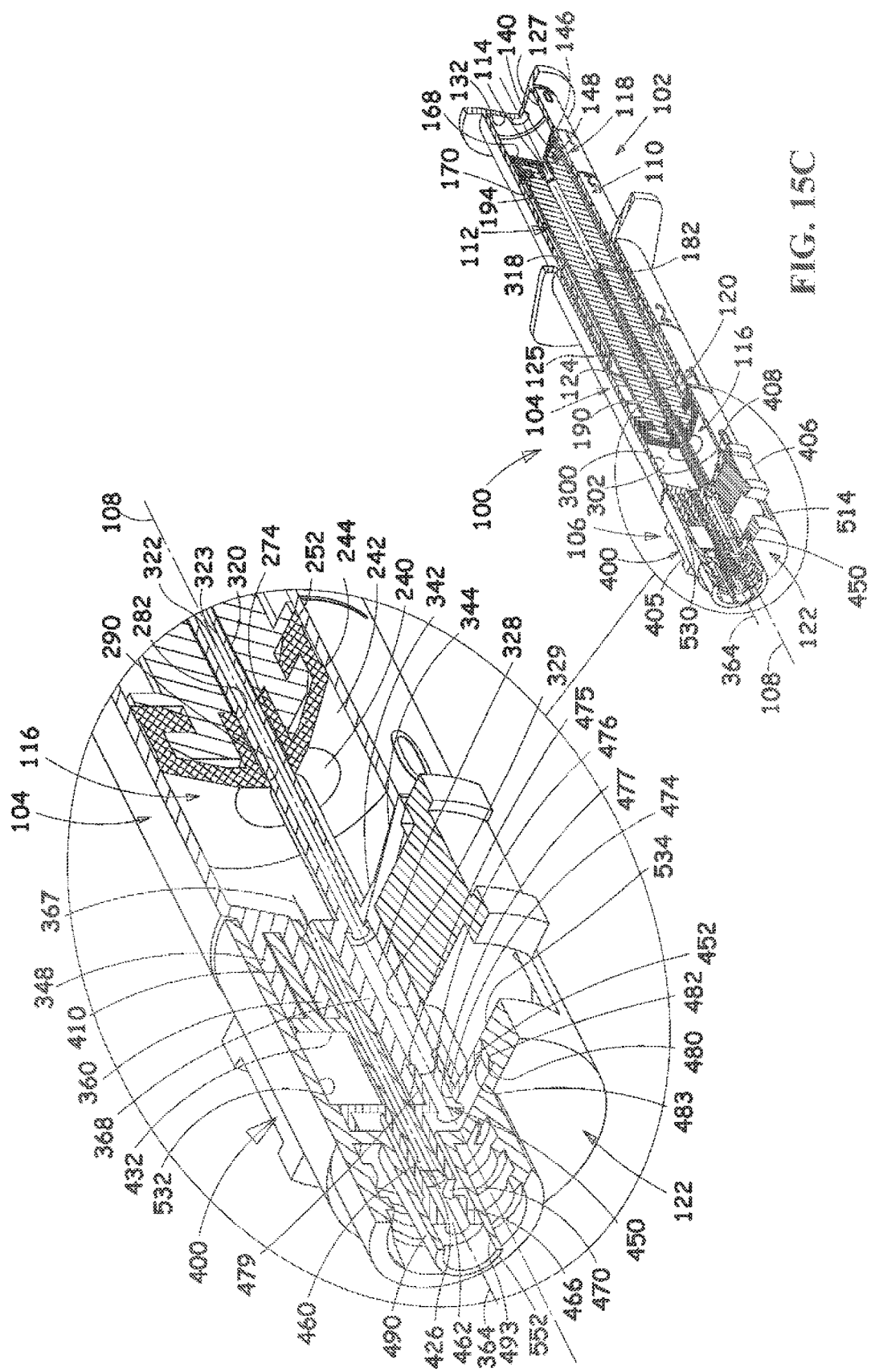
FIGS. 15C & 15D are simplified respective cut-away and sectional views of the assembled multi-chamber syringe of FIGS. 1A-2B, shown in the second operative syringe orientation.
Figure 15D:
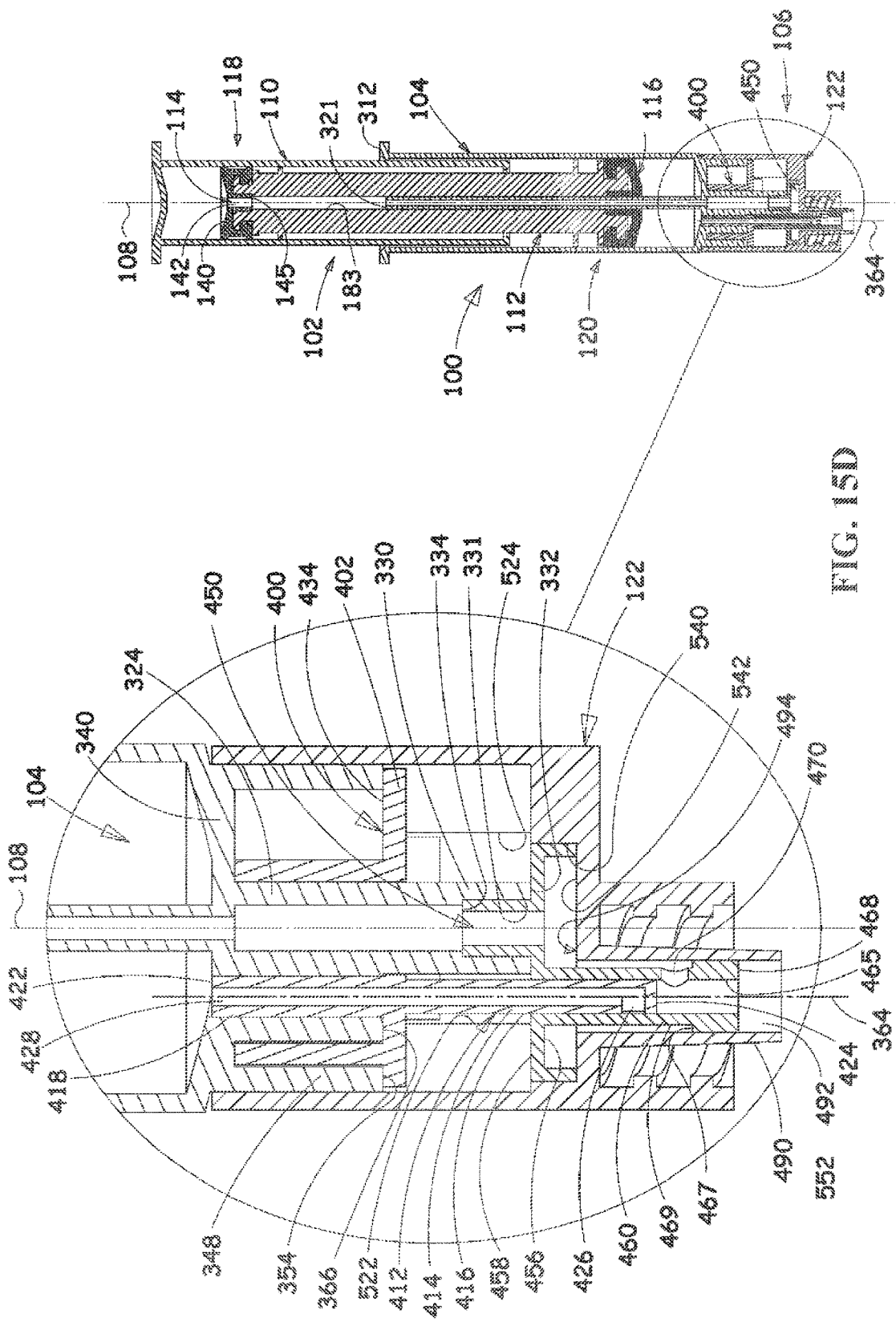

Once a desired amount of medication is aspirated, the axially displaceable element is rearwardly displaced to its second orientation, FIGS. 15A-15C.

It is a particular feature of an embodiment of the present invention that during this rearward displacement of the axially displaceable element 400 relative to the static element 450 and to the luer connector portion 122, the amount of residual medicament in the flow channel 490 of the luer connector portion 122 is substantially decreased. Preferably the amount of residual medicament is decreased by approximately 75% as compared with the amount of residual medicament in a standard luer connector, where neither axially displaceable element 400 nor static element 450 are present.

This reduction in the amount of residual medicament takes place due to the fact that the forward channel portion 460 of the static element and the cannula portion 412 of the axially displaceable element 400 occupy a substantial portion of the volume of the flow channel 490 of the luer connector portion 122.

Additionally, there is provided in accordance with a preferred embodiment of the present invention, fluid sealing engagement between the inner surface 465 of the forward flow channel 460 of the static element 450 and the outer surface 416 of the cannula portion 412. When the cannula portion 412 is displaced rearwardly to its second orientation, FIGS. 15A-15C, the closed end 424 of the cannula portion 412 is positioned rearwardly of the forward end 468 of the static element 450 and due to the sealing engagement of the cannula portion 412 and the forward flow channel portion 460 of the static element 450, the medicament remains sealed within the first fluid volume.

It is a further particular feature of the present invention that during rearward displacement of axial displacement element 400 relative to the static element 450, the outer surface 416 of cannula portion 412 wipes the residual medicament from inner surface 465 of the forward flow channel 460 of the static element 450 and provides for sealing of the medicament in the first fluid volume.

Figure 16C:
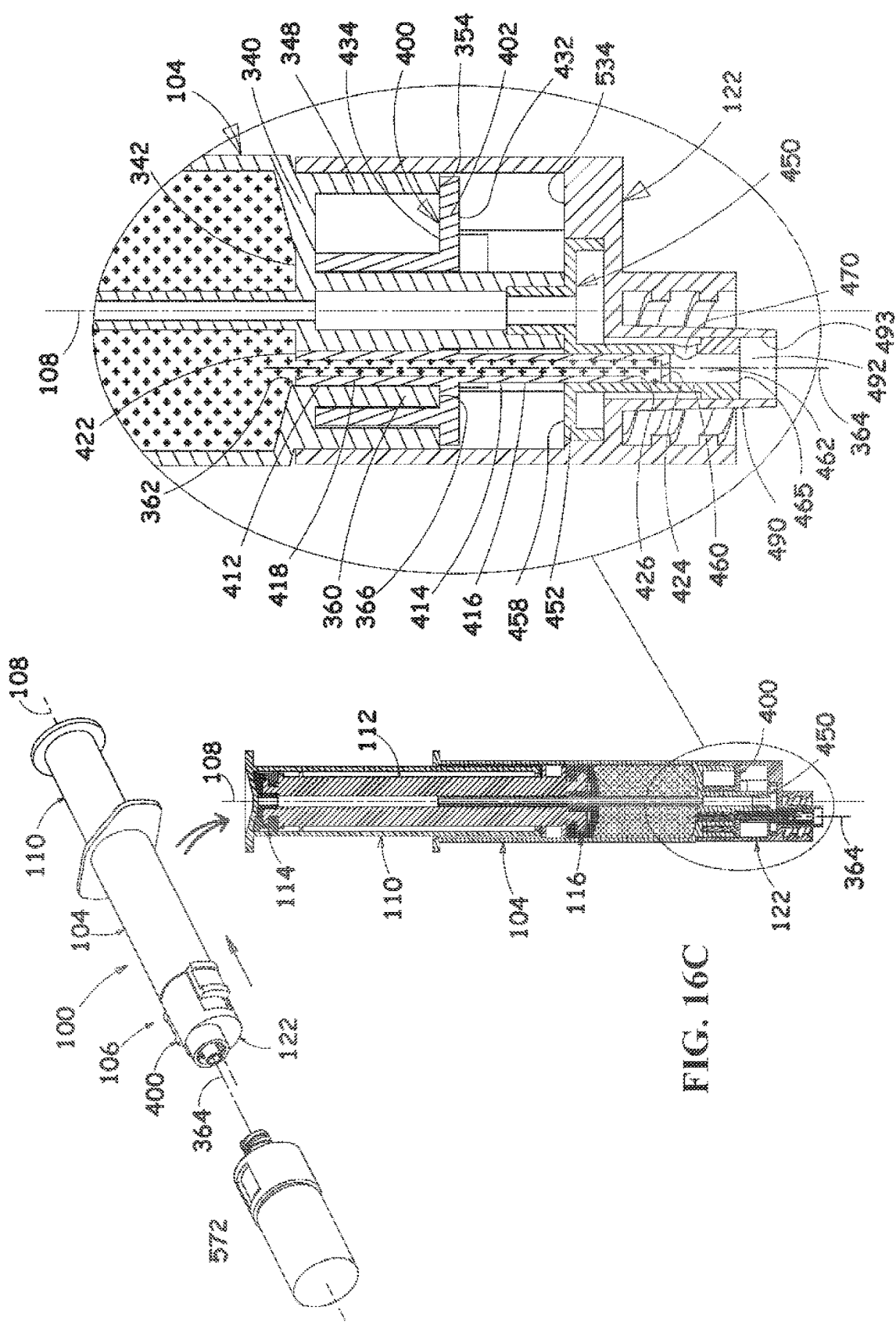
FIG. 16C is a simplified combined pictorial and sectional view illustration of the multi-chamber syringe in a third operative state, which is preferably the state in which the multi-chamber syringe is decoupled from the medicament vial following aspiration.

Reference is now made to FIG. 16C, which illustrates the multi-chamber syringe 100 in a third operative state, which is preferably the state in which the multi-chamber syringe 100 is decoupled from the medicament vial 572 and the axially displaceable element 400 is in its second orientation.

As seen in FIG. 16C, in the third operative state, as compared with FIG. 16B, which illustrates the second operative state, the axially displaceable element 400 is in its second orientation and specifically:

The rearward portion 418 of cannula portion 412 of the axially displaceable element 400 is sealingly inserted through bore 362 of channel portion 360 of the forward housing portion 104, in a manner that end surface 422 of cannula portion 412 is generally coplanar with flat rearward facing surface 342 of bulkhead 340 of barrel 104.

Rearward facing surface 434 of disc portion 402 of the axially displaceable element 400 abuts forward edge surface 354 of cylindrical wall 348 and forward edge surface 366 of additional channel portion 360 of barrel 104.

The axially displaceable element 400 is selectively positioned in the second position relative to the static element 450 and luer connector portion 122. Specifically forward facing surface 432 of the axially displaceable element 400 is positioned rearwardly of and spaced from flat wall surface 534 of the luer connector 116.

The rearward facing flat surface 458 of disc portion 452 is spaced forwardly from forward facing surface 432 of the axially displaceable element 400.

End surface 424 of cannula portion 412 is positioned slightly rearwardly of side opening 470 of forward flow channel portion 460 of the static element 450. Accordingly, the side opening 470 of forward flow channel portion 460 of static element 450 is open.

Aperture 426 of cannula portion 412 of axially displaceable element 400 is closed by engagement of outer cylindrical surface 416 of forward portion 414 of axially displaceable element 400 with inner surface 465 of cylindrical bore 462 of forward flow channel portion 460 of the static element 450.

The following relationships exist between the first and second fluid volumes:

The first fluid volume is sealed from the outlet defined by surface 493 of bore 492 of flow channel 490 of the luer connector portion 122 by virtue of the fact that aperture 426 of cannula portion 412 of axially displaceable element 400 is closed by engagement of outer cylindrical surface 416 of forward portion 414 of axially displaceable element 400 with inner surface 465 of cylindrical bore 462 of forward flow channel portion 460 of the static element 450.

The second fluid volume communicates with the outlet defined by surface 493 of bore 492 of flow channel 490 of the luer connector portion 122 via a forward portion of bore 462 by virtue of the fact that end surface 424 of cannula portion 412 is positioned slightly rearwardly of side opening 470 of forward flow channel portion 460 of the static element 450, thereby causing the side opening 470 of forward flow channel portion 460 of static element 450 to be open.

It is a particular feature of this embodiment of the invention that the medicament is sealingly retained in the first fluid volume and does not remain in the outlet defined by surface 493 of bore 492 of flow channel 490 of the luer connector portion 122, as shown.

Figure 16D:
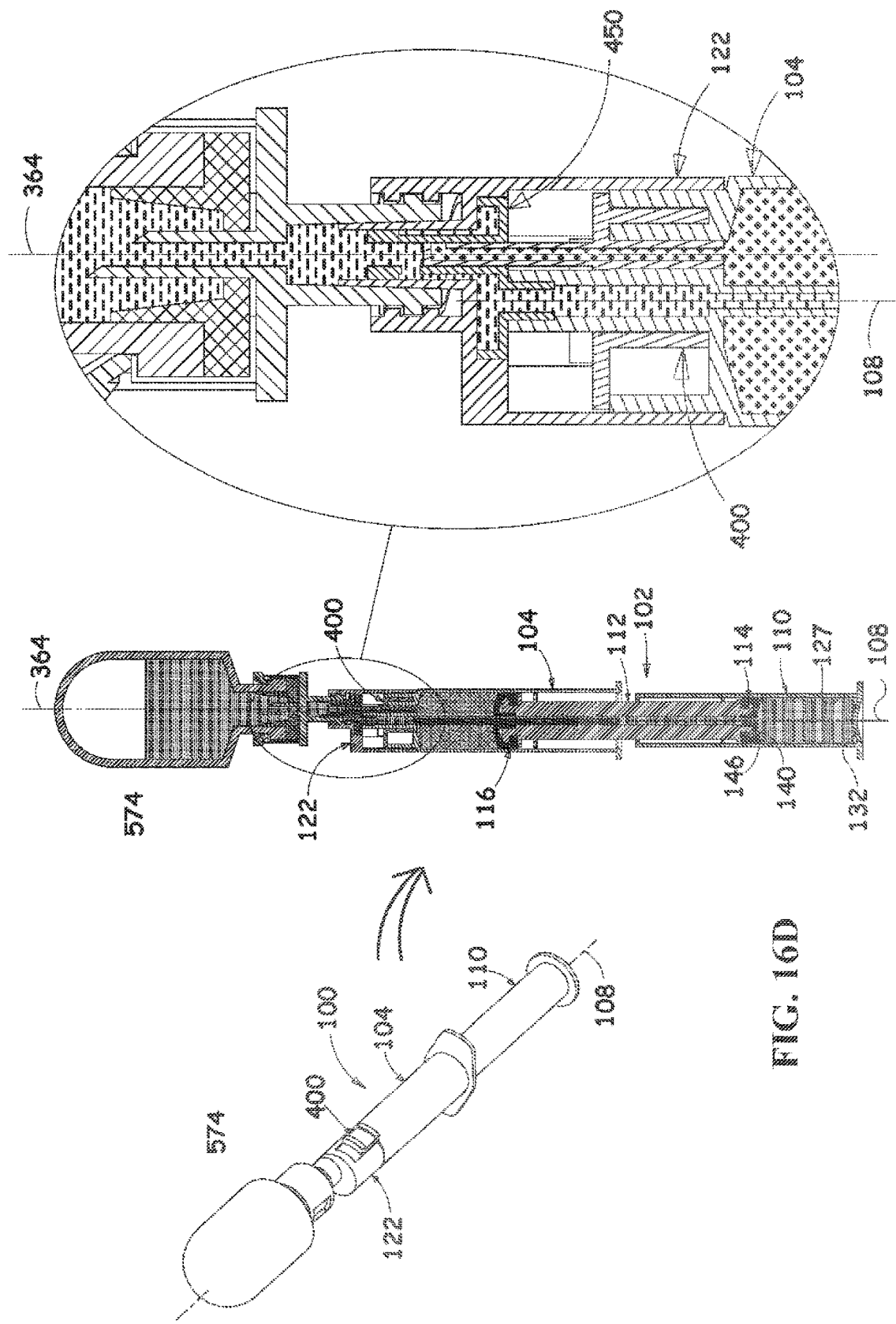
FIG. 16D is a simplified combined pictorial and sectional view illustration of the multi-chamber syringe in a fourth operative state, which is preferably the state in which the multi-chamber syringe is coupled to a vial of flushing solution.

Reference is now made to FIG. 16D, which illustrates the multi-chamber syringe 100 in a fourth operative state, which is preferably the state in which the multi-chamber syringe 100 is coupled to a vial 574 of flushing solution and the piston assembly housing portion 110 of the piston assembly 102 is retracted relative to the remainder of the piston assembly 102.

As seen in FIG. 16D, in the fourth operative state, as compared with FIG. 16C, which illustrates the third operative state, the mutual orientations of the various elements described in FIG. 16C remain essentially the same, other than as specifically set forth hereinbelow:

The piston assembly housing portion 110 of piston assembly 102 is in a partially retracted orientation with respect to the remainder of piston assembly 102.

Accordingly, rearward-facing surface 140 is forwardly spaced from forward-facing surface 132 of piston assembly housing portion 110.

The piston ring 114 is located between its first and second positions. Piston ring 116 remains in its intermediate position as shown in FIG. 16C due to the negative pressure produced in the first volume by retraction of the piston assembly housing portion 110 of piston assembly 102. This is a particular feature of this embodiment of the present invention.

In the fourth operative state, due to the partially retracted orientation of the piston assembly housing portion 110 of piston assembly 102 in the barrel 104:

the second fluid volume is enlarged relative to its minimized state in the previous operative states and at least a portion of the portion of the second fluid volume defined by surface 140 of flange 146 of rearward piston 114; and surfaces 127 and 132 of the piston assembly housing portion 110 is filled with the flushing solution aspirated from the flushing solution vial 574 as may be additional portions of the second fluid volume.

Figure 16E:
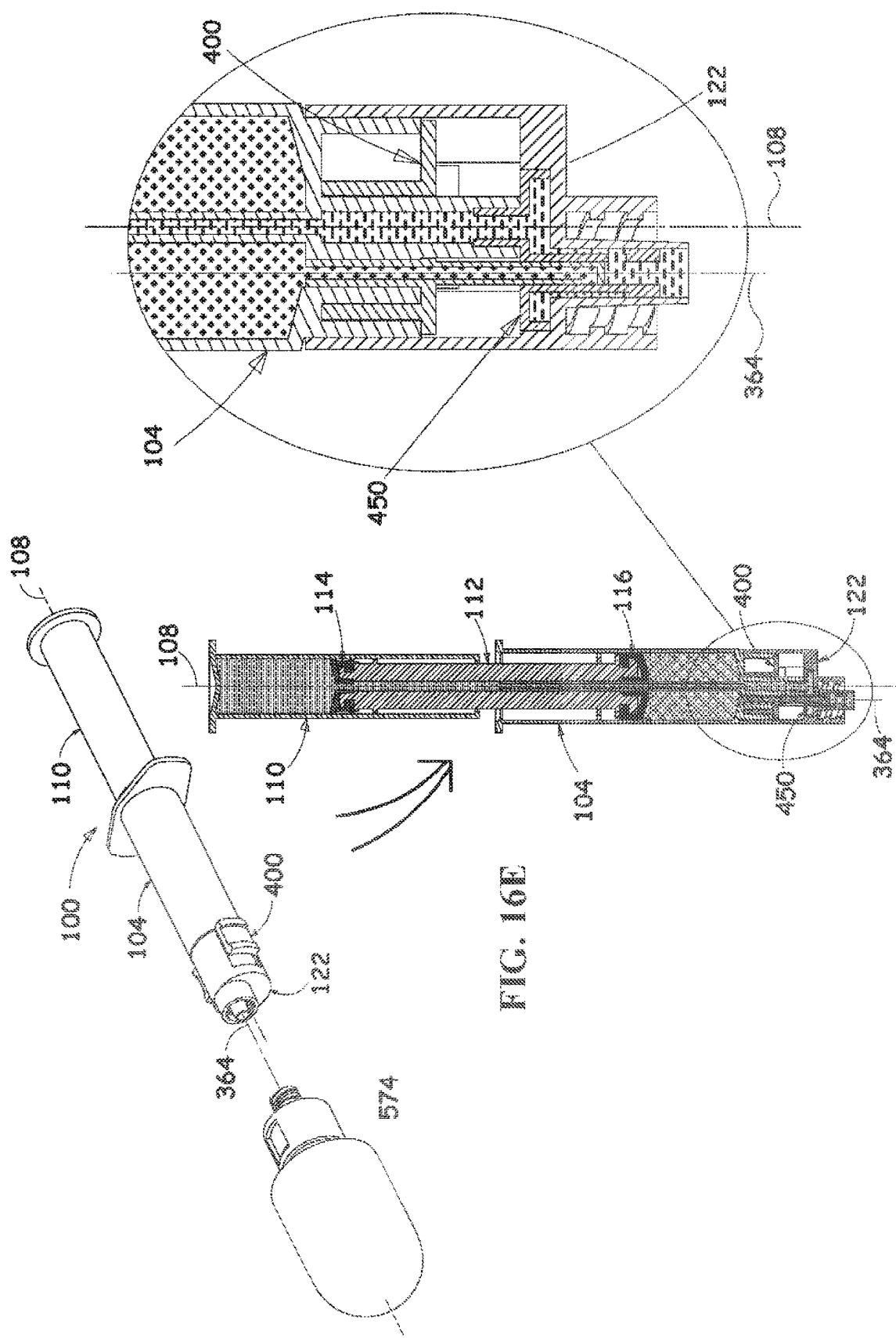
FIG. 16E is a simplified combined pictorial and sectional view illustration of the multi-chamber syringe in a fifth operative state, which is preferably the state in which the multi-chamber syringe is decoupled from the vial of flushing solution following aspiration of flushing solution therefrom.

Reference is now made to FIG. 16E, which illustrates the multi-chamber syringe 100 in a fifth operative state, which is preferably the state in which the multi-chamber syringe 100 is decoupled from the flushing solution vial 574. The relative orientations of the elements of the multi-chamber syringe 100 are essentially unchanged from those described hereinabove with reference to FIG. 16D. It is a particular feature of this embodiment of the present invention that at this final operative stage, the outlet defined by surface 493 of bore 492 of flow channel 490 of the luer connector portion 122 has been flushed with flushing solution.

Figure 16F:
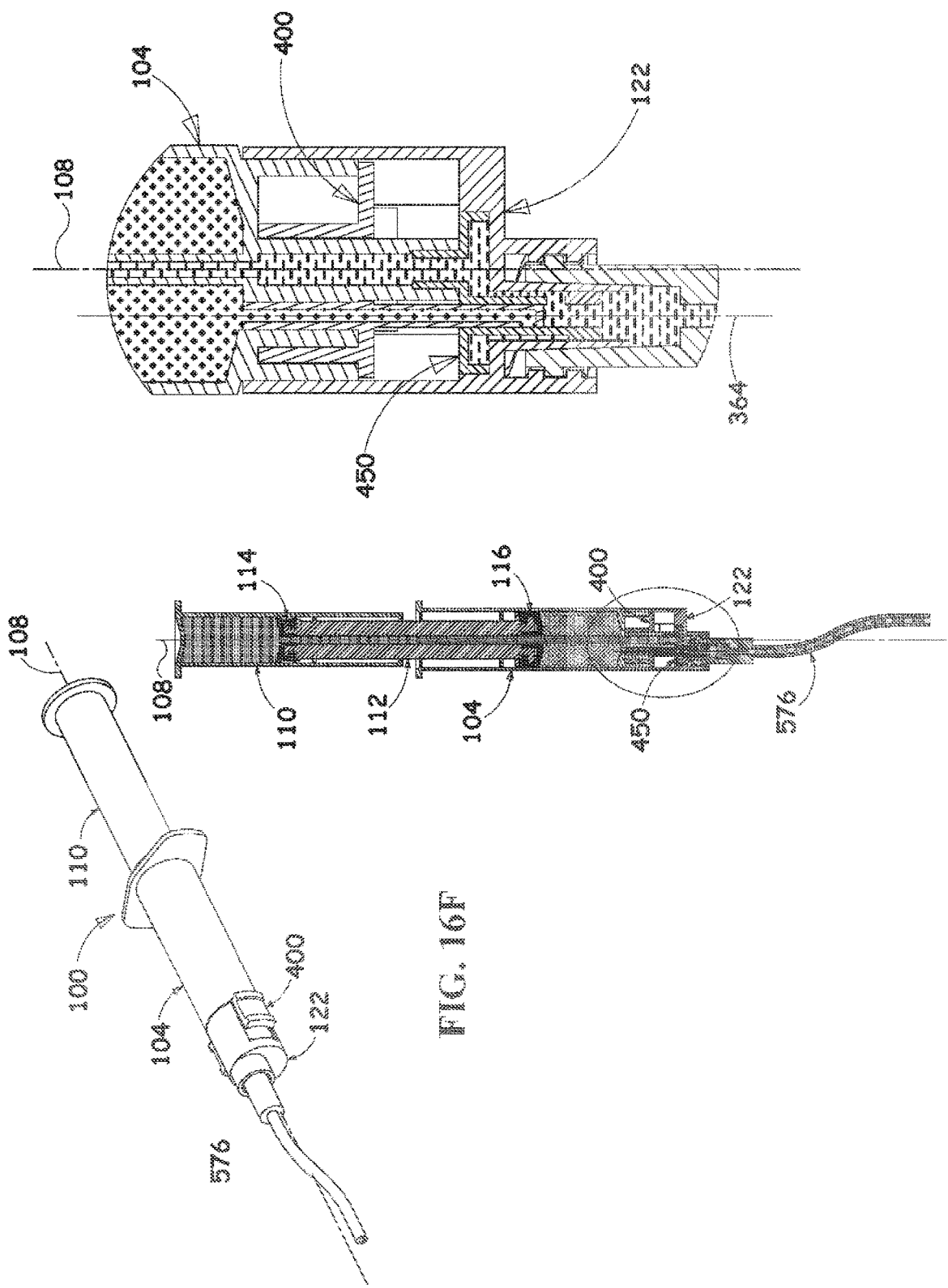
FIG. 16F is a simplified combined pictorial and sectional view illustration of the multi-chamber syringe in a sixth operative state, which is preferably the state in which the multi-chamber syringe injects flushing solution into a catheter.

Reference is now made to FIG. 16F, which illustrates the multi-chamber syringe 100 in a sixth operative state, which is preferably the state in which the multi-chamber syringe 100 is coupled at its outlet defined by surface 493 of bore 492 of flow channel 490 of the luer connector portion 122 to a catheter 576. The relative orientations of the elements of the multi-chamber syringe 100 are essentially unchanged from those described hereinabove with reference to FIG. 16E.

Figure 16G:
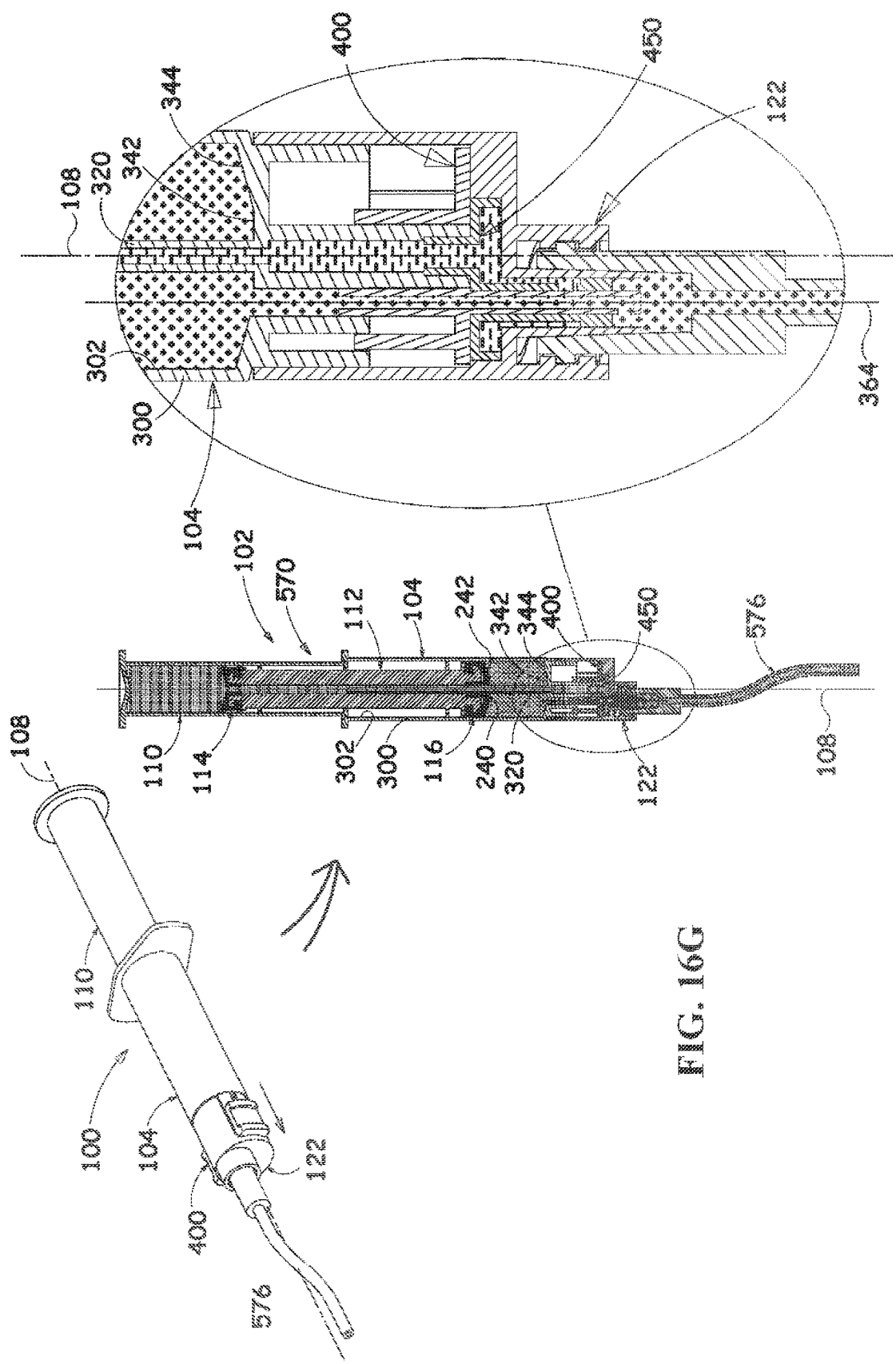
FIG. 16G is a simplified combined pictorial and sectional view illustration of the multi-chamber syringe in a seventh operative state, which is preferably the state in which the multi-chamber syringe injects medication into the catheter.

Reference is now made to FIG. 16G, which illustrates the multi-chamber syringe 100 in a seventh operative state, which is preferably the state in which the multi-chamber syringe 100 injects medication into the catheter 576, the axially displaceable element 400 is in its first orientation and the both piston assembly housing portion 110 and the plunger sub-assembly 570 of the piston assembly 102 are pushed forwardly relative to barrel 104.

As compared with the arrangement shown in FIG. 16F, here forward flat surface 240 and tapered ring surface 242 of the piston ring 116 are less rearwardly spaced from rearward facing surface 342 and tapered surface 344 of the barrel 104 respectively, thus decreasing the first volume and forcing the medication into the catheter 576 via the outlet defined by surface 493 of bore 492 of flow channel 490 of the luer connector portion 122.

The piston ring 116 is displaced more forwardly between its first and second positions, piston ring 114 remains in its position shown in FIG. 16F, due to the positive pressure produced in the second volume by forward directed pressure exerted on the piston assembly 102. This is a particular feature of this embodiment of the present invention.

In the seventh operative state, due to the forward displacement of the piston assembly 102 in the barrel 104:

the first fluid volume is decreased relative to its state in the sixth operative state and at least a portion of the portion of the first fluid volume defined by surfaces 302, 320, 342, 344 of chamber 300 is thereby eliminated, with the result that the medicament that had earlier been aspirated from the medicament vial 572 is injected into the catheter 576.

Figure 16H:
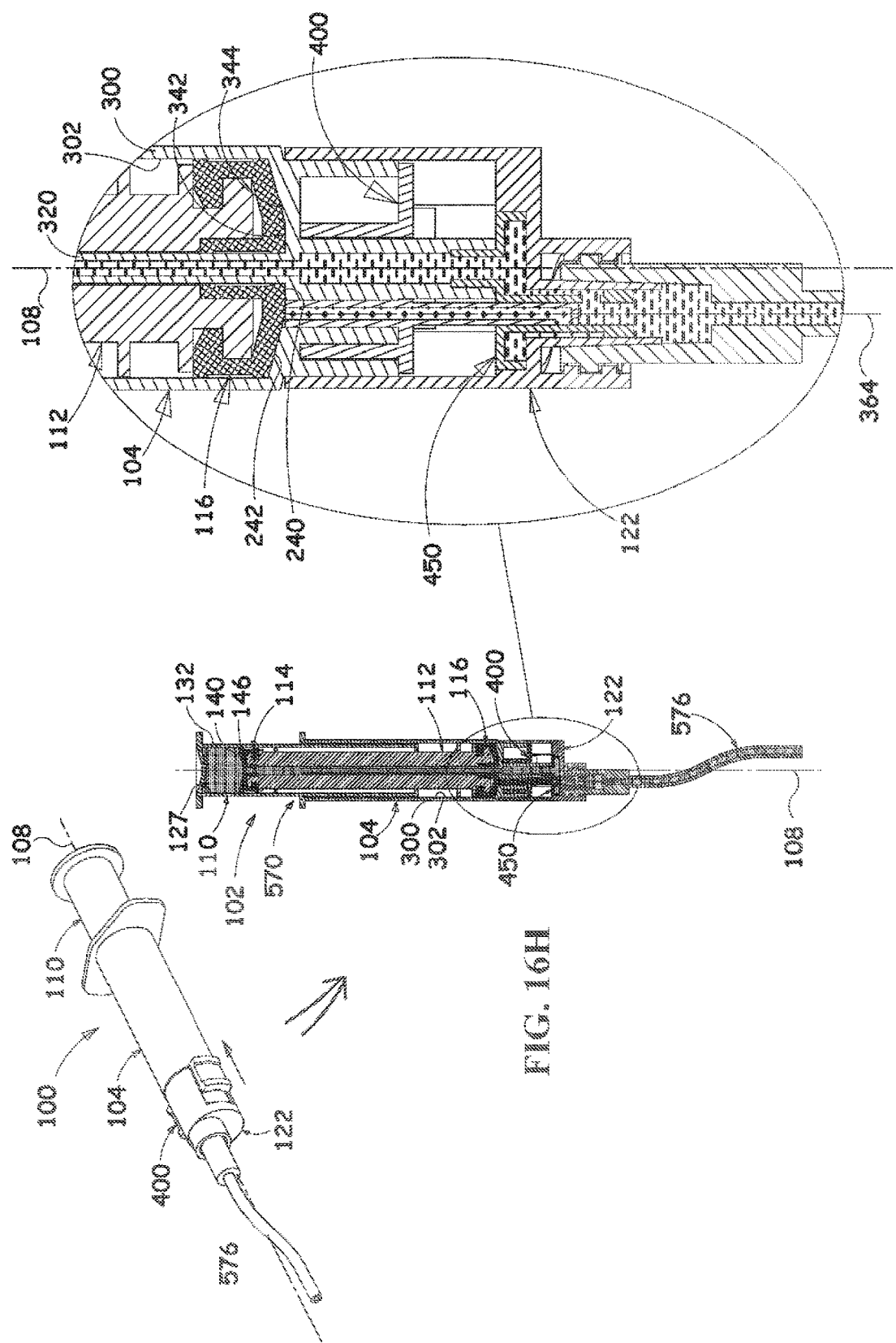
FIG. 16H is a simplified combined pictorial and sectional view illustration of the multi-chamber syringe in an eighth operative state, which is preferably the state in which the multi-chamber syringe has completed injection of the medication into the catheter and injects flushing solution into the catheter.

Reference is now made to FIG. 16H, which illustrates the multi-chamber syringe 100 in an eighth operative state, which is preferably the state in which the multi-chamber syringe 100 completes injection of the medication into the catheter 576, and both piston assembly housing portion 110 and the plunger sub-assembly 570 of the piston assembly 102 are further pushed forwardly relative to barrel 104 and thereafter the axially displaceable element 400 is shifted to its second orientation.

As compared with the arrangement shown in FIG. 16G, here forward-facing end portion 120 of the plunger rod 112 with the piston ring 116 mounted thereon return to the first position defined by engagement of forward flat surface 240 and tapered ring surface 242 of the piston ring 116 with the rearward facing surface 342 and tapered surface 344 of the barrel 104 respectively, as shown in FIG. 16A.

The piston assembly housing portion 110 of piston assembly 102 is in a partially inserted orientation with respect to the remainder of piston assembly 102 and specifically displaced forwardly with respect to piston ring 114.

In the eighth operative state, due to the further forward displacement of piston assembly housing portion 110 in the barrel 104:

the second fluid volume is decreased relative to its state in the seventh operative state and at least a portion of the portion of the second fluid volume defined by surface 140 of flange 146 of rearward piston 114; and surfaces 127 and 132 of the piston assembly housing portion 110 is thereby eliminated, with the result that the flushing solution that had earlier been aspirated from the flushing solution vial 574 is injected into the catheter 576.

Figure 16I:
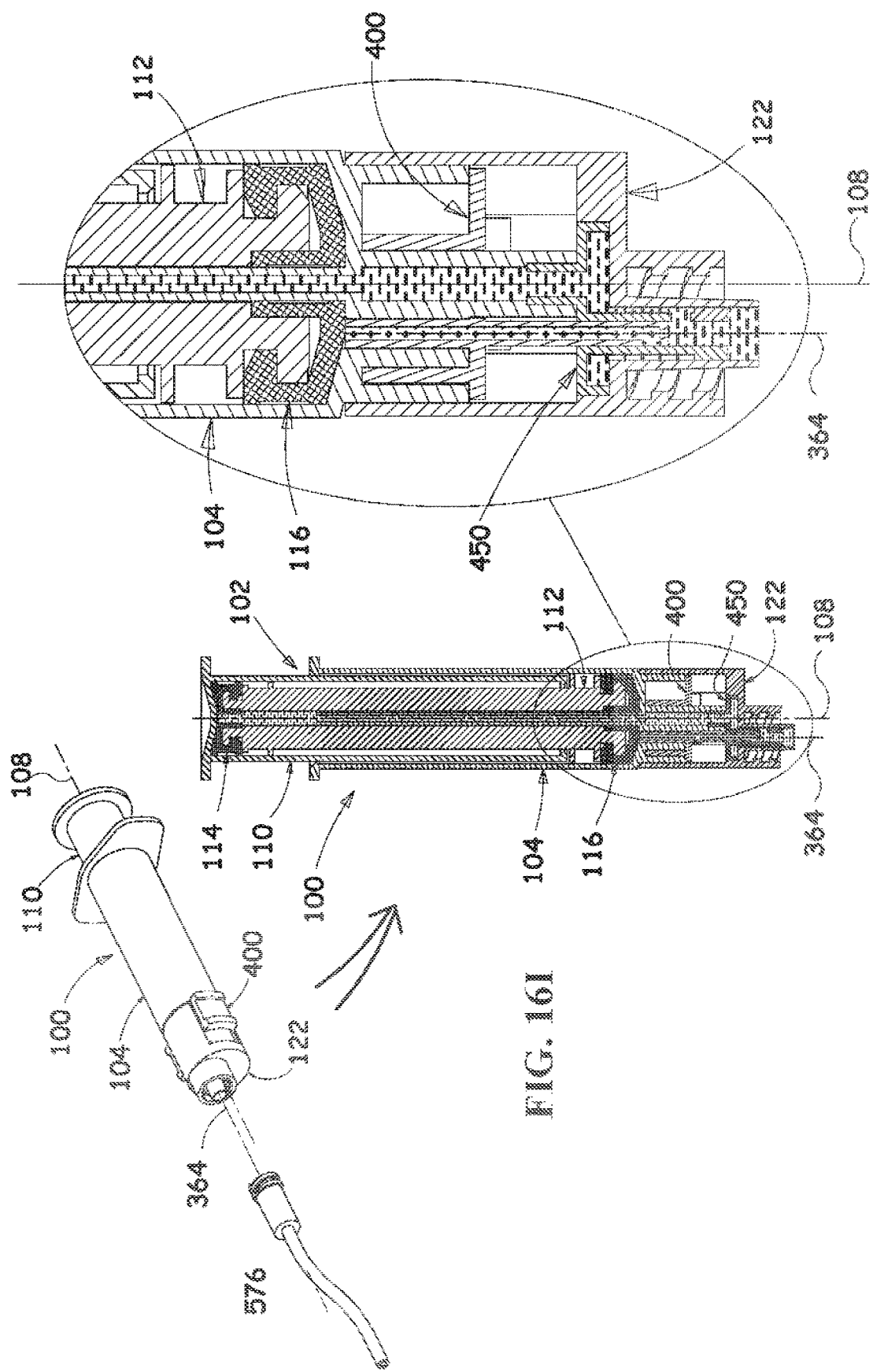
FIG. 16I is a simplified combined pictorial and sectional view illustration of the multi-chamber syringe in a ninth operative state, which is preferably the state in which the multi-chamber syringe is decoupled from the catheter.

Reference is now made to FIG. 16I, which illustrates the multi-chamber syringe 100 in a ninth operative state, which is preferably the state in which the multi-chamber syringe 100 is decoupled from the catheter 576 and the axially displaceable element 400 remains in its second orientation. It is a particular feature of this embodiment of the present invention that at this final operative stage, the outlet defined by surface 493 of bore 492 of flow channel 490 of the luer connector portion 122 has been flushed with flushing solution.

The fact that the outlet of the multi-chamber syringe 100 is flushed with flushing solution at the final operative state enables safe disposal of the syringe 100. It is noted that the entire piston assembly 102 is in its original orientation as shown in FIG. 16A.

Figure 18A:
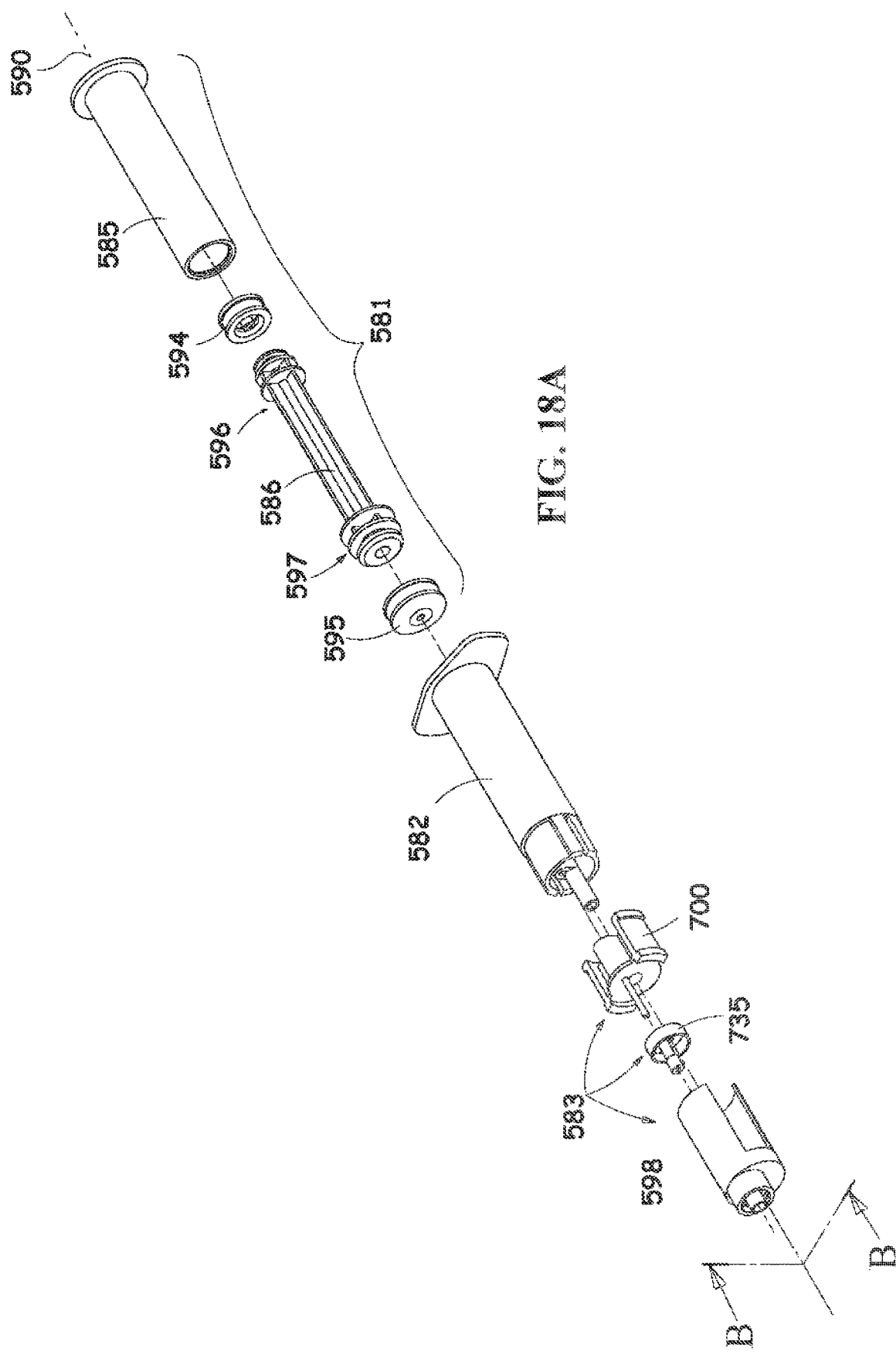
FIG. 18A is a simplified exploded view illustration of the multi-chamber syringe of FIG. 17A.
Figure 18B:
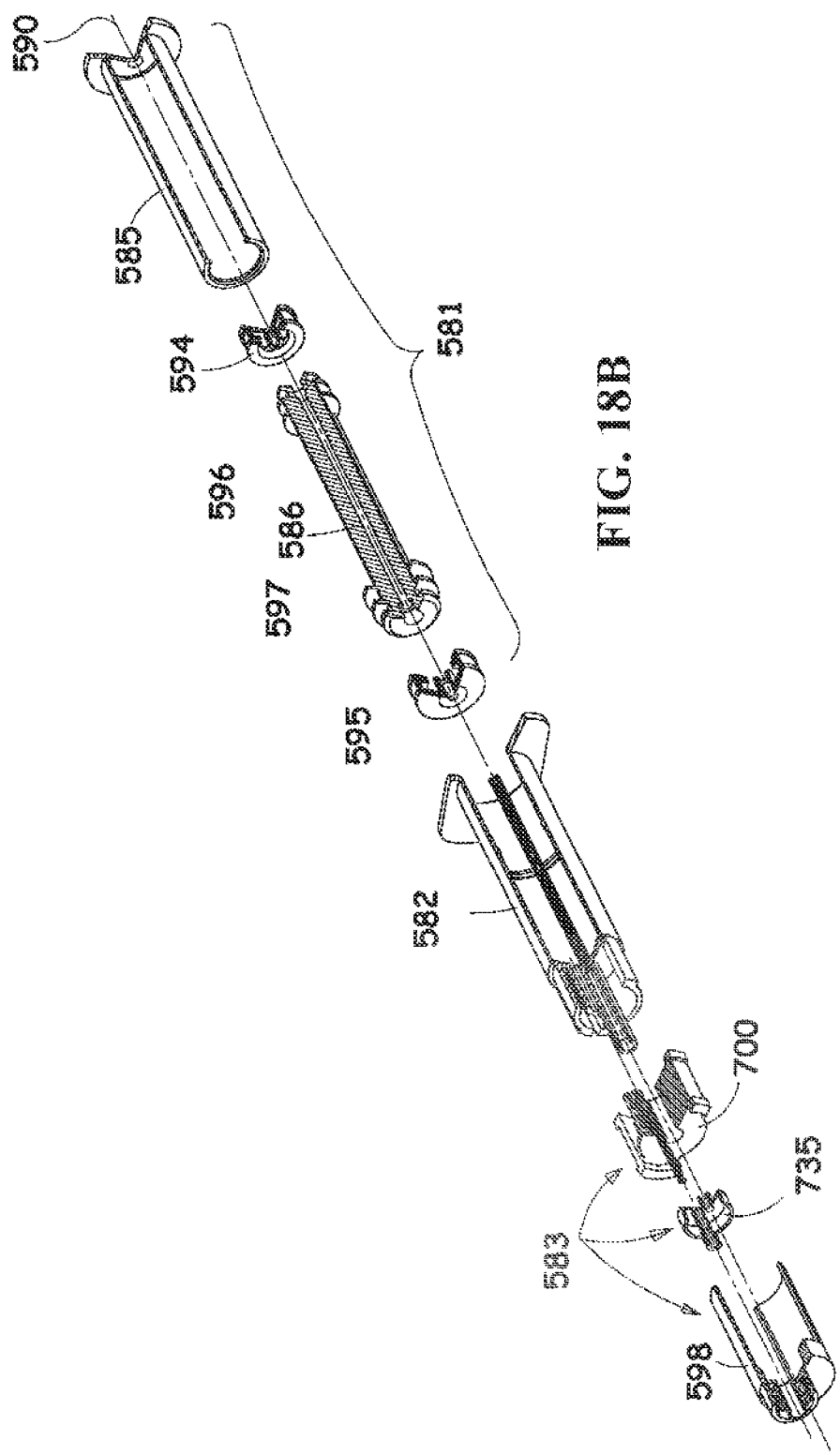
FIG. 18B is a simplified exploded illustration of the multi-chamber syringe of FIG. 18A partially cut away to show the internal structure thereof.
Figure 21D:
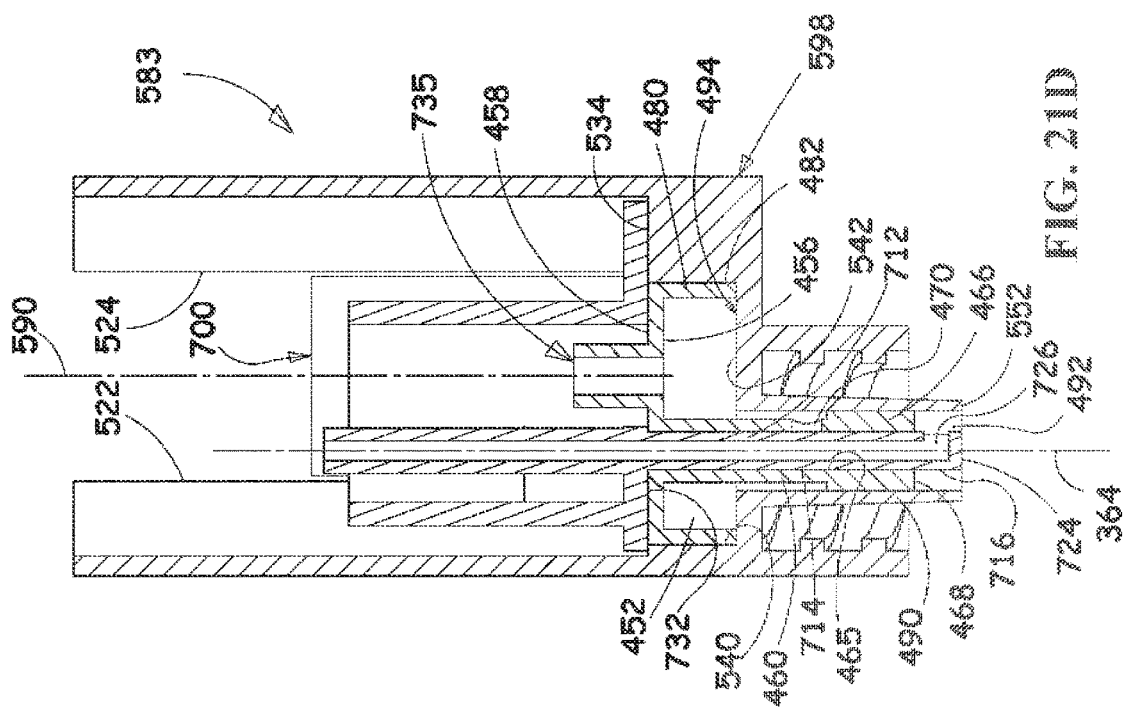
FIGS. 21C & 21D are simplified respective cut away and sectional views of the valve assembly of FIGS. 21A & 21B, shown in the first operative valve assembly orientation.
Figure 21C:
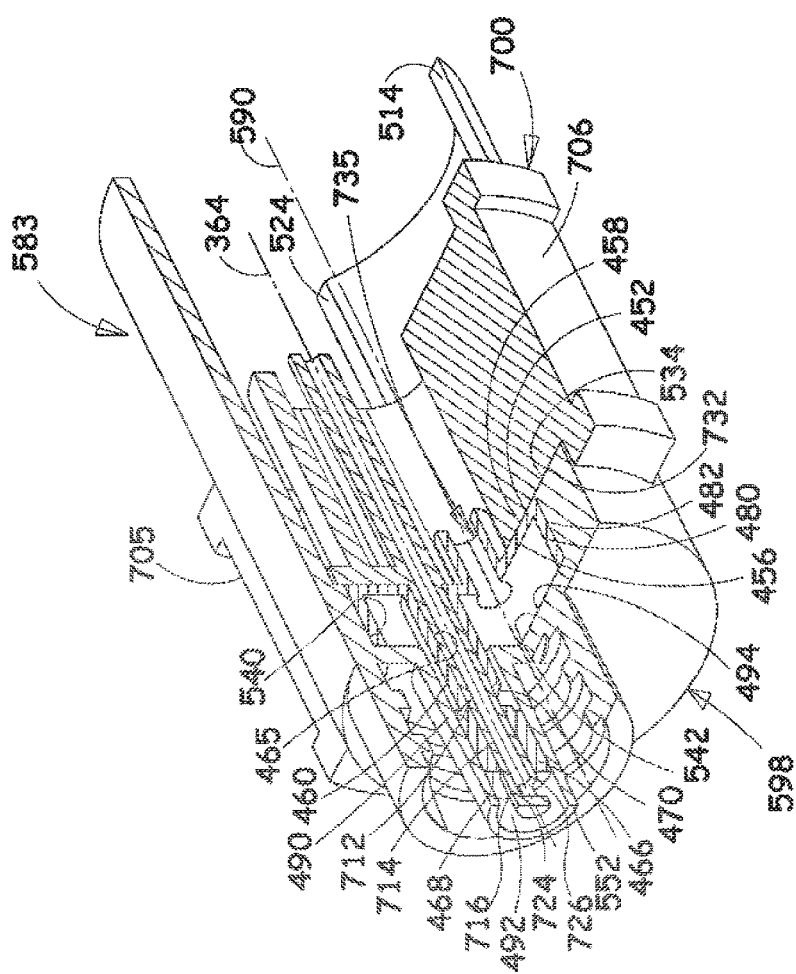
Figure 24C:
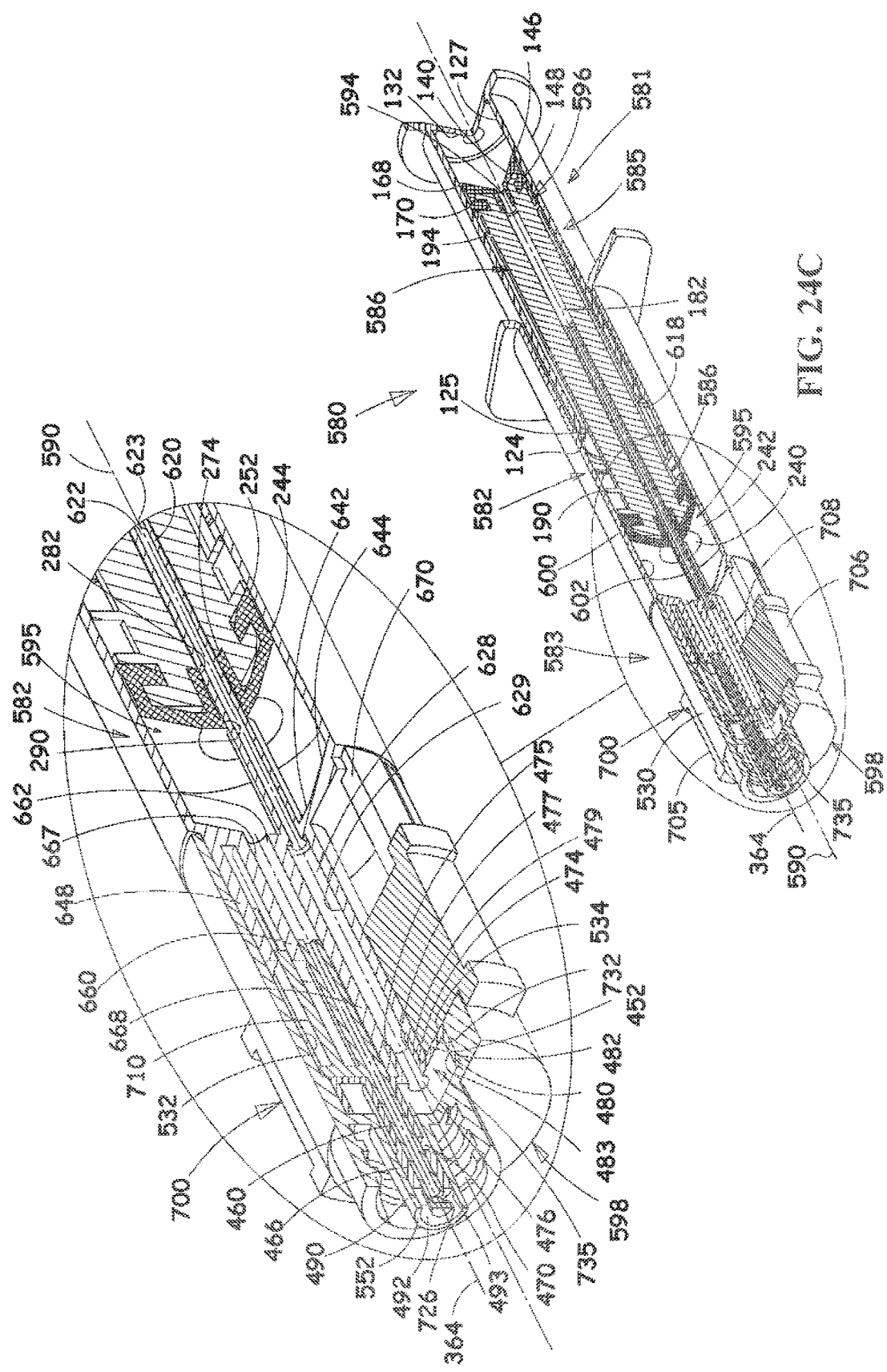
FIGS. 24C & 24D are simplified respective cut-away and sectional views of the assembled multi-chamber syringe of FIGS. 17A-18B, shown in the first operative syringe orientation.
Figure 24D:
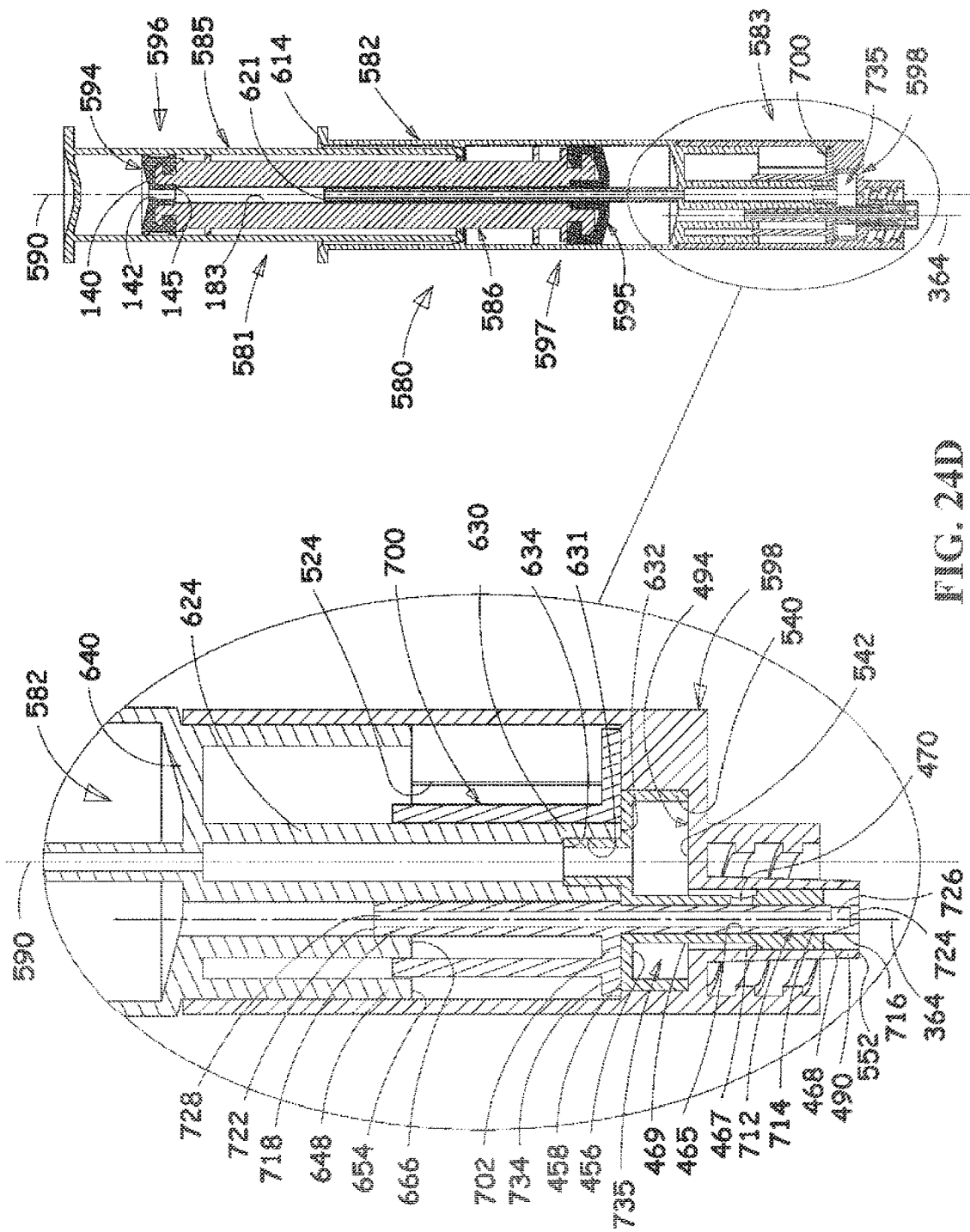
Figure 25C:
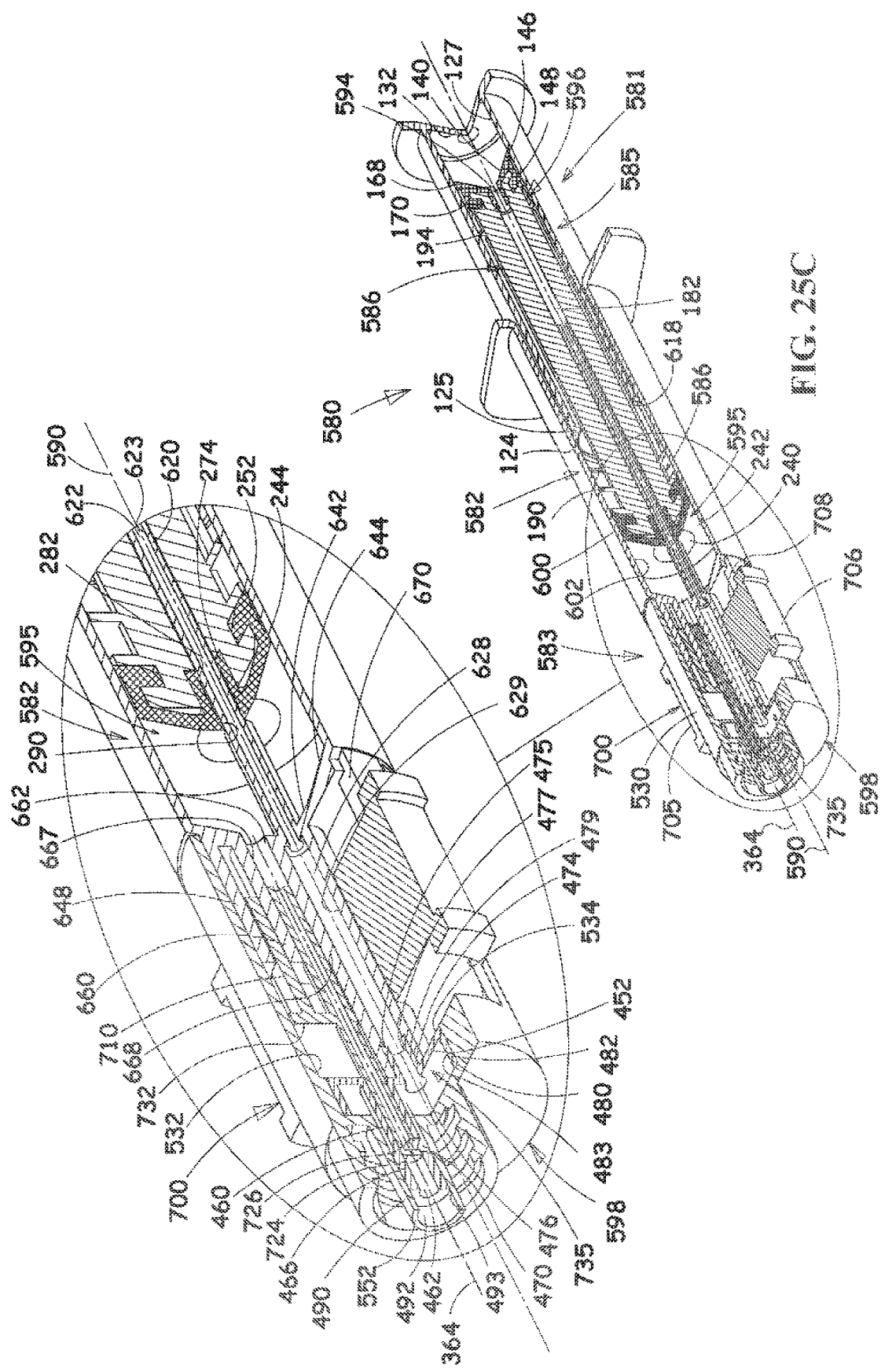
FIGS. 25C & 25D are simplified respective cut-away and sectional views of the assembled multi-chamber syringe of FIGS. 17A-18B, shown in the intermediate operative syringe orientation.
Figure 25D:
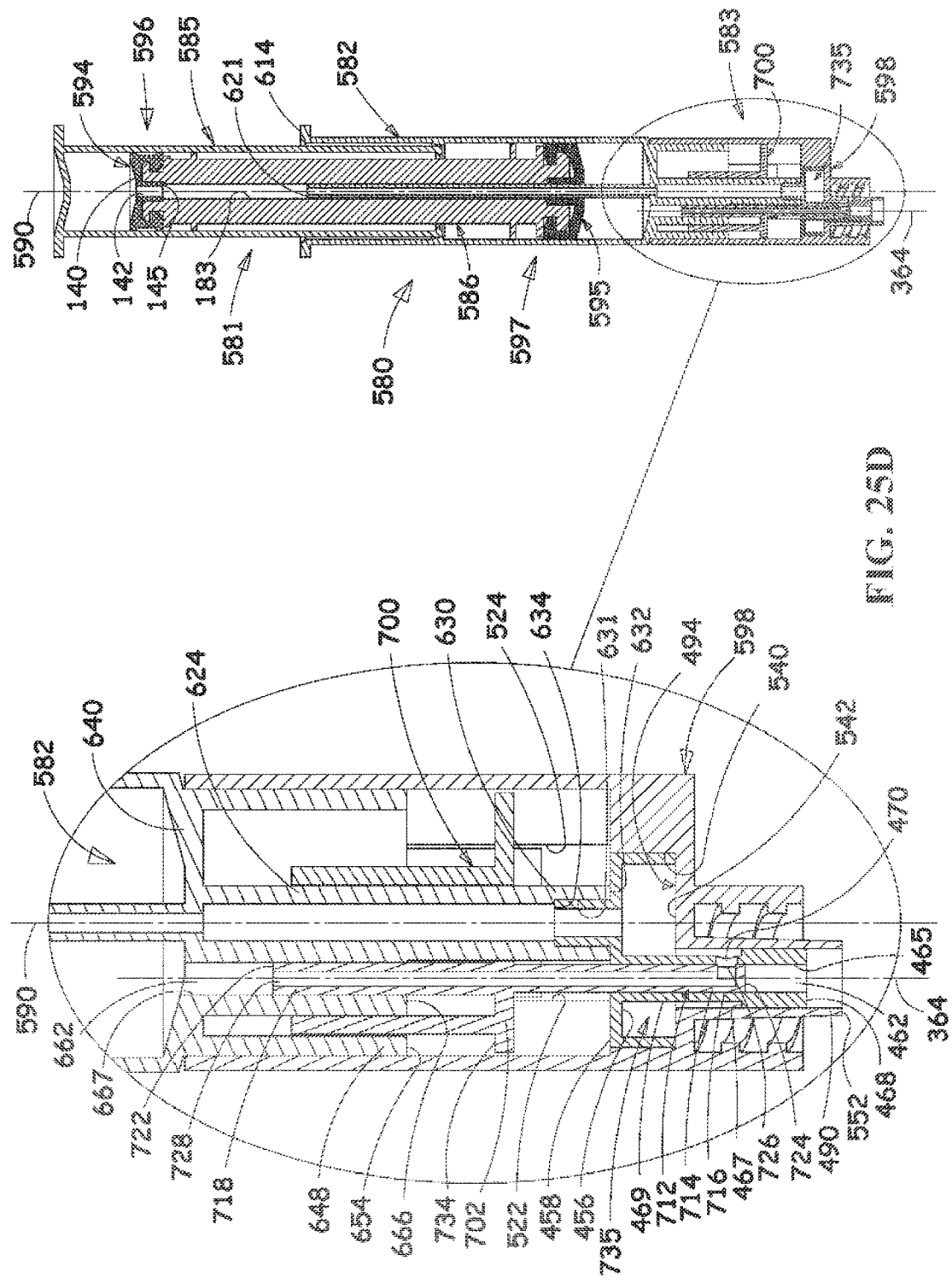

Reference is now made to FIG. 17A, which is a simplified pictorial illustration of a multi-chamber syringe constructed and operative in accordance with another embodiment of the invention and to FIG. 17B, which is a simplified pictorial illustration of the multi-chamber syringe of FIG. 17A, which is partially cut away to show the internal structure thereof. Reference is additionally made to FIG. 18A, which is a simplified exploded-view illustration of the multi-chamber syringe of FIG. 17A and to FIG. 18B, which is a simplified exploded illustration of the multi-chamber syringe of FIG. 18A, which is partially cut away to show the internal structure thereof.

As will be described in greater detail hereinbelow, the multi-chamber syringe includes at least two separate fluid containers, at least two selectably openable fluid communication pathways associated with the fluid containers and a selector switch assembly that is operative to selectively fluidly interconnect either the first fluid container or the second fluid container with a syringe fluid flow passageway. Preferably, the selector switch assembly prevents simultaneous interconnection of both the first fluid container and the second fluid container with the syringe fluid flow passageway. Most preferably, at no point in time are both the first fluid container and the second fluid container interconnected with a syringe fluid flow passageway.

A multi-chamber syringe 580 preferably includes a piston assembly 581, which may be identical to piston assembly 102 (FIGS. 1A-6C) and forms at least part of the second fluid container, a barrel 582 which forms at least part of the first fluid container and a valve assembly 583 which forms at least part of the selector switch assembly, which are preferably mutually aligned along a longitudinal axis 584. Piston assembly 581 and barrel 582 are arranged for mutual telescopic displacement along longitudinal axis 584.

The piston assembly 581 includes a piston assembly housing portion 585 and a plunger rod 586, which is partially disposed within piston assembly housing portion 585 and is slidable with respect thereto along longitudinal axis 590 within predetermined axial limits. Rearward and forward piston rings 594 and 595 are mounted on respective rearward and forward ends 596 and 597 of plunger rod 586 for axial displacement together with plunger rod 586 in fluid sealing engagement with an interior cylindrical surface of piston assembly housing portion 585.

Valve assembly 583 includes a luer connector portion 598 for operative engagement with any suitable medical device, such as a catheter, a vial adaptor or an IV set.

Reference is now made to FIGS. 19A-19E, which are simplified illustrations of the barrel of the multi-chamber syringe of FIGS. 17A-18B.

Barrel 582 is preferably integrally formed of plastic, such as polyethylene or polypropylene and is 180 degree side-to-side symmetric about axis 584.

As seen in FIGS. 17A-17E, barrel 582 includes a circular cylindrical chamber 600 having a circular cylindrical inner surface 602 and a circular cylindrical outer surface 604. A pair of generally flat protrusions 606 extend radially outwardly from cylindrical outer surface 604 at a rearward end of chamber 600 and together define a circumferential edge surface 608, a forwardly facing surface 610 having a rearwardly-facing tapered ring surface 612, surrounding the rear end of chamber 600 and a corresponding rearwardly facing surface 614.

An inwardly facing plunger rod rearward motion limiting flange 616 is located forwardly of protrusions 606 and includes a rearwardly-facing tapered ring surface 617 which terminates forwardly in a narrow cylindrical ring surface 618. A forwardly-facing shoulder 619 is defined between ring surface 618 and cylindrical inner surface 602. The location of inwardly facing plunger rod rearward motion limiting flange 616 limits the amount of reconstituting solution which can be employed in reconstituting a medicament and thus the location of flange 616 is preferably selected in accordance with a desired concentration of medicament.

Arranged along the radial center of chamber 600 is an internal channel member 620 having an edge surface 621 defining an opening of a throughgoing internal bore 622 having an inner cylindrical surface 623. At a forward end thereof, internal bore communicates with the interior of a generally cylindrical forward channel portion 624, which is coaxial therewith along axis 590. Forward channel portion 624 has an internal bore 626, which includes a rearward portion 628, having an inner cylindrical surface 629 and having an inner radius substantially greater than that of bore 622, and a forward portion 630, having an inner cylindrical surface 631 and having an inner radius somewhat greater than that of rearward portion 628. Forward channel portion 624 has a forward end surface 632 and an intermediate forward facing shoulder surface 634 between bore portions 628 and 630.

Circular cylindrical inner surface 602 terminates at a forward end of circular cylindrical chamber 600 in a rearward facing bulkhead 640 having a central flat rearward facing surface 642 surrounding a forward end of internal channel member 620. Extending rearwardly and radially outward from surface 642 is a tapered surface 644 which terminates at a forward end of circular cylindrical inner surface 602.

Bulkhead 640 defines a flat forward-facing surface 646 which terminates in an axially slotted generally cylindrical wall 648. Generally cylindrical wall 648 defines an outer cylindrical wall surface 650 and an inner cylindrical wall surface 652 which terminate forwardly at a forward edge surface 654. It is noted that forward channel portion 624 extends forwardly of forward edge surface 654.

An additional channel portion 660 extends forwardly from bulkhead 640 and includes a bore 662 which extends along an axis 364 through bulkhead 640 and communicates with the interior of chamber 600. Bore 662 terminates forwardly at a forward edge surface 666 thereof, which is preferably coplanar with edge surface 654. Bore 662 defines a cylindrical surface 667.

Channel portion 624 and additional channel portion 660 together define an obround cylindrical surface 668.

Generally cylindrical wall 648 is provided with a pair of axially extending slots 670, which are mutually separated by 180 degrees with respect to axis 590. Generally cylindrical wall is provided with a pair of enhanced thickness wall portions 672 which extends along both sides of each of slots 670.

Reference is now made to FIGS. 20A-20D, which are simplified illustrations of an axially displaceable element 700 forming part of the valve assembly 583 of the multi-chamber syringe 580 of FIGS. 17A-18B.

As seen in FIGS. 20A-20D, element 700 is preferably integrally formed of plastic, such as polyethylene or polypropylene and is 180 degree side-to-side symmetric about axis 590.

Element 700 preferably includes a flat apertured disc portion 702 arranged such that axis 590 extends though the center of an aperture 704 formed therein. Disposed axially outwardly of disc portion 702 are a pair of mutually 180 degree spaced finger grip portions designated by reference numerals 705 and 706, which are joined together and to disc portion 702 by vanes 708. As seen with particularity in FIG. 18B, vanes 708 extend outwardly from a cylindrical portion 710, having an obround cross section, which portion 710 extends rearwardly from disc portion 702. Cylindrical portion 710 defines a bore 711, having an obround cross section.

A generally circular cylindrical cannula portion 712 extends forwardly and rearwardly of disc portion 702. A forward portion 714 of cannula portion 712 has an outer cylindrical surface 716 and has an outer diameter, which is slightly less than the outer diameter of a rearward portion 718, having an outer cylindrical surface 720. Cannula portion 712 is arranged to extend along axis 364 (FIGS. 17A-17E) and extends through and slight rearwardly of cylindrical portion 710, terminating in an open back end having an end surface 722.

Forward portion 714 is slightly longer than rearward portion 718 and has a closed forward end having an end surface 724 and a side aperture 726 just rearward of end surface 724, which side aperture is preferably directed in a direction facing axis 590. Cannula portion 712 is formed with an axial bore 728 extending from end surface 722 along axis 364 to aperture 726. Cylindrical portion 710 and vanes 708 preferably have a mutually coplanar rearward facing edge 730. Flat apertured disc portion 702 has a forward facing surface 732 and a rearward facing surface 734.

Reference is now made to FIGS. 21A-21D, which illustrate valve assembly 583 of the multi-chamber syringe 580, which assembly includes axially displaceable element 700 (FIGS. 20A-20D), a static element 735, which may be identical to static element 735 (FIGS. 9A-9D) and luer connector portion 598, which may be identical to luer connector portion 122 (FIGS. 10A-10D), in a first operative valve assembly orientation.

Thereafter, reference will be made to FIGS. 22A-22C, which illustrate the valve assembly 583 in an intermediate operative valve assembly orientation and additionally to FIGS. 23A-23C, which illustrate the valve assembly 583 in a second operative valve assembly orientation.

It is appreciated that in the first, the intermediate and the second operative valve assembly orientations shown respectively in FIGS. 21A-21D, 22A-22C and 23A-23C, the following spatial relationships exist between the various elements:

Grip portion 705 of axially displaceable element 700 is positioned between side edges 522 and 524 (FIGS. 10A-10D) of luer connector portion 598 and grip portion 706 is positioned between side edges 512 and 514 (FIGS. 10A-10D) of luer connector portion 598;

Disc portion 452 (FIGS. 9A-9D) of the static element 735 is positioned within recess 494 (FIGS. 10A-10D) of the luer connector portion 598, in a manner that the outwardly facing surface 482 (FIGS. 9A-9D) of circumferential wall 480 (FIGS. 9A-9D) of static element 735 tightly and fluid sealingly fits cylindrical surface 540 (FIGS. 10A-10D) of recess 494;

Forward facing flat surface 456 (FIGS. 9A-9D) of disc portion 452 of static element 735 is spaced apart from the rearward facing flat surface 542 (FIGS. 10A-10D) of recess 494 of luer connector portion 598;

Forward flow channel portion 460 (FIGS. 9A-9D) of static element 735 is partially inserted into flow channel 490 (FIGS. 10A-10D) of the luer connector portion 598, such that thickened forward portion 466 (FIGS. 9A-9D) of forward flow channel portion 460 of static element 735 is fluid sealingly arranged within bore 492 (FIGS. 10A-10D) of flow channel 490 of the luer selector portion 598 and the forward edge 468 (FIGS. 9A-9D) of forward flow channel portion 460 is positioned rearwardly of forward facing edge 552 (FIGS. 10A-10D) of flow channel 490 of the luer connector portion 598;

Cannula portion 712 of the axially displaceable element 700 is slidably fluid sealingly engaged with surface 465 (FIGS. 9A-9D) of bore 462 (FIGS. 9A-9D) of forward flow channel portion 460 of static element 735; and The side opening 470 (FIGS. 9A-9D) of forward flow channel portion 460 of static element 735 and aperture 726 of cannula portion 712 of the axially displaceable element 700 face in the same direction.

In the first operative valve assembly orientation, shown in FIGS. 21A-21D, the axially displaceable element 700 is positioned in a first orientation relative to static element 735 and luer connector portion 598. Specifically forward facing surface 732 of the axially displaceable element 700 is positioned rearwardly of and abutting flat wall surface 534 (FIGS. 10A-10D) of the luer connector portion 598.

The rearward facing flat surface 458 (FIGS. 9A-9D) of disc portion 452 is located forwardly of and abutting forward facing surface 732 of the axially displaceable element 700.

End surface 724 of cannula portion 712 is positioned forwardly of forward edge 468 of forward flow channel portion 460 of static element 735, at a location that does not block aperture 726 of the cannula 712. Accordingly, aperture 726 of cannula portion 712 of axially displaceable element 700 is open.

The side opening 470 of forward flow channel portion 460 of static element 735 is sealed closed by fluid sealing engagement of outer cylindrical surface 716 of forward portion 714 of axially displaceable element 700 with surface 465 of cylindrical bore 462 of forward flow channel portion 460 of static element 735.

In the intermediate operative valve assembly orientation, shown in FIGS. 22A-22C, the axially displaceable element 700 is positioned in an intermediate orientation relative to the static element 735 and luer connector portion 598. Specifically forward facing surface 732 of the axially displaceable element 700 is positioned rearwardly of and spaced from flat wall surface 534 of the luer connector portion 598.

The rearward facing flat surface 458 of disc portion 452 is spaced forwardly from forward facing surface 732 of the axially displaceable element 700.

End surface 724 of cannula portion 712 is positioned slightly forwardly of side opening 470 of forward flow channel portion 460 of static element 735.

Aperture 726 of cannula portion 712 of axially displaceable element 700 is open to side opening 470 of forward flow channel portion 460 of static element 735.

Fluid sealing engagement remains between outer cylindrical surface 716 of forward portion 714 of axially displaceable element 700 with surface 465 of cylindrical bore 462 of forward flow channel portion 460 of the static element 735.

In the second operative valve assembly orientation, shown in FIGS. 23A-23C, the axially displaceable element 700 is positioned in a second orientation relative to static element 735 and luer connector portion 598. Specifically forward facing surface 732 of the axially displaceable element 700 is positioned more rearwardly of and spaced from flat wall surface 534 of the luer connector portion 598.

The rearward facing flat surface 458 of disc portion 452 is spaced more forwardly from forward facing surface 732 of the axially displaceable element 700.

End surface 724 of cannula portion 712 is positioned rearwardly of side opening 470 of forward flow channel portion 460 of the static element 735. Accordingly, the side opening 470 of forward flow channel portion 460 of static element 735 is open.

Aperture 726 of cannula portion 712 of axially displaceable element 700 is closed by fluid sealing engagement of outer cylindrical surface 716 of forward portion 714 of axially displaceable element 700 with surface 465 of cylindrical bore 462 of forward flow channel portion 460 of static element 735.

Reference is now made to FIGS. 24A-24D, which illustrate the multi-chamber syringe 580 in a first operative syringe orientation. Thereafter, reference is made to FIGS. 25A-25D, which illustrate the multi-chamber syringe 580 in an intermediate operative syringe orientation and additionally reference is made to FIGS. 26A-26D, which illustrate the multi-chamber syringe 580 in a second operative syringe orientation.

It is appreciated that in the first, the intermediate and the second operative syringe orientations shown respectively in FIGS. 24A-24D, 25A-25D & 26A-26D, the following spatial relationships exist between the various elements:

The rearward-facing end portion 596 of the plunger rod 586 is inserted into the piston assembly housing portion 585, in a manner that outer cylindrical surfaces 168 and 170 (FIGS. 4A-4C) of rearward-facing and forward-facing flanges 146 and 148 (FIGS. 4A-4C) of the piston ring 594 (FIGS. 4A-4C) are sealingly slidably arranged within interior surface 127 (FIGS. 3A & 3B) of piston assembly housing portion 585;

The forward-facing end portion 597 of the plunger rod 586 is inserted into the barrel 582 in a manner that radially outward facing surfaces 244 and 252 (FIGS. 6A-6C) of the piston ring 595 are sealingly slidably arranged within cylindrical inner surface 602 of circular cylindrical chamber 600 of barrel 582;

The rearward-facing end portion 596 of the plunger rod 586 and the piston ring 594 mounted thereon are slidably movable within piston assembly housing portion 585 from a first position to a second position. The first position is defined by engagement of forward-facing surface 132 (FIGS. 3A & 3B) of the piston assembly housing portion 585 with rearward facing recess 140 (FIGS. 4A-4C) of the piston ring 594. The second position is defined by engagement of rearward flange 194 (FIGS. 5A-5C) of the plunger rod 586 with inwardly directed flange 125 (FIGS. 3A & 3B) of the piston assembly housing portion 585;

The forward-facing end portion 597 of the plunger rod 586 with the piston ring 595 mounted thereon are slidably movable within barrel 582 from a first position to a second position. The first position is defined by engagement of forward flat surface 240 and tapered ring surface 242 of the piston ring 595 with the rearward facing surface 642 and tapered surface 644 of the barrel 582 respectively. The second position is defined by engagement of forward flange 190 of the plunger rod 586 with forwardly facing shoulder 619 of barrel 582;

Internal channel member 620 of barrel 582 is inserted into axial bore 182 (FIGS. 5A-5C) of the plunger rod 586 through circular cylindrical portion 274 of the piston ring 595. It is appreciated that internal channel member 620 of the barrel 582 is sealingly slidably arranged within the circular cylindrical portion 274 of the piston ring 595 due to engagement of the internal channel member 620 with inwardly-facing surfaces 282 and 290 of the circular cylindrical portion 274 of the piston ring 595;

The outer circumference of rearward flange 194 of plunger rod 586 substantially corresponds to internal surface 127 of the piston assembly housing portion 585. The outer circumference of the forward flange 190 of plunger rod 586 substantially corresponds to inner surface 602 of the barrel 582;

When the piston ring 594 and the piston ring 595 are both positioned in the first position, the piston assembly housing portion 585 is partially inserted into the barrel 582. When the piston rings 114 and 116 are both positioned in the second position, the forward end 124 (FIGS. 3A & 3B) of piston assembly housing portion 585 is rearwardly spaced apart from rearward end 614 of barrel 582;

The valve assembly 583 is attached to the barrel 582, preferably by heat welding and alternatively by use of an adhesive or via a snap-fit arrangement. Inner cylindrical wall surface 532 of outer cylindrical wall surface 530 (FIGS. 10A-10D) of luer connector portion 598 is preferably attached to slotted cylindrical wall 648 of barrel 582;

The obround cylindrical surface 668 of barrel 582 is at least partially inserted into a corresponding obround cylindrical portion 710 of axially displaceable element 700. Flow channel portion 474 (FIGS. 9A-9D) of static element 735 is inserted into forward portion 630 of the forward channel portion 624 of barrel 582 such that surface 479 of flow channel portion 474 (FIGS. 9A-9D) fluid sealingly engages surface 630 of forward channel portion 624. A rearward end of flow channel portion 474 abuts forward facing ring portion 634 of forward flow channel portion 624. Rearward facing flat surface 458 of static element 735 abuts forward end surface 632 of barrel 582;

Rearward portion 718 of cannula portion 712 of axially displaceable element 700 is at least partially inserted into bore 662 of channel portion 660 of barrel 582 in a slidably fluid sealing manner;

Vanes 708 of the axially displaceable element 700 are at least partially inserted into axially extending slots 670 of the barrel 582;

Grip portion 705 of axially displaceable element 700 is positioned between side edges 512 and 514 of luer connector portion 598 and grip portion 706 is positioned between side edges 522 and 524 of luer connector portion 598;

The disc portion 452 of the static element 735 is positioned within the recess 494 of the luer connector portion 598, in a manner that the outwardly facing surface 482 of circumferential wall 480 of static element 735 tightly and fluid sealingly fits cylindrical surface 540 of recess 494;

Forward facing flat surface 456 of the disc portion 452 of static element 735 is spaced apart from the rearward facing flat surface 542 of recess 494 of luer connector portion 598;

Forward flow channel portion 460 of static element 735 is inserted into flow channel 490 of the luer connector portion 598, such that thickened forward portion 466 of forward flow channel portion 460 of static element 735 is fluid sealingly arranged within bore 492 of flow channel 490 of the luer connector portion 598 and the forward edge 468 of forward flow channel portion 460 is positioned rearwardly from forward facing edge 552 of flow channel 490 of the luer connector portion 598;

Cannula portion 712 of the axially displaceable element 700 is fluid sealingly fitted within forward flow channel portion 460 of static element 735; and The side opening 470 of forward flow channel portion 460 of the static element 735 and aperture 726 of cannula portion 712 of the axially displaceable element 700 face in the same directions.

In the first operative syringe orientation, the rearward portion 718 of cannula portion 712 of the axially displaceable element 700 is sealingly inserted through bore 662 of channel portion 660 of the barrel 582, in a manner that end surface 722 of cannula portion 712 is forwardly spaced apart from flat rearward facing surface 642 of bulkhead 640 of barrel 582.

Rearward facing surface 734 of disc portion 702 of the axially displaceable element 700 forwardly spaced from forward edge surface 654 of cylindrical wall 648 and forward edge surface 666 of additional channel portion 660 of barrel 582.

The axially displaceable element 700 is selectively positioned in the first orientation relative to static element 735 and luer connector portion 598. Specifically forward facing surface 732 of the axially displaceable element 700 is positioned rearwardly of and abutting flat wall surface 534 of the luer connector portion 598.

The rearward facing flat surface 458 of disc portion 452 is located forwardly of and abutting forward facing surface 732 of the axially displaceable element 700.

End surface 724 of cannula portion 712 is positioned forwardly of side opening 470 of forward flow channel portion 460 of static element 735.

The side opening 470 of forward flow channel portion 460 of static element 735 is closed by fluid sealing engagement of outer cylindrical surface 716 of forward portion 714 of axially displaceable element 700 with cylindrical bore 462 of forward flow channel portion 460 of static element 735.

Aperture 726 of cannula portion 712 of axially displaceable element 700 is open.

Cylindrical portion 710 of the axially displaceable element 700 surrounds rearward flow channel portion 474 of static element 735.

End surface 724 of cannula portion 712 of element 700 is coplanar with forward facing edge 552 of flow channel 490 of luer connector portion 598.

In this first operative syringe orientation the following relationships exist between fluid volumes:

A first fluid volume is defined by surfaces 602, 620, 642, 644 of chamber 600; surface 667 of bore 662 of barrel 582; surface 722, aperture 726 and bore 728 of cannula 712 of the axially displaceable element 700; and surfaces 240 and 242 of piston ring 595.

In the first operative syringe orientation, the first fluid volume defined hereinabove is in open communication with an outlet, which forms part of the syringe fluid flow passageway and is defined by surface 493 of bore 492 of flow channel 490 of the luer connector portion 598.

A second fluid volume is defined by surface 465, side opening 470, shoulder surface 467 and surface 469 of flow channel 460; surface 456 of disc portion 452; surface 483 of peripheral wall 480; surfaces 475 and 477 of bore 476 of rearward flow channel 474 of static element 735; surface 724 of axially displaceable element 700; and inner cylindrical surface 629 of portion 628 of channel portion 624; surfaces 621 and 623 associated with bore 622; surface 183 of bore 182 of the plunger rod 112; surface 145 associated with bore 142, surface 140 of flange 146 of rearward piston 114; and surfaces 127 and 132 of piston assembly housing portion 585.

In the first operative syringe orientation, the second fluid volume defined hereinabove is sealed by closing of aperture 470 produced by sealing engagement of outer surface 716 of cannula 712 with inner surface 465 of flow channel 460.

Reference is now made to FIGS. 25A-25D, which illustrate the multi-chamber syringe 580 in an intermediate operative syringe orientation.

In the intermediate operative syringe orientation, shown in FIGS. 25A-25D, the rearward portion 718 of cannula portion 712 of the axially displaceable element 700 is sealingly inserted through bore 662 of channel portion 660 of the barrel 582, in a manner that end surface 722 of cannula portion 712 is less forwardly spaced from flat rearward facing surface 642 of bulkhead 640 of barrel 582.

Rearward facing surface 734 of disc portion 702 of the axially displaceable element 700 less forwardly spaced from forward edge surface 654 of cylindrical wall 648 and forward edge surface 666 of additional channel portion 660 of barrel 582.

The axially displaceable element 700 is selectively positioned in the intermediate position relative to static element 735 and luer connector portion 598. Specifically forward facing surface 732 of the axially displaceable element 700 is positioned rearwardly of and spaced from flat wall surface 534 of the luer connector 598.

The rearward facing flat surface 458 of disc portion 452 is spaced forwardly from forward facing surface 732 of the axially displaceable element 700.

End surface 724 of cannula portion 712 is positioned slightly forwardly of side opening 470 of forward flow channel portion 460 of static element 735.

Aperture 726 of cannula portion 712 is open to the side opening 470 of forward flow channel portion 460 of static element 735. Sealing engagement remains between outer cylindrical surface 716 of forward portion 714 of axially displaceable element 700 with inner surface 465 of cylindrical bore 462 of forward flow channel portion 460 of static element 735.

In this intermediate operative syringe orientation the following relationships exist between the first and second fluid volumes:

The first fluid volume is sealed from the outlet, which forms part of the syringe fluid flow passageway and is defined by surface 493 of bore 492 of flow channel 490 of the luer connector portion 598 by virtue of the fact that outer cylindrical surface 716 of cannula portion 712 of axially displaceable element 700 sealingly engages inner surface 465 of cylindrical bore 462 of forward flow channel portion 460 of static element 735.

The second fluid volume communicates with the first fluid volume, defined by rearwardly facing surface 542 of recess 494 and surface 493 of bore 492 of flow channel 490 of the luer connector portion 598 via outer cylindrical surface 469, rearwardly facing shoulder 467 and side opening 470 of static element 735 by virtue of the fact that aperture 726 of cannula portion 712 communicates with side opening 470 of forward flow channel portion 460 of static element 735.

Reference is now made to FIGS. 26A-26D, which illustrate the multi-chamber syringe 580 in a second operative syringe orientation.

In the second operative syringe orientation, shown in FIGS. 26A-26D, the rearward portion 718 of cannula portion 712 of the axially displaceable element 700 is sealingly inserted through bore 662 of channel portion 660 of the barrel 582, in a manner that end surface 722 of cannula portion 712 is generally coplanar with flat rearward facing surface 642 of bulkhead 640 of barrel 582.

Rearward facing surface 734 of disc portion 702 of the axially displaceable element 700 abuts forward edge surface 654 of cylindrical wall 648 and forward edge surface 666 of additional channel portion 660 of barrel 582.

The axially displaceable element 700 is selectively positioned in the second position relative to static element 735 and luer connector portion 598. Specifically forward facing surface 732 of the axially displaceable element 700 is positioned more rearwardly of and spaced from flat wall surface 534 of the luer connector portion 598.

The rearward facing flat surface 458 of disc portion 452 is spaced more forwardly from forward facing surface 732 of the axially displaceable element 700.

End surface 724 of cannula portion 712 is positioned rearwardly of side opening 470 of forward flow channel portion 460 of static element 735. Accordingly, the side opening 470 of forward flow channel portion 460 of static element 735 is open.

Aperture 726 of cannula portion 712 of axially displaceable element 700 is closed by engagement of outer cylindrical surface 716 of forward portion 714 of axially displaceable element 700 with inner surface 465 of cylindrical bore 462 of forward flow channel portion 460 of static element 735.

In this second operative syringe orientation the following relationships exist between the first and second fluid volumes:

The first fluid volume is sealed from the outlet defined by surface 493 of bore 492 of flow channel 490 of the luer connector portion 598 by virtue of the fact that aperture 726 of cannula portion 712 of axially displaceable element 700 is closed by engagement of outer cylindrical surface 716 of forward portion 714 of axially displaceable element 700 with inner surface 465 of cylindrical bore 462 of forward flow channel portion 460 of static element 735.

The second fluid volume communicates with the outlet defined by surface 493 of bore 492 of flow channel 490 of the luer connector portion 598 via a forward portion of bore 462 by virtue of the fact that end surface 724 of cannula portion 712 is positioned rearwardly of side opening 470 of forward flow channel portion 460 of static element 735, thereby causing the side opening 470 of forward flow channel portion 460 of static element 735 to be open.

Figure 27A:
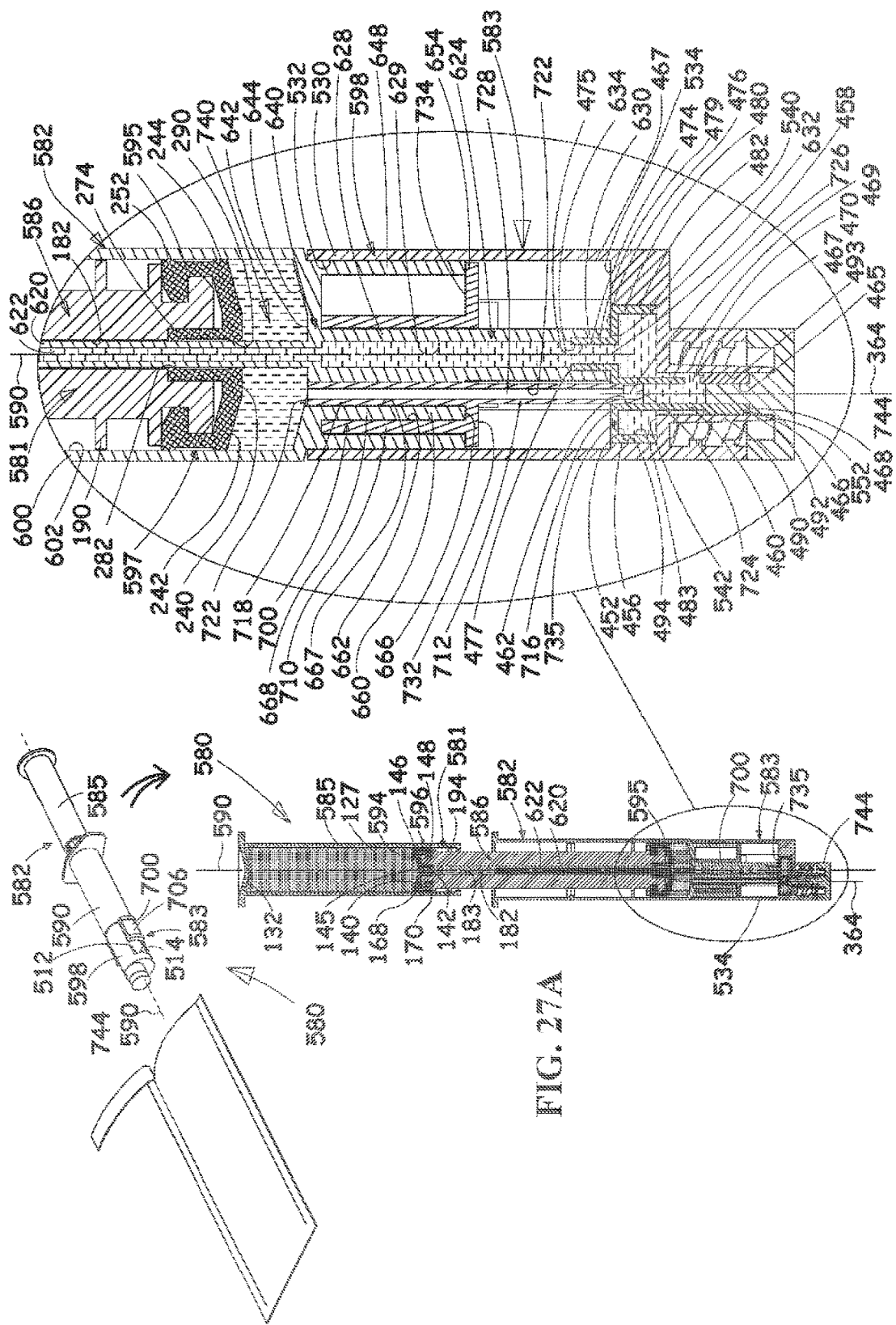
FIG. 27A is a simplified combined pictorial and sectional view illustration of the multi-chamber syringe of FIGS. 17A-26D, including a reconstitutable medicament and a reconstitution and flushing solution, in a first operative state, which is preferably the state in which the multi-chamber syringe is shipped and stored prior to use.

Reference is now made to FIG. 27A, which illustrates the multi-chamber syringe 580, including a reconstitutable medicament 740 and a reconstitution and flushing solution 742, in a first operative state, which is preferably the state in which the multi-chamber syringe 580 is shipped and stored prior to use.

As seen in FIG. 27A, in the first operative state, the reconstitutable medicament 740 is located within the barrel 582 in a reconstitutable medicament volume delimited by the following:

forward flat surface 240 and tapered ring surface 242 of piston ring 595; and surfaces 602, 642 and 644 and channel member 620 of circular cylindrical chamber 600 of barrel 582.

The reconstitution and flushing solution 742 is located within piston assembly housing portion 585 in an initial reconstitution and flushing solution volume delimited by the following:

surfaces 127 and 132 of piston assembly housing portion 585;

surface 144 and recess 140 of piston ring 594;

surface 183 of bore 182 of plunger rod 586;

surfaces 621 and 623 of bore 622 of channel member 620;

surface 629 of bore 626 in channel portion 624 of barrel 582;

surfaces 477 and 475 of bore 476 in channel portion 474;

surface 456 of disc portion 452;

surface 483 of peripheral wall 480;

surfaces 467 and 469 and opening 470 of channel portion 460;

surface 724 of cannula 712; and surface 465 of bore 462 of channel portion 460.

It is noted that a forward portion of bore 492 of flow channel 490 of luer connector portion 598 is sealed by a cover 744.

As seen in FIG. 25A, in the first operative state, piston assembly 581 is partially inserted within barrel 582 along longitudinal axis 590.

It is appreciated that the following spatial relationships exist between the various elements:

The rearward-facing end portion 596 of plunger rod 586 is inserted into the piston assembly housing portion 585, in a manner that outer cylindrical surfaces 168 and 170 of rearward-facing and forward-facing flanges 146 and 148 of the piston ring 594 are sealingly slidably arranged within interior surface 127 of piston assembly housing portion 585;

The forward-facing end portion 597 of the plunger rod 586 is inserted into the barrel 582 in a manner that radially outward facing surfaces 244 and 252 of the piston ring 595 are sealingly slidably arranged within cylindrical inner surface 602 of circular cylindrical chamber 600 of barrel 582;

The rearward-facing end portion 596 of the plunger rod 586 and the piston ring 594 mounted thereon are disposed within piston assembly housing portion 585 between the first and second positions thereof described hereinabove with reference to FIGS. 24A-24D, such that rearward-facing recess 140 of the piston ring 594 is forwardly spaced with respect to forward-facing surface 132 of the piston assembly housing portion 585;

The forward-facing end portion 597 of the plunger rod 586 and piston ring 595 mounted thereon are disposed within barrel 582 between the first and second positions thereof described hereinabove with reference to FIGS. 24A-24D, such that forward flat surface 240 and tapered ring surface 242 of the piston ring 595 are rearwardly spaced with respect to rearward facing surface 642 and tapered surface 644 of the barrel 582 respectively;

Internal channel member 620 of barrel 582 is inserted into axial bore 182 of the plunger rod 586 through circular cylindrical portion 274 of the piston ring 595. It is appreciated that internal channel member 620 of the barrel 582 is sealingly slidably arranged within the circular cylindrical portion 274 of the piston ring 595 due to engagement of the internal channel member 620 with inwardly-facing surfaces 282 and 290 of the circular cylindrical portion 274 of the piston ring 595;

The outer circumference of rearward flange 194 of plunger rod 586 substantially corresponds to internal surface 127 of the piston assembly housing portion 585. The outer circumference of the forward flange 190 of plunger rod 586 substantially corresponds to inner surface 602 of the barrel 582;

In this first operative state, the piston ring 594 and the piston ring 595 are both positioned between their respective first and second positions;

The valve assembly 583 is attached to the barrel 582, preferably by heat welding and alternatively by use of an adhesive or via a snap-fit arrangement. Inner cylindrical wall surface 532 of outer cylindrical wall surface 530 of luer connector portion 598 is preferably attached to slotted cylindrical wall 648 of barrel 582;

The obround cylindrical surface 668 of barrel 582 is at least partially inserted into a corresponding obround cylindrical portion 710 of axially displaceable element 700. Flow channel portion 474 of static element 735 is inserted into forward portion 630 of the forward channel portion 624 of barrel 582 such that surface 479 of flow channel portion 474 fluid sealingly engages surface 630 of forward channel portion 624. A rearward end of flow channel portion 474 abuts forward facing ring portion 634 of forward flow channel portion 624. Rearward facing flat surface 458 of static element 735 abuts forward end surface 632 of barrel 582;

Rearward portion 718 of cannula portion 712 of axially displaceable element 700 is at least partially inserted into bore 662 of channel portion 660 of barrel 582 in a slidably fluid sealing manner;

Vanes 708 of the axially displaceable element 700 are at least partially inserted into axially extending slots 670 of the barrel 582;

Grip portion 705 of axially displaceable element 700 is positioned between side edges 512 and 514 of luer connector portion 598 and grip portion 706 is positioned between side edges 522 and 524 of luer connector portion 598;

The disc portion 452 of static element 735 is positioned within the recess 494 of the luer connector portion 598, in a manner that the outwardly facing surface 482 of circumferential wall 480 of static element 735 tightly and fluid sealingly fits cylindrical surface 540 of recess 494;

Forward facing flat surface 456 of the disc portion 452 of static element 735 is spaced apart from the rearward facing flat surface 542 of recess 494 of luer connector portion 598;

Forward flow channel portion 460 of static element 735 is inserted into flow channel 490 of the luer connector portion 598, such that thickened forward portion 466 of forward flow channel portion 460 of static element 735 is fluid sealingly arranged within bore 492 of flow channel 490 of the luer connector portion 598 and the forward edge 468 of forward flow channel portion 460 is positioned rearwardly from forward facing edge 552 of flow channel 490 of the luer connector portion 598;

Cannula portion 712 of the axially displaceable element 700 is fluid sealingly fitted within forward flow channel portion 460 of static element 735; and The side opening 470 of forward flow channel portion 460 of static element 735 and aperture 726 of cannula portion 712 of the axially displaceable element 700 face in the same direction.

In the first operative state, which corresponds to the second operative syringe orientation, as seen in FIGS. 26A-26D, the rearward portion 718 of cannula portion 712 of the axially displaceable element 700 is sealingly inserted through bore 662 of channel portion 660 of the barrel 582, in a manner that end surface 722 of cannula portion 712 is coplanar with flat rearward facing surface 642 of bulkhead 640 of barrel 582.

Rearward facing surface 734 of disc portion 702 of the axially displaceable element 700 is disposed forwardly of and abutting forward edge surface 654 of cylindrical wall 648 and forward edge surface 666 of additional channel portion 660 of barrel 582.

The axially displaceable element 700 is selectively positioned in the second orientation relative to static element 735 and luer connector portion 598 (FIGS. 23A-23C). Specifically forward facing surface 732 of the axially displaceable element 700 is positioned rearwardly of and spaced apart from flat wall surface 534 of the luer connector portion 598.

The rearward facing flat surface 458 of disc portion 452 is located forwardly of and spaced apart from forward facing surface 732 of the axially displaceable element 700.

End surface 724 of cannula portion 712 is positioned rearwardly of side opening 470 of forward flow channel portion 460 of static element 735.

The side opening 470 of forward flow channel portion 460 of static element 735 is open and communicates with inner surface 465 of bore 462 of forward flow channel portion 460. Bore 462 of forward flow channel portion 460 is sealed by cover 744 at its forward end and by fluid sealing engagement of outer cylindrical surface 716 of forward portion 714 of axially displaceable element 700 with cylindrical bore 462 of forward flow channel portion 460 of static element 735 at its rearward end.

Aperture 726 of cannula portion 712 of axially displaceable element 700 is sealed closed by engagement of outer cylindrical surface 716 of forward portion 714 of axially displaceable element 700 with inner surface 465 of cylindrical bore 462 of forward flow channel portion 460 of static element 735.

End surface 724 of cannula portion 712 of element 700 is rearwardly spaced with respect to forward facing edge 552 of flow channel 490 of luer connector portion 598.

In this first operative state, the following relationships exist between fluid volumes:

The first fluid volume defined by surfaces 602, 620, 642, 644 of chamber 600; surface 667 of bore 662 of barrel 582; surface 722, aperture 726 and bore 728 of cannula 712 of the axially displaceable element 700; and surfaces 240 and 242 of piston ring 595 is sealed by closing of aperture 726, produced by sealing engagement of outer surface 716 of cannula 712 with inner surface 465 of flow channel 460 of static element 735.

The second fluid volume defined by surface 465, side opening 470, shoulder surface 467 and surface 469 of flow channel 460; surface 456 of disc portion 452; surface 483 of peripheral wall 480; surfaces 475 and 477 of bore 476 of rearward flow channel 474 of static element 735; surface 724 of axially displaceable element 700; and inner cylindrical surface 629 of portion 628 of channel portion 624; surfaces 621 and 623 associated with bore 622; surface 183 of bore 182 of the plunger rod 586; surface 145 associated with bore 142, surface 140 of flange 146 of rearward piston 594; and surfaces 127 and 132 of piston assembly housing portion 585 is sealed from forward portion of bore 492 of flow channel 490 of luer connector portion 598, as defined hereinbelow.

Side opening 470 of forward flow channel portion 460 of static element 735 is open and communicates with inner surface 465 of bore 462 of forward flow channel portion 460. Bore 462 of forward flow channel portion 460 is sealed by cover 744 at its forward end and by fluid sealing engagement of outer cylindrical surface 716 of forward portion 714 of axially displaceable element 700 with cylindrical bore 462 of forward flow channel portion 460 of static element 735 at its rearward end.

It is appreciated that the visually sensible different orientations of the axially displaceable member 700 for different operations may provide a safety feature. In the illustrated embodiment, when the axially displaceable element 700 is positioned in its first orientation, FIGS. 24A-24C, the medicament is in open communication with the syringe opening and thus the syringe 580 may present a hazard. When the axially displaceable element 700 is positioned at its second orientation, FIGS. 26A-26C, the flushing solution is in open communication with the syringe opening and thus the syringe 580 does not present a hazard.

Figure 27B:
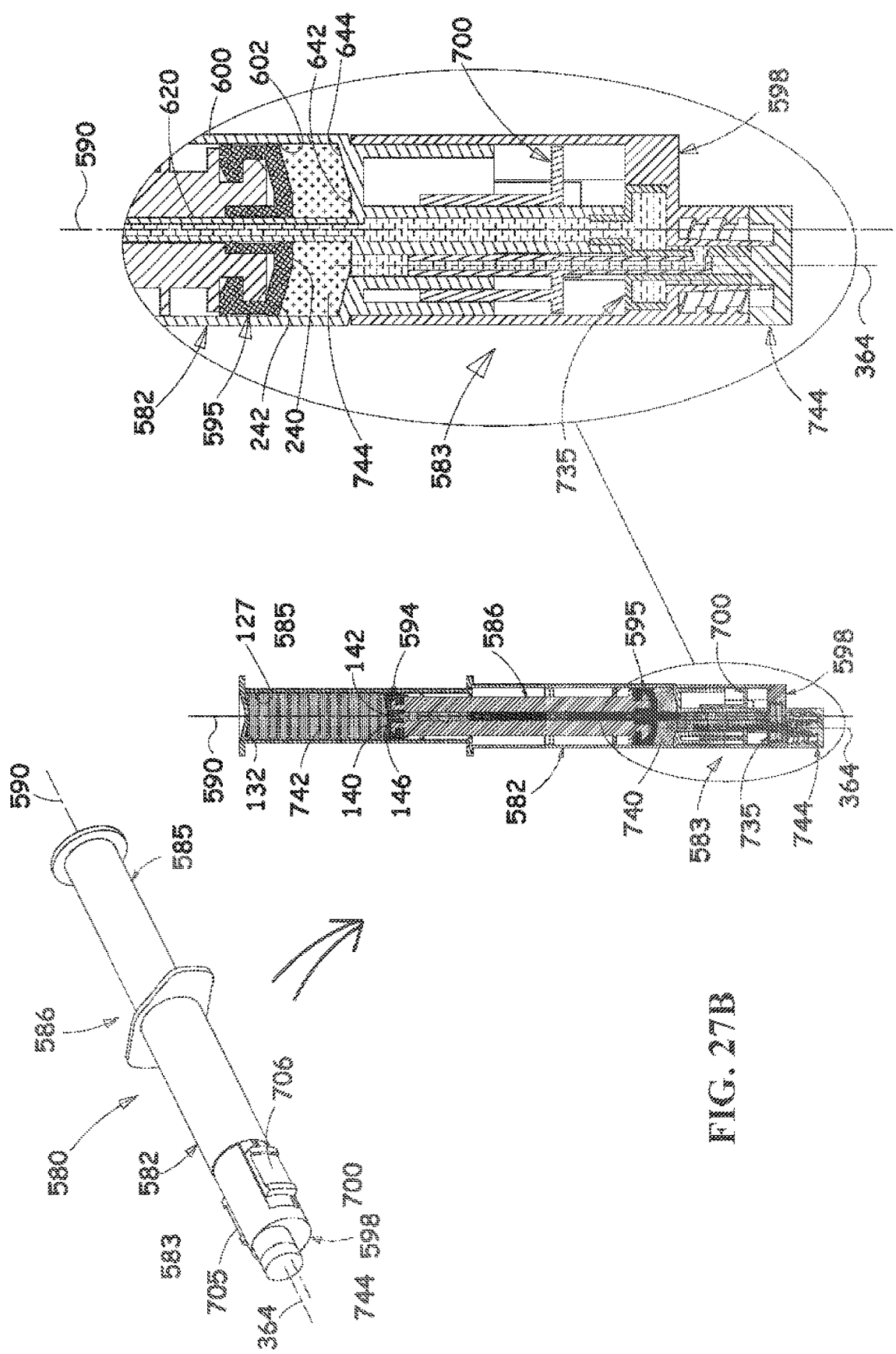
FIG. 27B is a simplified combined pictorial and sectional view illustration of the multi-chamber syringe of FIG. 27A in a second operative state, which is preferably the state in which the multi-chamber syringe is ready for reconstitution of the reconstitutable medicament.

Reference is now made to FIG. 27B, which illustrates the multi-chamber syringe 580 in a second operative state, which is preferably the state in which the multi-chamber syringe is ready for reconstitution of the reconstitutable medicament.

As seen in FIG. 27B, in the second operative state, as compared with FIG. 27A, which illustrates the first operative state, the axially displaceable element 700 is positioned at the intermediate operative syringe orientation, described above with reference to FIGS. 25A-25D, thereby providing fluid communication between the first fluid volume and the second fluid volume, specifically:

In the intermediate operative syringe orientation, shown in FIGS. 25A-25D, the rearward portion 718 of cannula portion 712 of the axially displaceable element 700 is sealingly inserted through bore 662 of channel portion 660 of the barrel 582, in a manner that end surface 722 of cannula portion 712 is less forwardly spaced from flat rearward facing surface 642 of bulkhead 640 of barrel 582.

Rearward facing surface 734 of disc portion 702 of the axially displaceable element 700 less forwardly spaced from forward edge surface 654 of cylindrical wall 648 and forward edge surface 666 of additional channel portion 660 of barrel 582.

The axially displaceable element 700 is selectively positioned in the intermediate position relative to static element 735 and luer connector portion 598. Specifically forward facing surface 732 of the axially displaceable element 700 is positioned rearwardly of and spaced from flat wall surface 534 of the luer connector 598.

The rearward facing flat surface 458 of disc portion 452 is spaced forwardly from forward facing surface 732 of the axially displaceable element 700.

End surface 724 of cannula portion 712 is positioned slightly forwardly of side opening 470 of forward flow channel portion 460 of static element 735.

Aperture 726 of cannula portion 712 is open to the side opening 470 of forward flow channel portion 460 of static element 735. Sealing engagement remains between outer cylindrical surface 716 of forward portion 714 of axially displaceable element 700 with inner surface 465 of cylindrical bore 462 of forward flow channel portion 460 of static element 735.

Figure 27C:
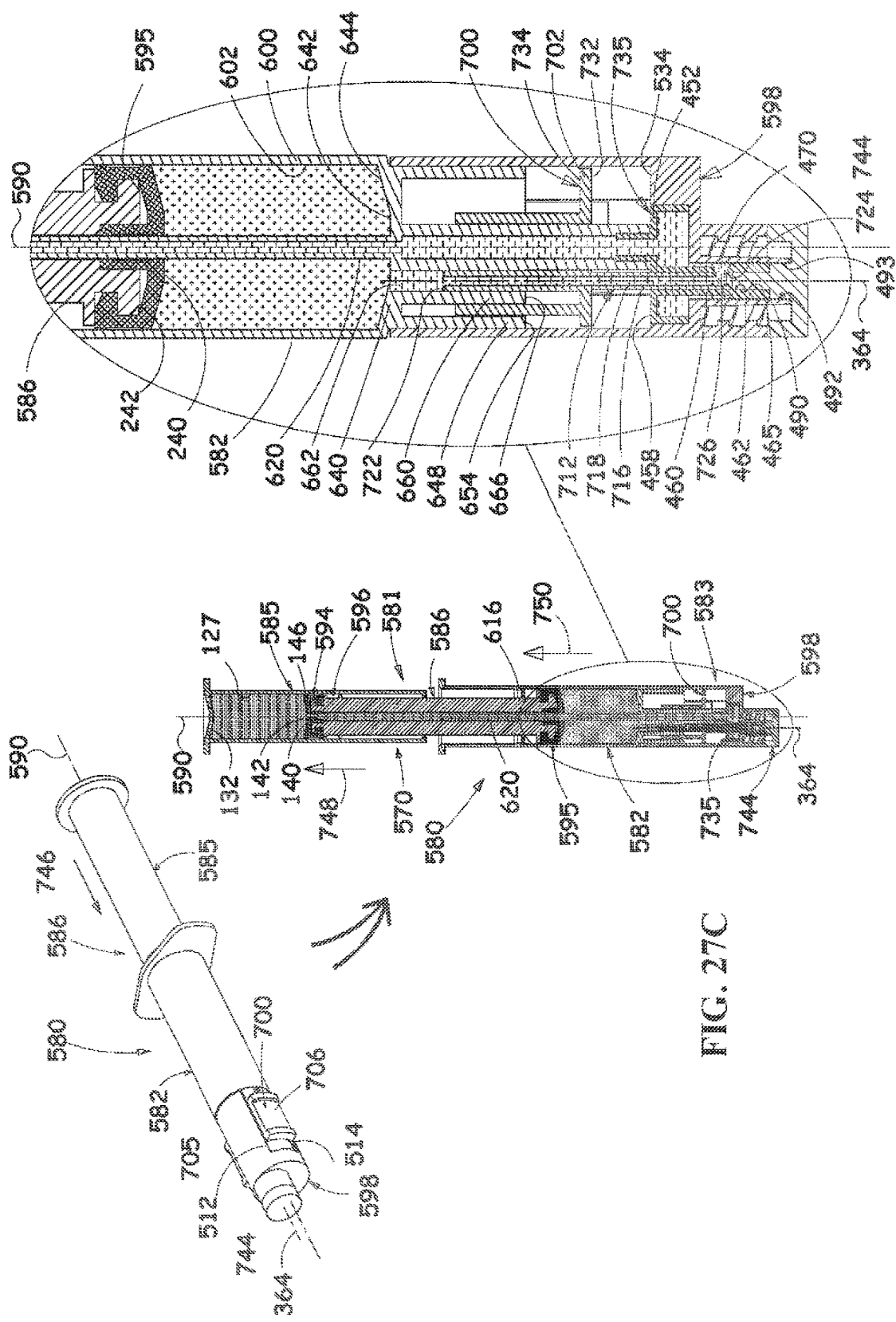
FIG. 27C is a simplified combined pictorial and sectional view illustration of the multi-chamber syringe of FIG. 27A in a third operative state, which is preferably the state in which the multi-chamber syringe has completed reconstitution of the reconstitutable medicament.

Reference is now made to FIG. 27C, which is a simplified combined pictorial and sectional view illustration of the multi-chamber syringe of FIG. 27A in a third operative state, which is preferably the state in which the multi-chamber syringe has completed reconstitution of the reconstitutable medicament.

In the third operative state, as compared with the first operative state, the piston assembly housing portion 585 is forwardly displaced relative to barrel 582 along longitudinal axis 590.

The mutual orientations of the various elements described in FIG. 27A remain essentially the same as in the first and second operative states, other than as specifically set forth hereinbelow:

The piston assembly housing portion 585 is slightly forwardly displaced along axis 590 by a first distance relative to barrel 582, as indicated by an arrow 746, and by a second distance, as indicated by an arrow 748, greater than the first distance, relative to plunger sub-assembly 570, which is rearwardly displaced along axis 590 by a third distance, as indicated by an arrow 750, which third distance is less than the first distance. Accordingly forwardly facing surface 132 of the piston assembly housing portion 585 is less rearwardly spaced from recess 140 of rearward piston 594 than in the first operative state, by the second distance. It is a particular feature of the present invention that the third distance indicated by arrow 750 is limited by engagement of forward flange 190 of plunger rod 586 with a shoulder 619 of inwardly facing plunger rod rearward motion limiting flange 616, thus limiting the amount of reconstituting solution which can be employed in reconstituting a medicament. As noted above, the location of flange 616 is preferably selected in accordance with a desired concentration of medicament.

The rearward displacement, indicated by arrow 750, of plunger sub-assembly 570 relative to barrel 582 by the third distance takes place as the result of flow of reconstitution and flushing solution from the initial reconstitution and flushing solution volume via bore 142 of piston ring 594, bore 182 of plunger rod 586, bore 622 of channel member 620, bore 626 of channel portion 624; bore 476 of channel portion 474, side opening 470, aperture 726 and bore 728 of cannula 712 and bore 662 of channel portion 660 to the reconstitutable medicament volume.

The rearward displacement of plunger sub-assembly 570 relative to barrel 582 by the third distance causes forward flat surface 240 and tapered ring surface 242 of the piston ring 595 to be more rearwardly spaced, by the third distance, from rearward facing surface 642 and tapered surface 644 of the barrel 582 respectively than in the first operative state described hereinabove with reference to FIG. 27A.

The piston rings 594 and 595 remain between their first and second positions, as described hereinabove with reference FIGS. 24A-24D.

It is a particular feature of this embodiment of the present invention that rearward displacement of plunger sub-assembly 570 relative to barrel 582 by the third distance due to flow of reconstitution and flushing solution from the initial reconstitution and flushing solution volume to the reconstitutable medicament volume.

It is a further particular feature of this embodiment of the present invention that this rearward displacement, indicated by arrow 750, results from the fact that the total cross sectional area, perpendicular to axis 590, of surface 240 and 242 of piston ring 595 is substantially larger than the total cross sectional area, perpendicular to axis 590, of recess 140 of piston ring 594.

This difference in cross-sectional areas causes a force to be exerted rearwardly on forward piston 595 which is greater than the force exerted forwardly on rearward piston 594, thus producing the rearward displacement of plunger subassembly 570 by the third distance relative to barrel 582.

The rearward displacement, indicated by arrow 750, of plunger sub-assembly 570 relative to barrel 582 by the third distance enlarges what was the reconstitutable medicament volume in the first and second operative states, shown in FIGS. 27A & 27B, to a larger reconstituted medicament volume in the third operative state, shown in FIG. 27C.

The displacement, indicated by arrow 748, of plunger sub-assembly 570 relative to piston assembly housing portion 585 by the second distance decreases what was the initial reconstitution and flushing solution volume in the first and second operative states, shown in FIGS. 27A & 27B to a smaller remaining flushing solution volume in the third operative state, shown in FIG. 27C.

The reconstituted medicament volume is sealed from the outlet defined by surface 493 of bore 492 of flow channel 490 of the luer connector portion 598 by virtue of engagement of outer cylindrical surface 716 of forward portion 714 of axially displaceable element 700 with inner surface 465 of cylindrical bore 462 of forward flow channel portion 460 of static element 735. Aperture 726 of cannula portion 712 of axially displaceable element 700 is in communication with side opening 470 of forward flow channel 460 of static element 735.

The remaining flushing solution volume communicates with the reconstituted medicament volume via communication of side opening 470 of forward flow channel portion 460 of static element 735 with aperture 726 of cannula 712 of axially displaceable element 700.

As seen in FIG. 27C, in the third operative state, as compared with FIG. 27B, which illustrates the second operative state, the axially displaceable element 700 remains in its intermediate orientation and the piston assembly housing portion 585 is further forwardly displaced relative to barrel 582.

As seen in FIG. 27C, in the third operative state, the reconstituted medicament volume is greater than the reconstitutable medicament volume of FIGS. 27A & 27B but remains delimited by the following:
  forward flat surface 240 and tapered ring surface 242 of piston ring 595;
  surfaces 602, 642 and 644 and channel member 620 of circular cylindrical chamber 600 of barrel 582.

As further seen in FIG. 27C, the remaining flushing solution volume is smaller than the initial reconstitution and flushing solution volume of FIGS. 27A & 27B and is now delimited by the following:
  surfaces 127 and 132 of piston assembly housing portion 585;
  surface 144 and recess 140 of piston ring 594;
  surface 183 of bore 182 of plunger rod 586;
  surfaces 621 and 623 of bore 622 of channel member 620;
  surface 629 of bore 626 in channel portion 624 of barrel 582;
  surfaces 477 and 475 of bore 476 in channel portion 474;
  surface 456 of disc portion 452;
  surface 483 of peripheral wall 480;
  surfaces 467 and 469 and opening 470 of channel portion 460;
  aperture 726, bore 728 and surface 722 of cannula 712; and
  surface 667 of bore 662 in channel portion 660 of barrel 582.

Figure 27D:
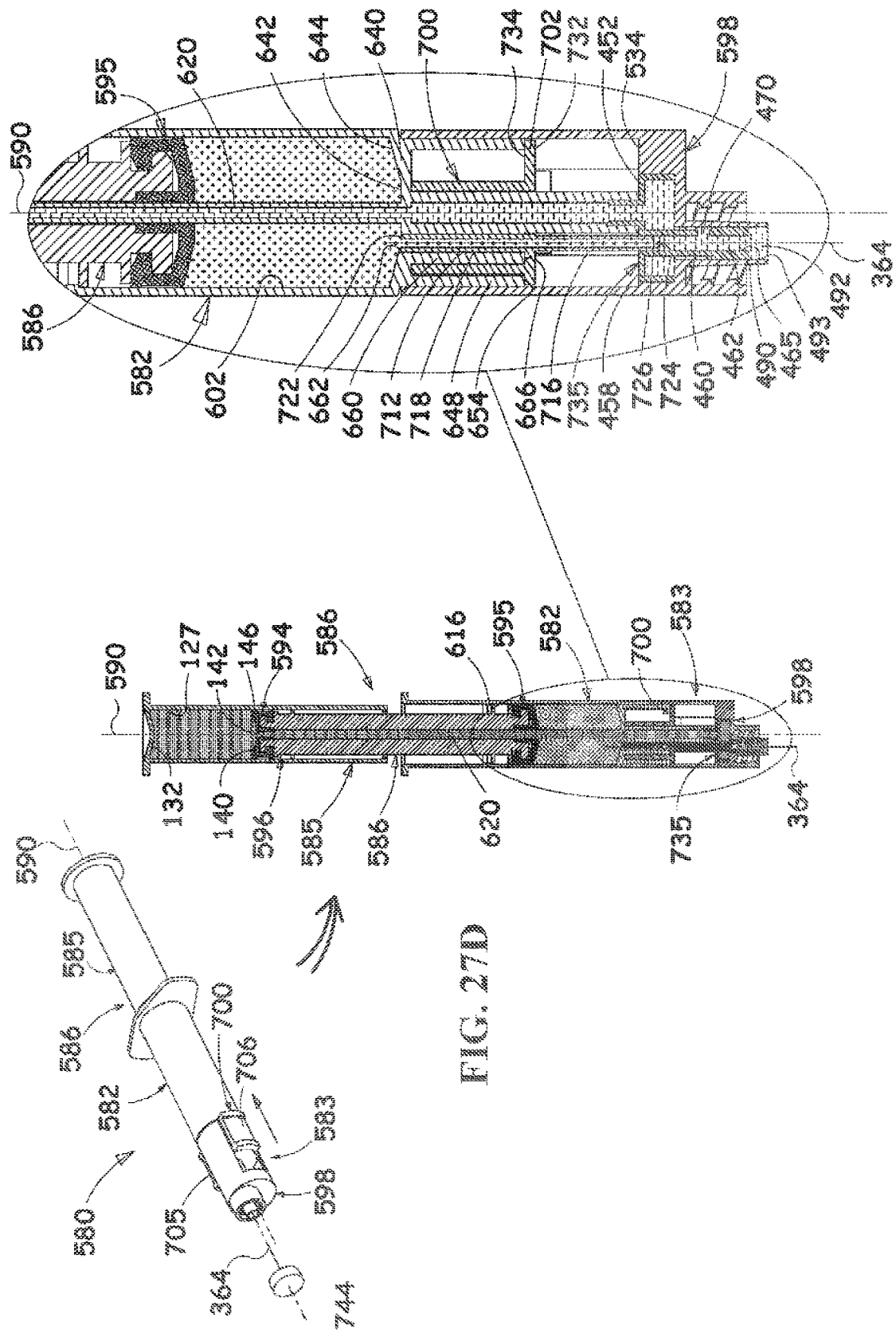
FIG. 27D is a simplified combined pictorial and sectional view illustration of the multi-chamber syringe of FIG. 27A in a fourth operative state, which is preferably the state in which the multi-chamber syringe is ready to use.

Reference is now made to FIG. 27D, which is a simplified combined pictorial and sectional view illustration of the multi-chamber syringe of FIGS. 27A-27C in a fourth operative state, which is preferably the state in which the multi-chamber syringe is ready to use and the cover is removed from the forward portion of bore 492 of flow channel 490 of luer connector portion 598.

As seen in FIG. 27D, in the fourth operative state, as compared with FIG. 27C, which illustrates the third operative state, the axially displaceable element 700 is in its second orientation (FIGS. 26A-26D) and specifically:
  The rearward portion 718 of cannula portion 712 of the axially displaceable element 700 is sealingly inserted through bore 662 of channel portion 660 of barrel 582, in a manner that end surface 722 of cannula portion 712 is generally coplanar with flat rearward facing surface 642 of bulkhead 640 of barrel 582.
  Rearward facing surface 734 of disc portion 702 of the axially displaceable element 700 abuts forward edge surface 654 of cylindrical wall 648 and forward edge surface 666 of additional channel portion 660 of barrel 582.

The axially displaceable element 700 is selectively positioned in the second position relative to static element 735 and luer connector portion 598. Specifically forward facing surface 732 of the axially displaceable element 700 is positioned rearwardly of and spaced from flat wall surface 534 of the luer connector portion 598.

The rearward facing flat surface 458 of disc portion 452 is spaced forwardly from forward facing surface 732 of the axially displaceable element 700.

End surface 724 of cannula portion 712 is positioned rearwardly of side opening 470 of forward flow channel portion 460 of static element 735. Accordingly, the side opening 470 of forward flow channel portion 460 of static element 735 is open.

Aperture 726 of cannula portion 712 of axially displaceable element 700 is closed by engagement of outer cylindrical surface 716 of forward portion 714 of axially displaceable element 700 with inner surface 465 of cylindrical bore 462 of forward flow channel portion 460 of static element 735.

The following relationships exist between the first and second fluid volumes:
  The first fluid volume is sealed from the outlet defined by surface 493 of bore 492 of flow channel 490 of the luer connector portion 598 by virtue of the fact that aperture 726 of cannula portion 712 of axially displaceable element 700 is closed by engagement of outer cylindrical surface 716 of forward portion 714 of axially displaceable element 700 with inner surface 465 of cylindrical bore 462 of forward flow channel portion 460 of static element 735.
  The second fluid volume communicates with the outlet defined by surface 493 of bore 492 of flow channel 490 of the luer connector portion 598 via a forward portion of bore 462 by virtue of the fact that end surface 724 of cannula portion 712 is positioned rearwardly of side opening 470 of forward flow channel portion 460 of static element 735, thereby causing the side opening 470 of forward flow channel portion 460 of static element 735 to be open.

It is a particular feature of this embodiment of the invention that the medicament is sealingly retained in the reconstituted medicament volume and does not remain in the outlet defined by surface 493 of bore 492 of flow channel 490 of the luer connector portion 598, as shown.

Figure 27E:
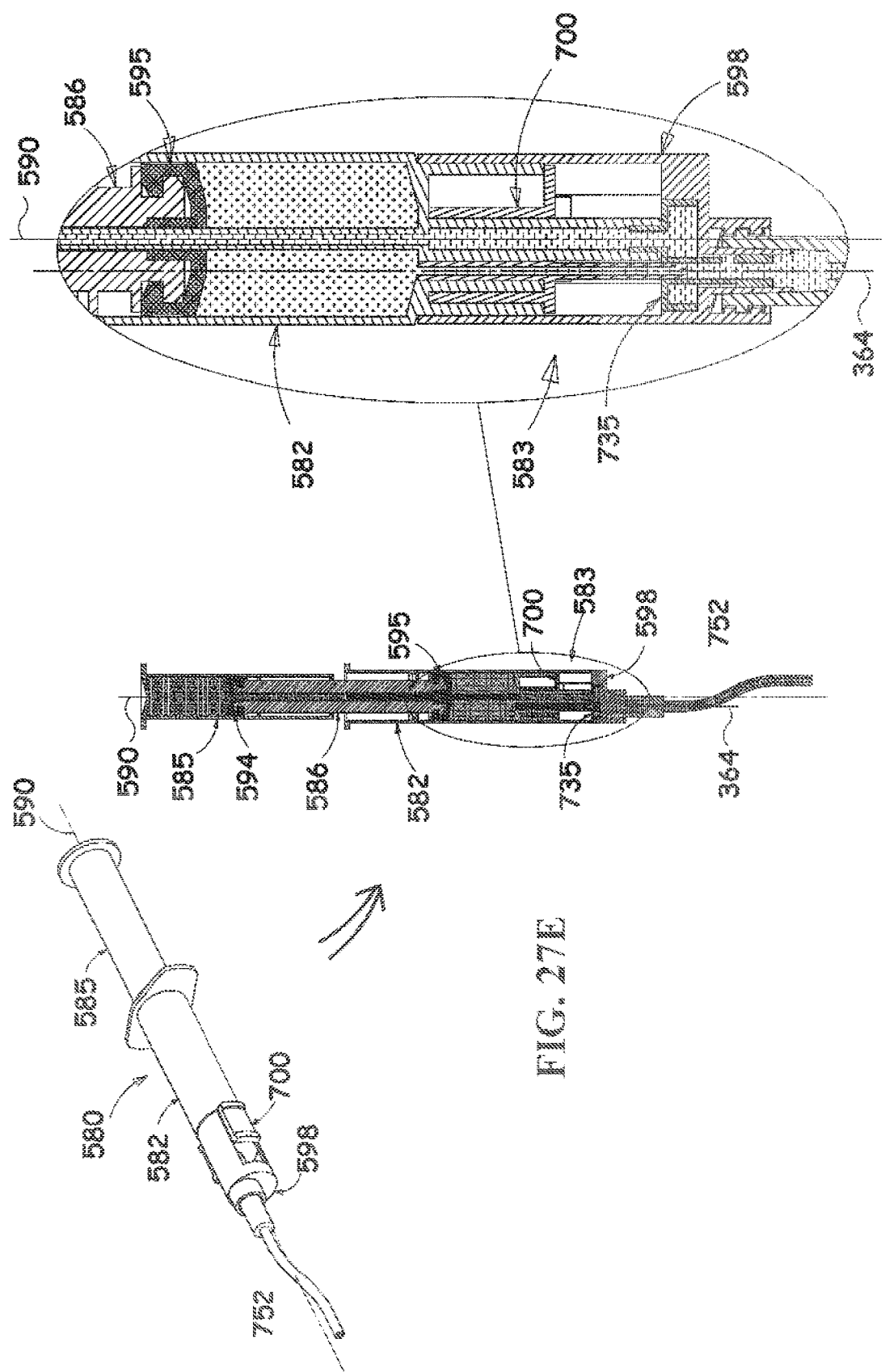
FIG. 27E is a simplified combined pictorial and sectional view illustration of the multi-chamber syringe of FIG. 27A in a fifth operative state, which is preferably the state in which the multi-chamber syringe is coupled at its outlet to a catheter and injects flushing solution into the catheter.

Reference is now made to FIG. 27E, which illustrates the multi-chamber syringe 580 in a fifth operative state, in which the multi-chamber syringe is coupled at its outlet defined by surface 493 of bore 492 of flow channel 490 of the luer connector portion 598 to a catheter 752 and injects flushing solution into the catheter. The relative orientations of the elements of the multi-chamber syringe 580 are essentially unchanged from those described hereinabove with reference to FIG. 27D.

Figure 27F:
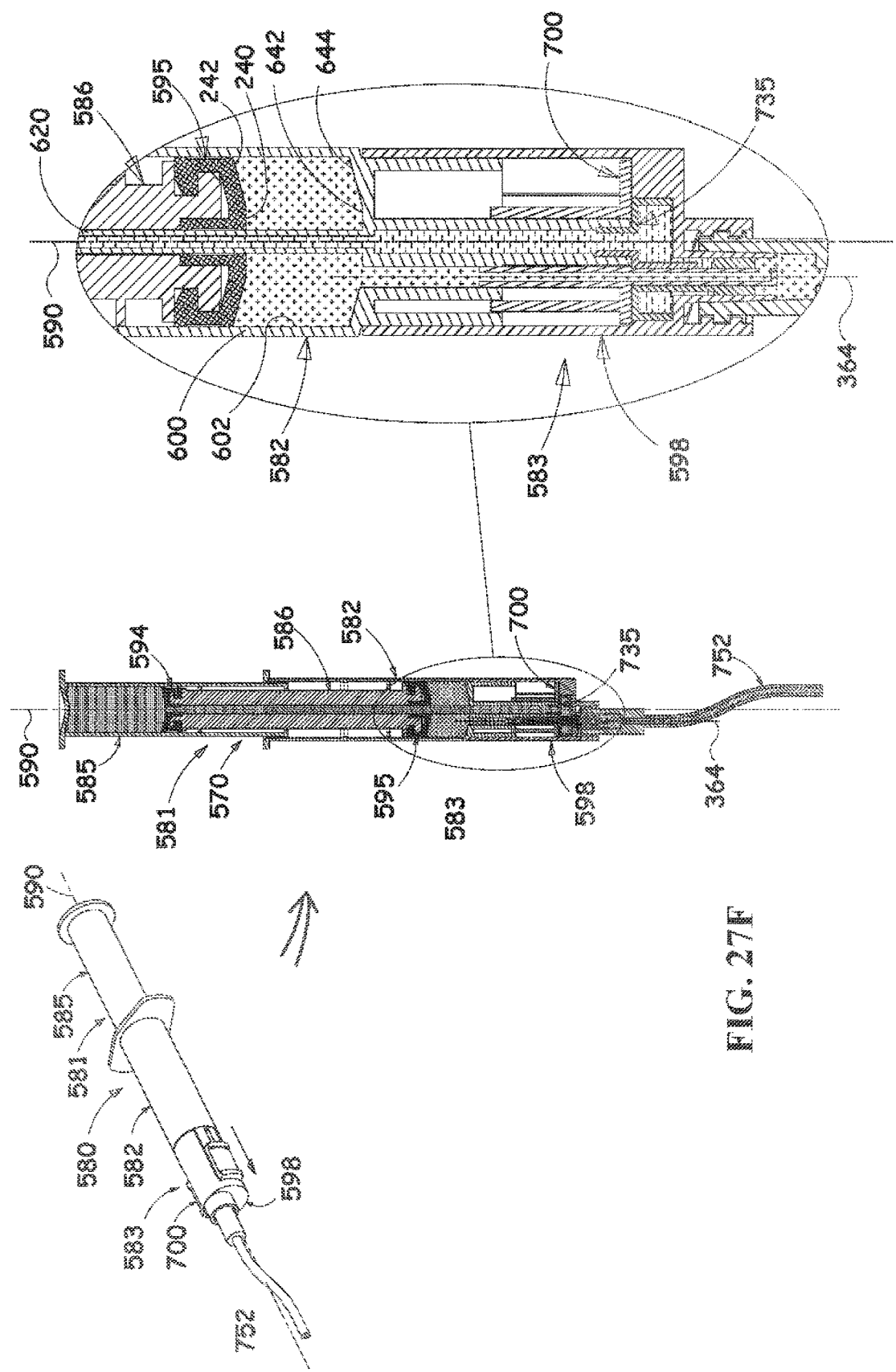
FIG. 27F is a simplified combined pictorial and sectional view illustration of the multi-chamber syringe of FIG. 27A in a sixth operative state, which is preferably the state in which the multi-chamber syringe injects medication into the catheter.

Reference is now made to FIG. 27F, which illustrates the multi-chamber syringe 580 in a sixth operative state, which is preferably the state in which the multi-chamber syringe 580 injects medication into the catheter 752, the axially displaceable element 700 is in its first orientation and both piston assembly housing portion 585 and the plunger subassembly 570 of the piston assembly 581 are pushed forwardly relative to barrel 582.

As compared with the arrangement shown in FIG. 27E, here forward flat surface 240 and tapered ring surface 242 of the piston ring 595 are less rearwardly spaced from rearward facing surface 642 and tapered surface 644 of the barrel 582 respectively, thus decreasing the reconstituted medication volume and forcing the reconstituted medication into the catheter 752 via the outlet defined by surface 493 of bore 492 of flow channel 490 of the luer connector portion 598.

The piston ring 595 is displaced more forwardly between its first and second positions (FIGS. 24A-24D), piston ring 594 remains in its position shown in FIG. 27E, due to the positive pressure produced in the remaining flushing solution volume by forward directed pressure exerted on the piston assembly 581. This is a particular feature of this embodiment of the present invention.

In the sixth operative state, due to the forward displacement of the piston assembly 581 in the barrel 582:

the reconstituted medicament volume is decreased relative to its state in the fifth operative state and at least a portion of the portion of the reconstituted medicament volume defined by surfaces 602, 620, 642, 644 of chamber 600 is thereby lost, with the result that the medicament that had earlier been reconstituted with the flushing solution from the initial reconstituting and flushing solution volume is injected into the catheter 752.

Figure 26C:
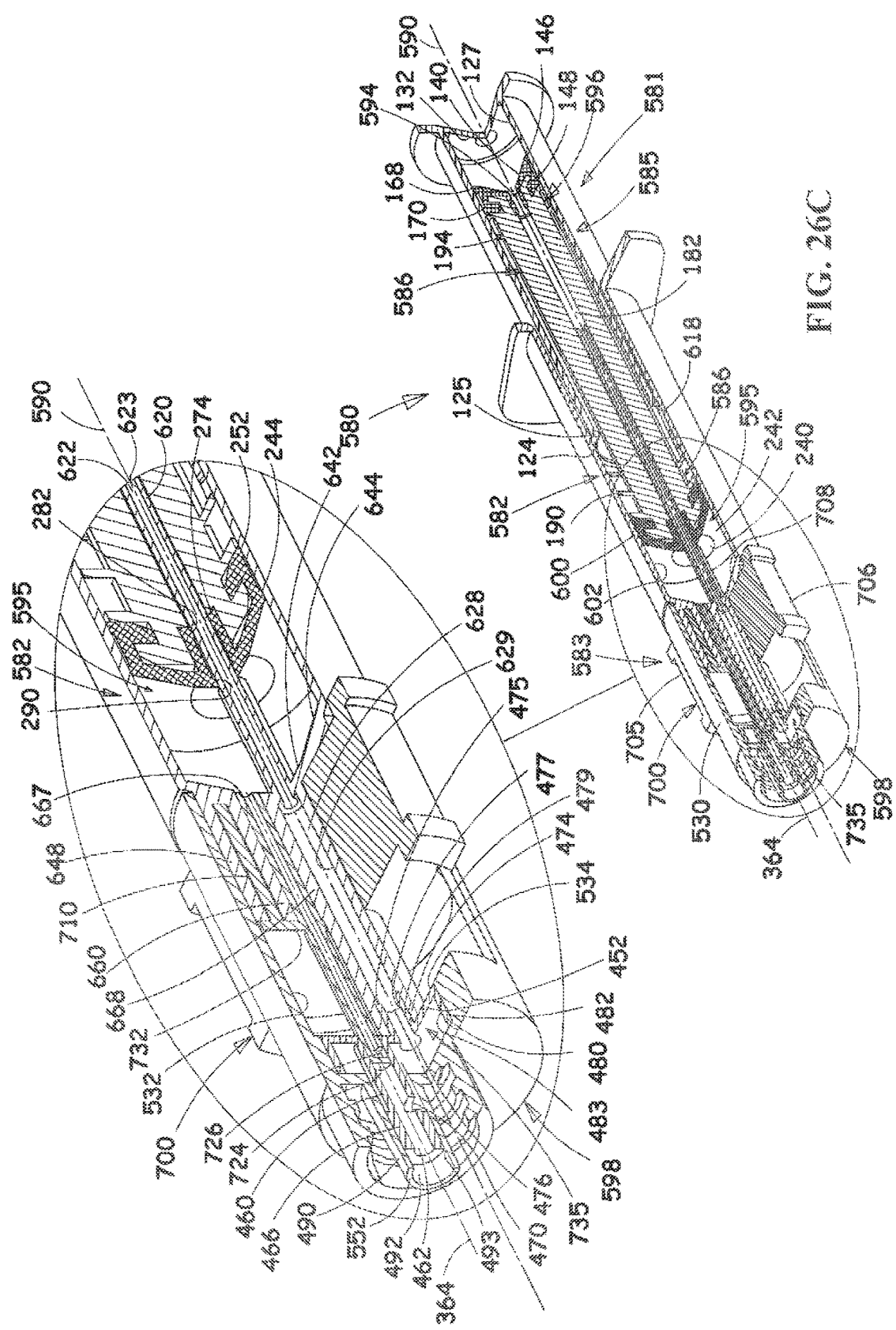
FIGS. 26C & 26D are simplified respective cut-away and sectional views of the assembled multi-chamber syringe of FIGS. 17A-18B, shown in the second operative syringe orientation.
Figure 26D:
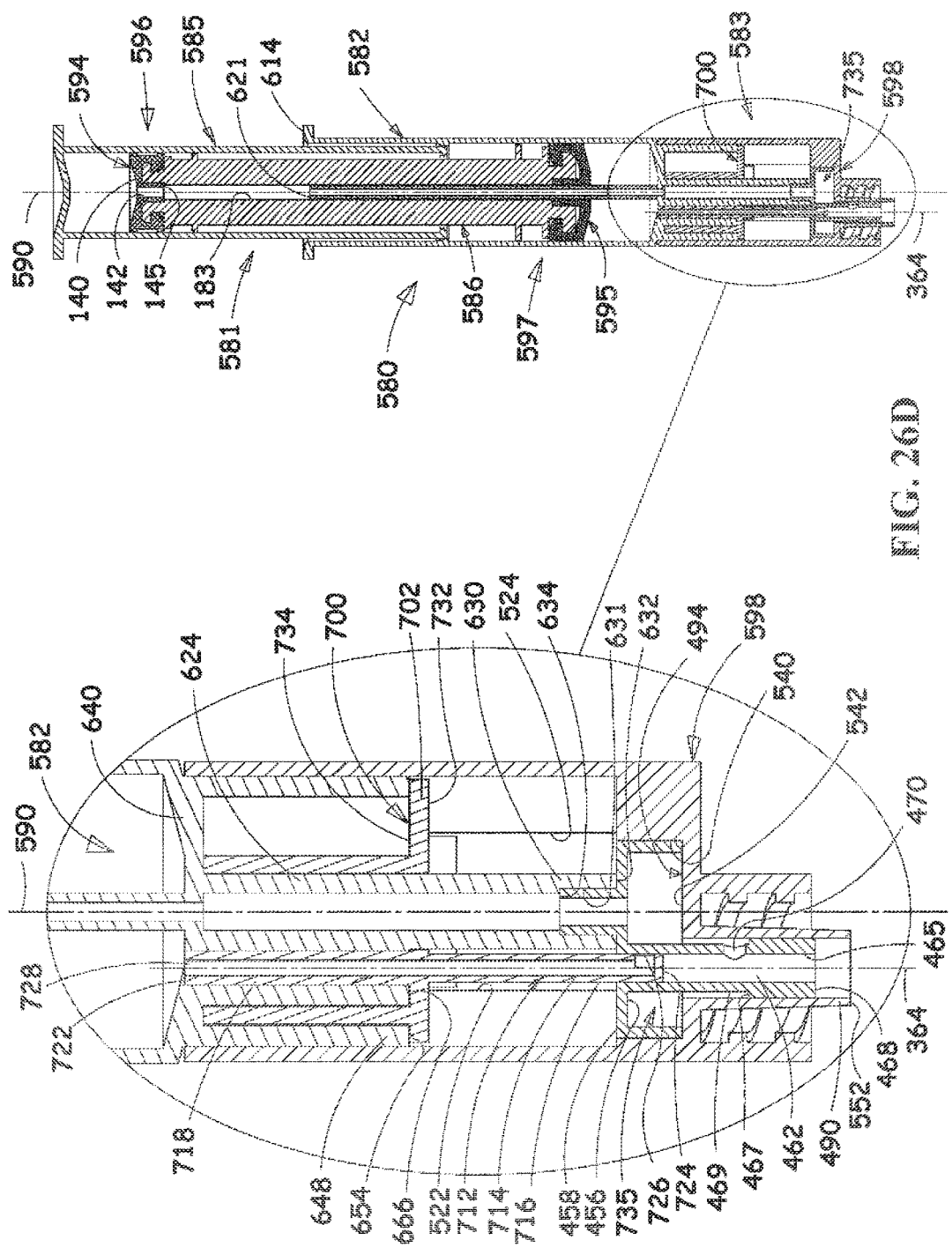

Once a desired amount of medication is aspirated, the axially displaceable element is rearwardly displaced to its second orientation, FIGS. 26A-26C.

It is a particular feature of an embodiment of the present invention that during this rearward displacement of the axially displaceable element 700 relative to the static element 735 and to the luer connector portion 598, the amount of residual medicament in the flow channel 490 of the luer connector portion 598 is substantially decreased. Preferably the amount of residual medicament is decreased by approximately 75% as compared with the amount of residual medicament in a standard luer connector, where neither axially displaceable element 700 nor static element 735 present.

This reduction in the amount of residual medicament takes place due to the fact that the forward channel portion 460 of the static element 735 and the cannula portion 712 of the axially displaceable element 700 occupy a substantial portion of the volume of the flow channel 490 of the luer connector portion 598.

Additionally, there is provided in accordance with a preferred embodiment of the present invention, fluid sealing engagement between the inner surface 465 of the forward flow channel 460 of the static element 735 and the outer surface 716 of the cannula portion 712. When the cannula portion 712 is displaced rearwardly to its second orientation, FIGS. 26A-26C, the closed end 724 of the cannula portion 712 is positioned rearwardly of the forward end 468 of the static element 735 and due to the sealing engagement of the cannula portion 712 and the forward flow channel portion 460 of the static element 735, the medicament remains sealed within the first fluid volume.

It is a further particular feature of the present invention that during rearward displacement of axial displacement element 700 relative to the static element 735, the outer surface 716 of cannula portion 712 wipes the residual medicament from inner surface 465 of the forward flow channel 460 of the static element 735 and provides for sealing of the medicament in the first fluid volume.

Figure 27G:
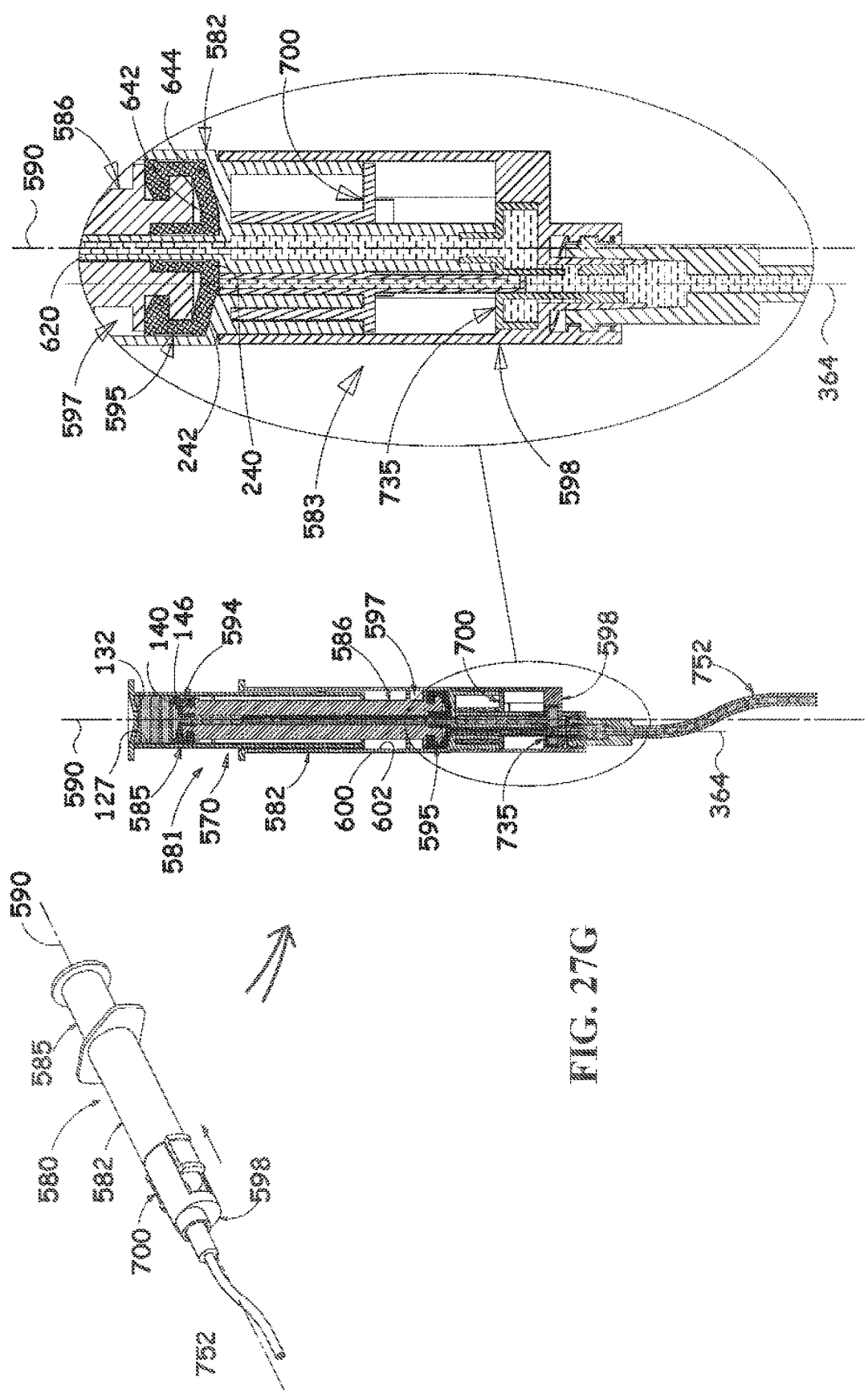
FIG. 27G is a simplified combined pictorial and sectional view illustration of the multi-chamber syringe of FIG. 27A in a seventh operative state, which is preferably the state in which the multi-chamber syringe has completed injection of the medication into the catheter and injects flushing solution into the catheter.

Reference is now made to FIG. 27G, which illustrates the multi-chamber syringe 580 in a seventh operative state, which is preferably the state in which the multi-chamber syringe has completed injection of the medication into the catheter 752 and injects flushing solution into the catheter 752 and both piston assembly housing portion 585 and the plunger sub-assembly 570 of the piston assembly 581 are further pushed forwardly relative to barrel 582 and thereafter the axially displaceable element 700 is shifted to its second orientation.

As compared with the arrangement shown in FIG. 27F, here forward-facing end portion 597 of the plunger rod 586 and the piston ring 595 mounted thereon return to the first position (FIGS. 24A-24D) defined by engagement of forward flat surface 240 and tapered ring surface 242 of the piston ring 595 with the rearward facing surface 642 and tapered surface 644 of the barrel 582 respectively.

The piston assembly housing portion 585 of piston assembly 581 is in a partially inserted orientation with respect to the remainder of piston assembly 581 and specifically displaced forwardly with respect to piston ring 594.

In the seventh operative state, due to the further forward displacement of piston assembly housing portion 585 in the barrel 582:

the remaining flushing solution volume is decreased relative to its state in the sixth operative state and at least a portion of the remaining flushing solution volume defined by surface 140 of flange 146 of rearward piston 594 and surfaces 127 and 132 of the piston assembly housing portion 585 is thereby eliminated, with the result that flushing solution is injected into the catheter 752.

Figure 27H:
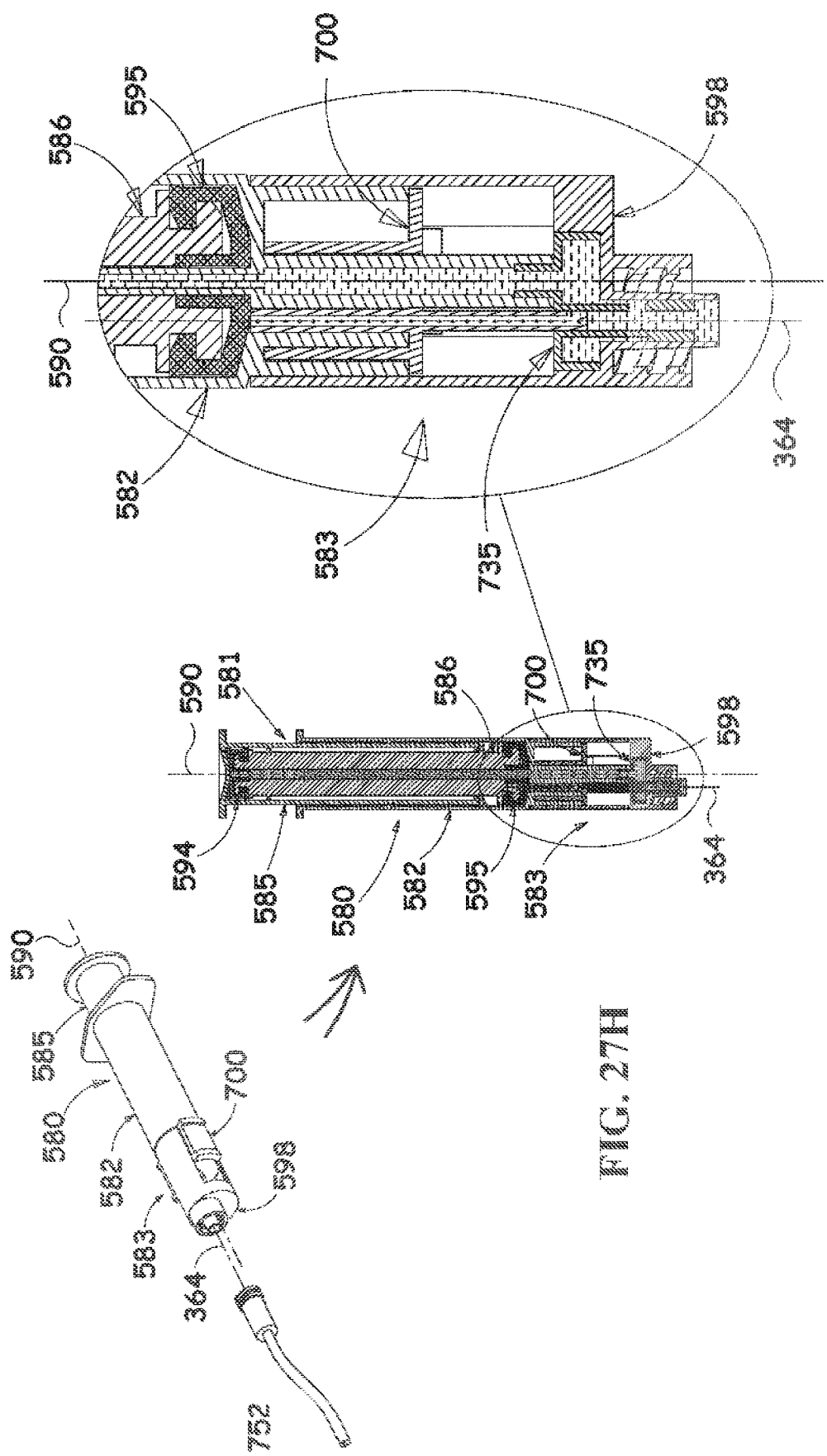
FIG. 27H is a simplified combined pictorial and sectional view illustration of the multi-chamber syringe of FIG. 27A in an eighth operative state, which is preferably the state in which the multi-chamber syringe is decoupled from the catheter.

Reference is now made to FIG. 27H, which illustrates the multi-chamber syringe 580 in an eighth operative state, which is preferably the state in which the multi-chamber syringe 580 is decoupled from the catheter 752 and the axially displaceable element 700 remains in its second orientation (FIGS. 26A-26D). It is a particular feature of this embodiment of the present invention that at this final operative stage, the outlet defined by surface 493 of bore 492 of flow channel 490 of the luer connector portion 598 has been flushed with flushing solution. The fact that the outlet of the multi-chamber syringe 580 is flushed with flushing solution at the final operative state enables safe disposal of the syringe 580.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The invention claimed is:

1. A medical fluid supply device comprising:
   at least first and second fluid containers which are physically moveable relative to each other, said first fluid container containing a first fluid and said second fluid container containing a second fluid;
   at least first and second selectably openable fluid communication pathways associated with said first and second fluid containers; and
   at least one selector switch assembly for selectably opening said first and second selectably openable fluid communication pathways,
   wherein:
   relative movement of said first and second fluid containers changes the amount of fluid in at least one of said at least first and second fluid containers in accordance with a state of said at least one selector switch assembly; and
   relative movement of said first and second fluid containers supplies at least a portion of said first fluid from said first fluid container and thereafter supplies at least a portion of said second fluid from said second fluid container, while some of said first fluid remains in said first fluid container.

2. A medical fluid supply device according to claim 1, and wherein said at least one selector switch assembly including a luer connector and a valve assembly disposed within said luer connector, such that said valve assembly occupies a majority of said interior volume of said luer connector.

3. A medical fluid supply device according to claim 2, and wherein said valve assembly is axially slidably movable within said luer connector.

4. A medical fluid supply device according to claim 2 and further comprising:
a piston assembly and a barrel which are arranged for mutual telescopic displacement and wherein said at least first and second fluid containers comprise a first fluid container located within said barrel and a second fluid container located within said piston assembly.

5. A medical fluid supply device according to claim 2 and wherein said at least one selector switch assembly is manually operable for selectably opening at least one of said first and second fluid communication pathways associated with said first and second fluid containers.

6. A medical fluid supply device according to claim 2 and also comprising a piston assembly and a barrel which are arranged for mutual telescopic displacement and wherein:
said at least first and second fluid containers comprise a first fluid container located within said barrel and a second fluid container located within said piston assembly; and
said piston assembly includes a piston assembly housing portion and a plunger rod, which is disposed within said piston assembly housing portion and is slidable therewithin along a common longitudinal axis within predetermined axial limits.

7. A medical fluid supply device according to claim 1 and further comprising:
a piston assembly and a barrel which are arranged for mutual telescopic displacement and wherein said at least first and second fluid containers comprise a first fluid container located within said barrel and a second fluid container located within said piston assembly.

8. A medical fluid supply device according to claim 1, and wherein said at least first and second fluid containers are arranged to be mutually displaceable along a common longitudinal axis and wherein mutual displacement of said first and second fluid containers along said common longitudinal axis changes the amount of fluid in at least one of said at least first and second fluid containers in accordance with a state of said at least one selector switch assembly.

9. A medical fluid supply device according to claim 1 and also comprising a valve assembly, which is operated by said at least one selector switch assembly for selectably opening said first and second selectably openable fluid communication pathways in response to positioning of said at least one selector switch assembly.

10. A medical fluid supply device according to claim 1 and wherein mutual displacement of said first and second fluid containers changes the amount of fluid in at least one of said at least first and second fluid containers in accordance with a state of said at least one selector switch assembly.

11. A medical fluid supply device according to claim 1 and wherein said at least one selector switch assembly is manually operable for selectably opening at least one of said first and second fluid communication pathways associated with said first and second fluid containers.

12. A medical fluid supply device according to claim 1 and also comprising a piston assembly and a barrel which are arranged for mutual telescopic displacement and wherein:
said at least first and second fluid containers comprise a first fluid container located within said barrel and a second fluid container located within said piston assembly; and
said piston assembly includes a piston assembly housing portion and a plunger rod, which is disposed within said piston assembly housing portion and is slidable therewithin along a common longitudinal axis within predetermined axial limits.

13. A medical fluid supply device, comprising:
at least first and second fluid containers, said first fluid container containing a first fluid and said second fluid container containing a second fluid;
at least one fluid flow passageway;
at least first and second selectably openable fluid communication pathways connecting said at least first and second fluid containers with said fluid flow passageway; and
at least one selector switch assembly for selectably opening said first and second selectably openable fluid communication pathways in a manner that only one of said at least first and second fluid containers is connected to said at least one fluid flow passageway at any given time,
wherein relative movement of said first and second fluid containers supplies at least a portion of said first fluid from said first fluid container and thereafter supplies at least a portion of said second fluid from said second fluid container, while some of said first fluid remains in said first fluid container.

14. A medical fluid supply device according to claim 13 and further comprising a piston assembly and a barrel which are arranged for mutual telescopic displacement and wherein said at least first and second fluid containers comprise a first fluid container located within said barrel and a second fluid container located within said piston assembly.

15. A medical fluid supply device according to claim 13, and wherein said at least first and second fluid containers are arranged to be mutually displaceable along a common longitudinal axis and wherein mutual displacement of said first and second fluid containers along said common longitudinal axis changes the amount of fluid in at least one of said at least first and second fluid containers in accordance with a state of said at least one selector switch assembly.

16. A medical fluid supply device according to claim 13 and also comprising a valve assembly, which is operated by said at least one selector switch assembly for selectably opening said first and second selectably openable fluid communication pathways in response to positioning of said at least one selector switch assembly.

17. A medical fluid supply device according to claim 13 and wherein mutual displacement of said first and second fluid containers changes the amount of fluid in at least one of said at least first and second fluid containers in accordance with a state of said at least one selector switch assembly.

18. A medical fluid supply device according to claim 13 and wherein said at least one selector switch assembly is manually operable for selectably opening at least one of said first and second fluid communication pathways associated with said first and second fluid containers.

19. A medical fluid supply device according to claim 13 and also comprising a piston assembly and a barrel which are arranged for mutual telescopic displacement and wherein:
- said at least first and second fluid containers comprise a first fluid container located within said barrel and a second fluid container located within said piston assembly; and
- said piston assembly includes a piston assembly housing portion and a plunger rod, which is disposed within said piston assembly housing portion and is slidable therewithin along a common longitudinal axis within predetermined axial limits.

* * * * *